(12) United States Patent
Nir et al.

(10) Patent No.: US 12,318,285 B2
(45) Date of Patent: *Jun. 3, 2025

(54) MECHANICALLY EXPANDABLE HEART VALVE

(71) Applicant: EDWARDS LIFESCIENCES CORPORATION, Irvine, CA (US)

(72) Inventors: Noam Nir, Pardes-Hanna (IL); Michael Bukin, Pardes Hanna (IL); Boaz Manash, Givat Ada (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/235,720

(22) Filed: Aug. 18, 2023

(65) Prior Publication Data

US 2024/0074851 A1    Mar. 7, 2024

Related U.S. Application Data

(60) Continuation of application No. 17/339,316, filed on Jun. 4, 2021, now Pat. No. 11,951,003, which is a
(Continued)

(51) Int. Cl.
*A61F 2/24*     (2006.01)
*A61F 2/95*     (2013.01)

(52) U.S. Cl.
CPC .......... *A61F 2/2418* (2013.01); *A61F 2/2415* (2013.01); *A61F 2/243* (2013.01);
(Continued)

(58) Field of Classification Search
CPC ...... A61F 2/844; A61F 2/2418; A61F 2/2439; A61F 2/243; A61F 2/2436; A61F 2/9517; A61F 2002/9511
See application file for complete search history.

(56) References Cited

U.S. PATENT DOCUMENTS 3,409,013 A    11/1968 Berry
3,548,417 A    12/1970 Ronnie et al.
(Continued)

FOREIGN PATENT DOCUMENTS

CN    105517509 A    4/2016
DE    0144167 C      9/1903
(Continued)

OTHER PUBLICATIONS

H.R. Andersen, et al. "Transluminal Implantation of Artificial Heart Valve. Description of a New Expandable Aortic Valve and Inital Results with impantation by Catherter Technique in Closed Chest Pig," European Heart Journal, No. 13, pp. 704-708. 1992.
(Continued)

*Primary Examiner* — Tuan V Nguyen
(74) *Attorney, Agent, or Firm* — Klarquist Sparkman, LLP; Joel B. German

(57) ABSTRACT

In one embodiment, a prosthetic valve assembly includes an annular frame being radially expandable and compressible between a radially compressed configuration and a radially expanded configuration, a valvular structure comprising a plurality of leaflets mounted inside the annular frame, a plurality of posts mounted on an interior surface of the annular frame, and a pair of commissure attachment members extending outwardly from each post and away from each other. Each two adjacent leaflets can form a pair of commissure tabs. Each pair of commissure tabs can be attached to a corresponding pair of the commissure attachment members.

22 Claims, 33 Drawing Sheets

Related U.S. Application Data division of application No. 16/208,263, filed on Dec. 3, 2018, now Pat. No. 11,026,785, which is a continuation-in-part of application No. 15/995,528, filed on Jun. 1, 2018, now Pat. No. 10,869,759.

(60) Provisional application No. 62/515,437, filed on Jun. 5, 2017.

(52) U.S. Cl.
CPC ........... *A61F 2/2436* (2013.01); *A61F 2/9517* (2020.05); *A61F 2220/0033* (2013.01); *A61F 2220/0075* (2013.01); *A61F 2220/0091* (2013.01)

(56) References Cited

U.S. PATENT DOCUMENTS

| | | |
|---|---|---|
| 3,587,115 A | 6/1971 | Donald |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,860,780 A | 1/1999 | Lenac et al. |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |

(56) References Cited

U.S. PATENT DOCUMENTS

| | | |
|---|---|---|
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0111772 A1 | 5/2006 | White et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0183275 A1 | 7/2008 | Schmid et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0230956 A1 | 9/2011 | White |
| 2011/0319991 A1 | 12/2011 | Hariton et al. |
| 2012/0030090 A1 | 2/2012 | Johnston et al. |
| 2012/0089223 A1* | 4/2012 | Nguyen ............... A61F 2/2418 623/2.14 |
| 2012/0101571 A1 | 4/2012 | Thambar et al. |
| 2012/0123529 A1 | 5/2012 | Levi et al. |
| 2012/0245673 A1 | 9/2012 | Ma et al. |
| 2012/0259409 A1 | 10/2012 | Nguyen et al. |
| 2013/0023985 A1 | 1/2013 | Khairkhahan et al. |
| 2013/0046373 A1* | 2/2013 | Cartledge ............... A61F 2/966 623/1.11 |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2013/0331931 A1 | 12/2013 | Gregg et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1* | 9/2014 | White ............... A61F 2/2418 623/23.7 |
| 2014/0296962 A1 | 10/2014 | Cartledge et al. |
| 2014/0330372 A1 | 11/2014 | Weston et al. |

(56) References Cited

U.S. PATENT DOCUMENTS

| | | |
|---|---|---|
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2017/0100236 A1 | 4/2017 | Robertson et al. |
| 2017/0128198 A1 | 5/2017 | Cartledge et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 2246526 A1 | 3/1973 |
| DE | 2246526 C3 | 7/1981 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 19546692 C2 | 11/2002 |
| DE | 10049812 B4 | 6/2004 |
| DE | 19857887 B4 | 5/2005 |
| DE | 10049815 B4 | 10/2005 |
| DE | 10049814 B4 | 10/2006 |
| EP | 0103546 A1 | 3/1984 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| FR | 2788217 A1 | 7/2000 |
| FR | 2815844 A1 | 5/2002 |
| FR | 2815844 B1 | 1/2003 |
| GB | 2056023 A | 3/1981 |
| GB | 2056023 B | 8/1983 |
| SU | 1271508 A1 | 11/1986 |
| WO | 9117720 A1 | 11/1991 |
| WO | 1991017720 A1 | 11/1991 |
| WO | 9217118 A1 | 10/1992 |
| WO | 1992017118 A1 | 10/1992 |
| WO | 9301768 A1 | 2/1993 |
| WO | 1993001768 A1 | 2/1993 |
| WO | 9724080 A1 | 7/1997 |
| WO | 1997024080 A1 | 7/1997 |
| WO | 9829057 A1 | 7/1998 |
| WO | 1998029057 A1 | 7/1998 |
| WO | 9930646 A1 | 6/1999 |
| WO | 1999030646 A1 | 6/1999 |
| WO | 9933414 A1 | 7/1999 |
| WO | 1999033414 A1 | 7/1999 |
| WO | 9940964 A1 | 8/1999 |
| WO | 1999040964 A1 | 8/1999 |
| WO | 9947075 A1 | 9/1999 |
| WO | 1999047075 A1 | 9/1999 |
| WO | 0018333 A1 | 4/2000 |
| WO | 2000018333 A1 | 4/2000 |
| WO | 0041652 A1 | 7/2000 |
| WO | 2000041652 A1 | 7/2000 |
| WO | 0047139 A1 | 8/2000 |
| WO | 2000047139 A1 | 8/2000 |
| WO | 0135878 A2 | 5/2001 |
| WO | 2001035878 A2 | 5/2001 |
| WO | 0149213 A2 | 7/2001 |
| WO | 2001049213 A2 | 7/2001 |
| WO | 0154624 A1 | 8/2001 |
| WO | 0154625 A1 | 8/2001 |
| WO | 0162189 A1 | 8/2001 |
| WO | 2001054624 A1 | 8/2001 |
| WO | 2001054625 A1 | 8/2001 |
| WO | 2001062189 A1 | 8/2001 |
| WO | 0164137 A1 | 9/2001 |
| WO | 2001064137 A1 | 9/2001 |
| WO | 0176510 A2 | 10/2001 |
| WO | 2001076510 A2 | 10/2001 |
| WO | 0222054 A1 | 3/2002 |
| WO | 2002022054 A1 | 3/2002 |
| WO | 0236048 A1 | 5/2002 |
| WO | 0241789 A2 | 5/2002 |
| WO | 2002036048 A1 | 5/2002 |
| WO | 2002041789 A2 | 5/2002 |
| WO | 0243620 A1 | 6/2002 |
| WO | 0247575 A2 | 6/2002 |
| WO | 0249540 A2 | 6/2002 |
| WO | 2002043620 A1 | 6/2002 |
| WO | 2002047575 A2 | 6/2002 |
| WO | 2002049540 A2 | 6/2002 |
| WO | 03047468 A1 | 6/2003 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013059776 A1 | 4/2013 |
| WO | 2013106585 A1 | 7/2013 |
| WO | 2015085218 A1 | 6/2015 |
| WO | 2018200531 A1 | 11/2018 |
| WO | 2018226628 A1 | 12/2018 |

OTHER PUBLICATIONS

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5): 1120-6. Epub Apr. 7, 2011

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

(56) References Cited

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Arp. 7, 2011.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

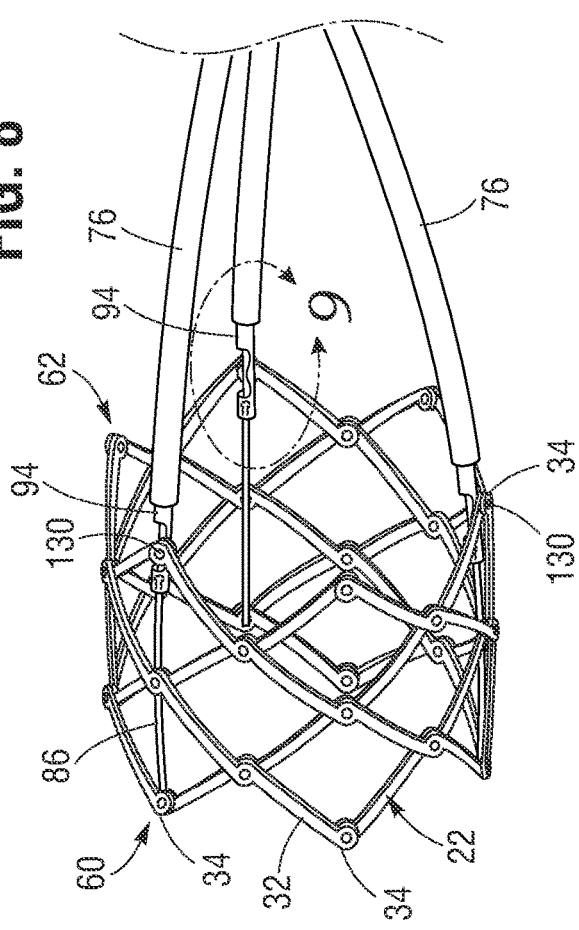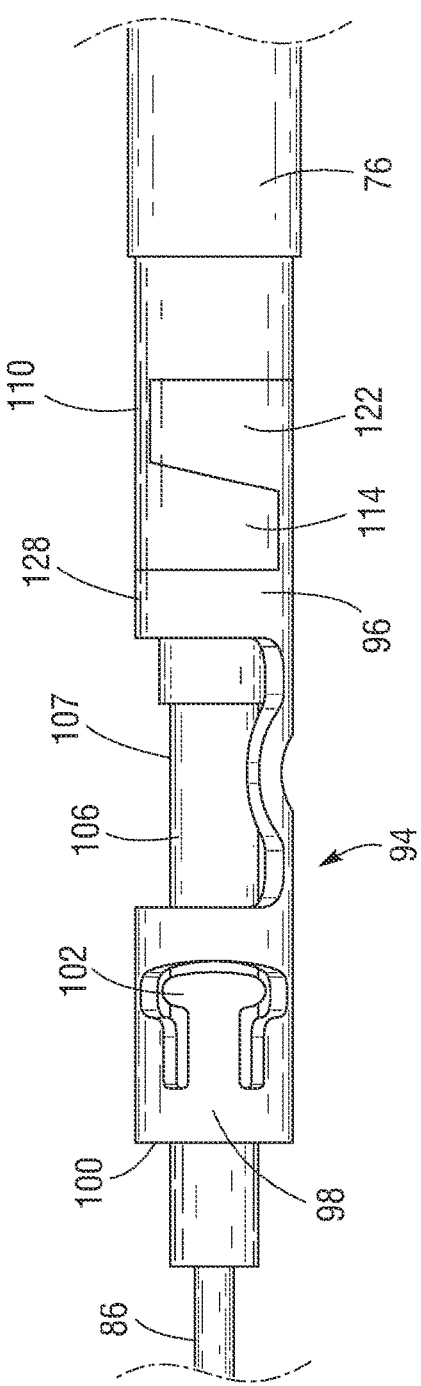

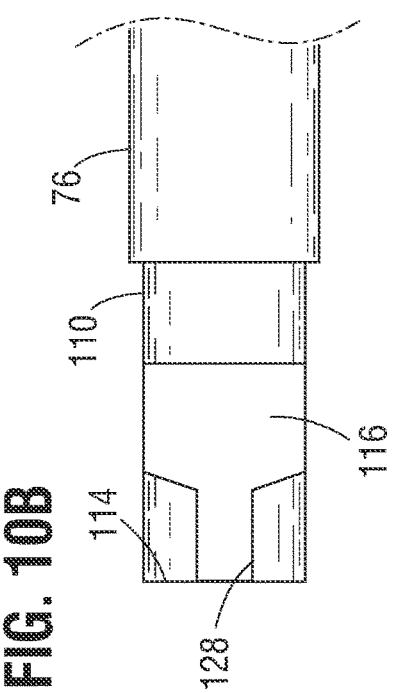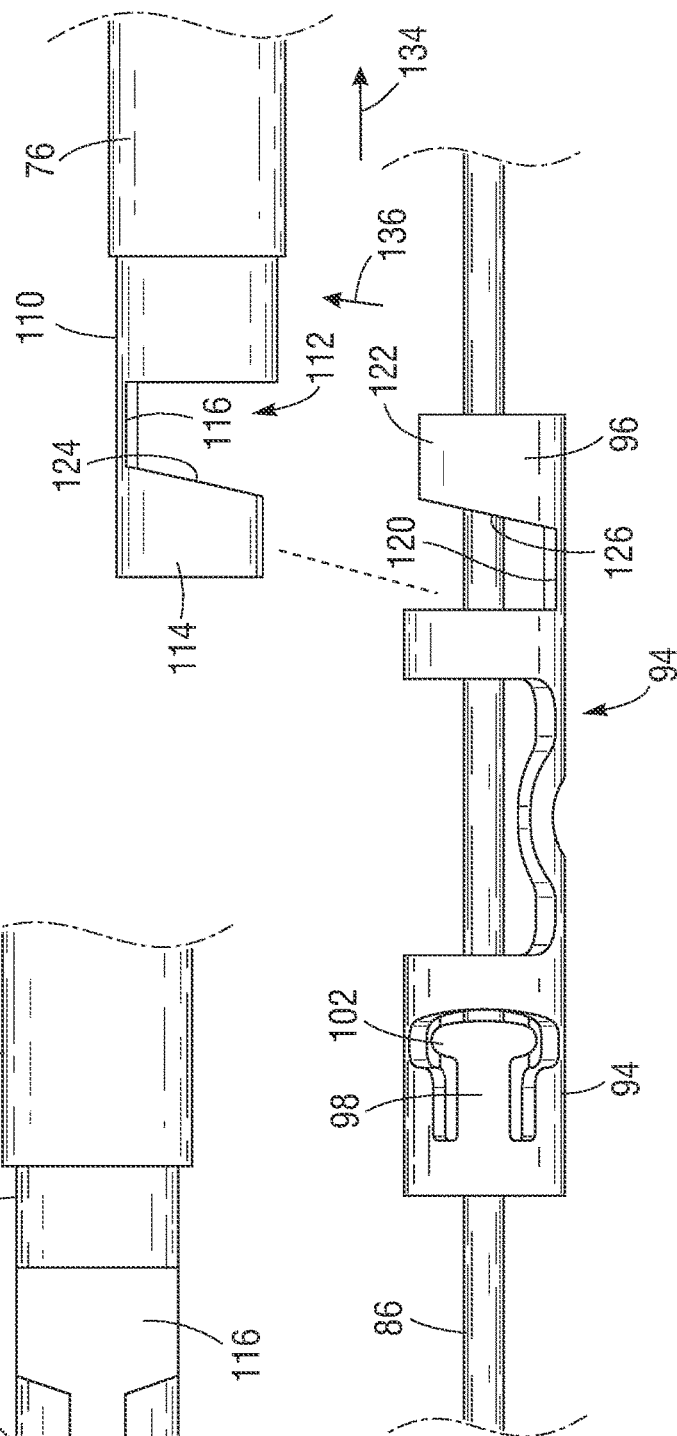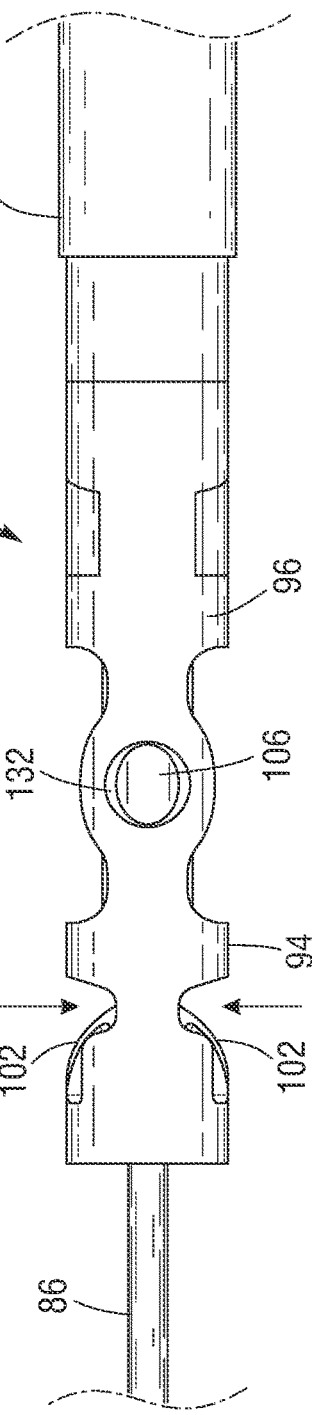

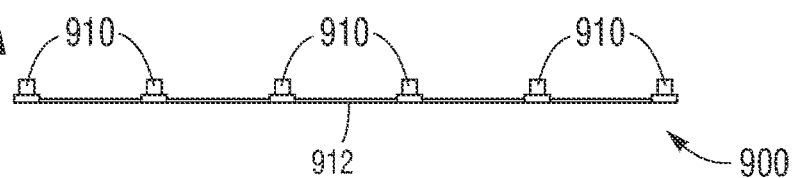
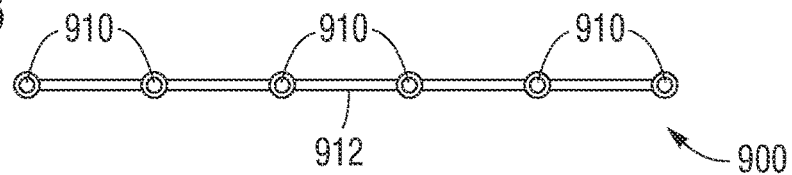
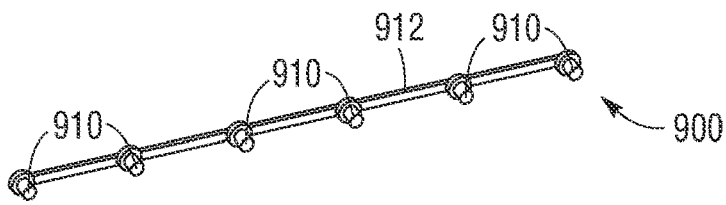
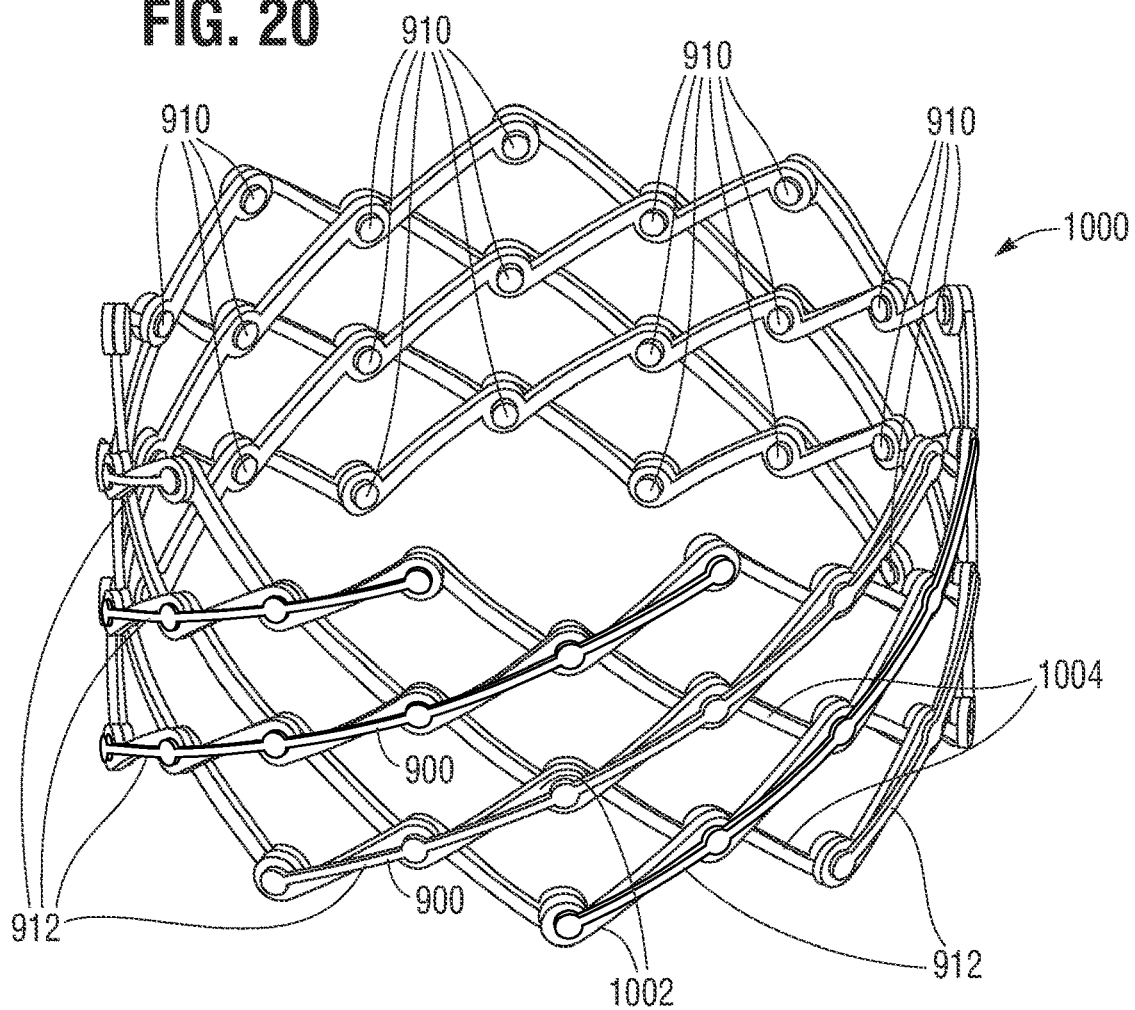

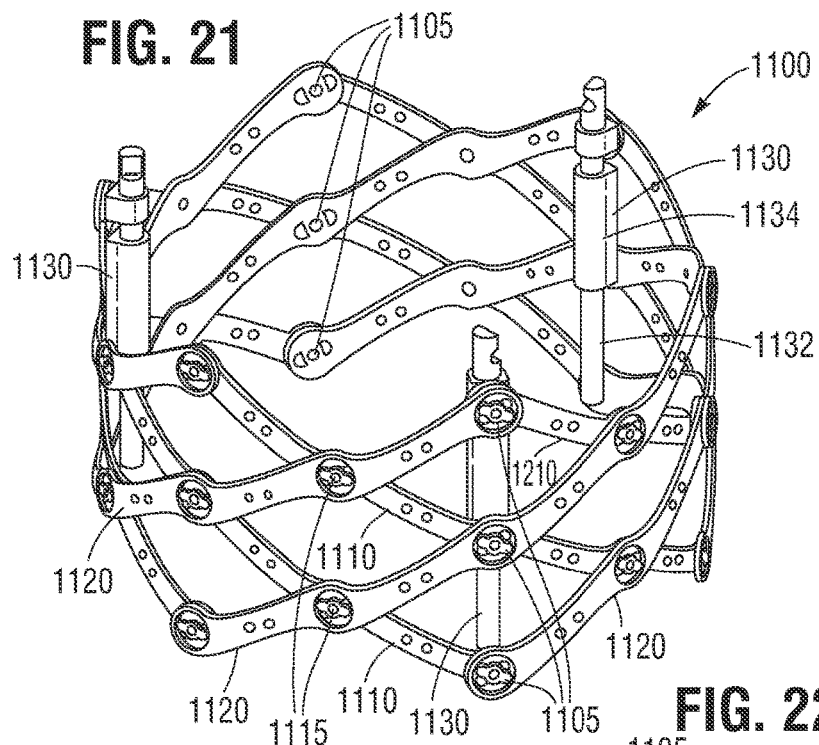
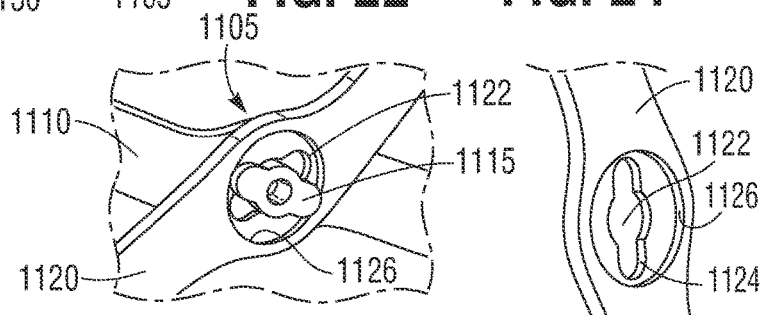
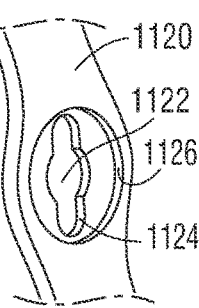
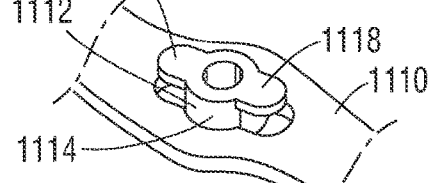
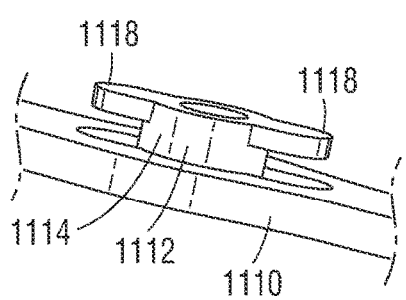
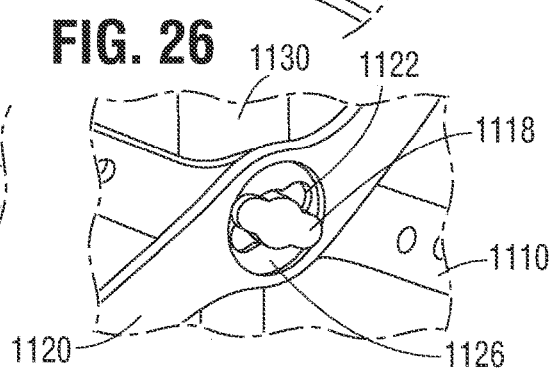

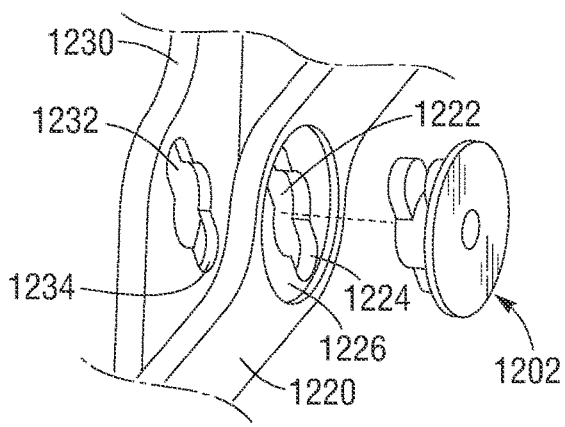
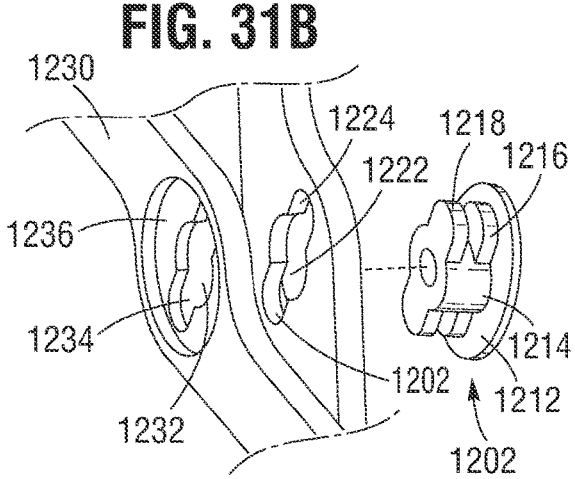
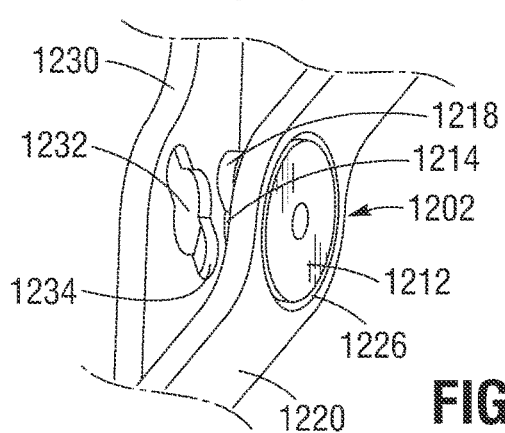
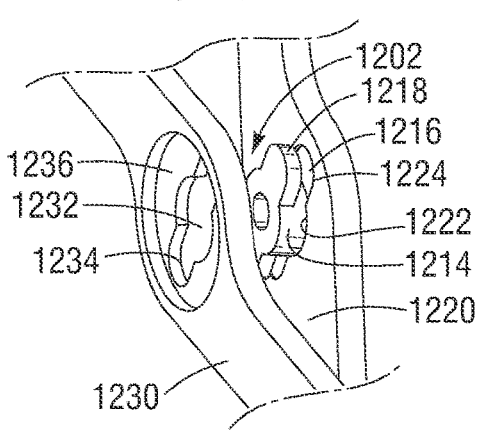
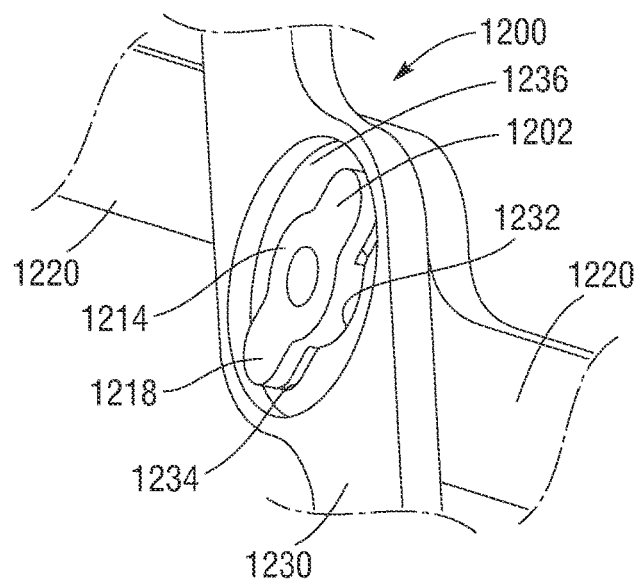

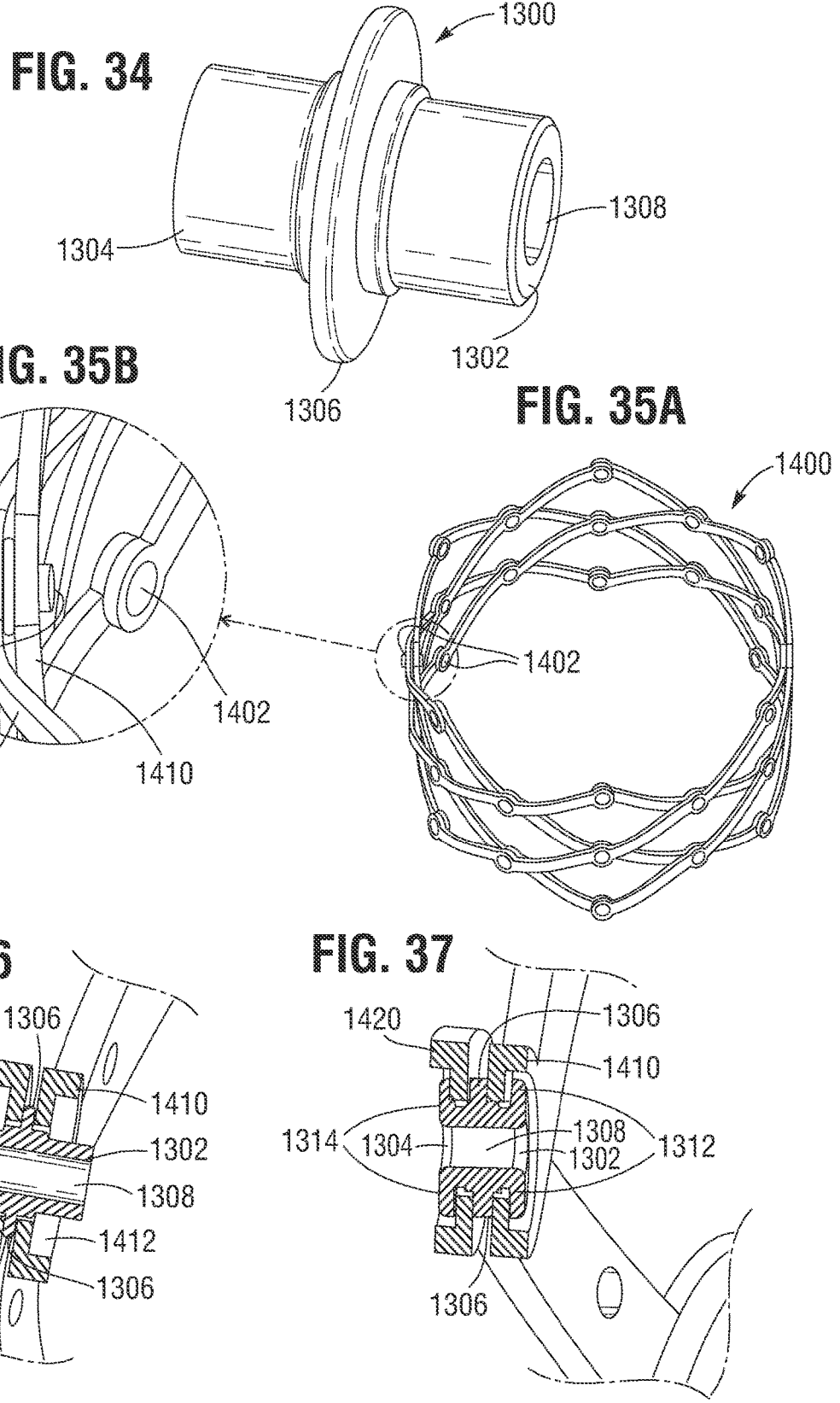

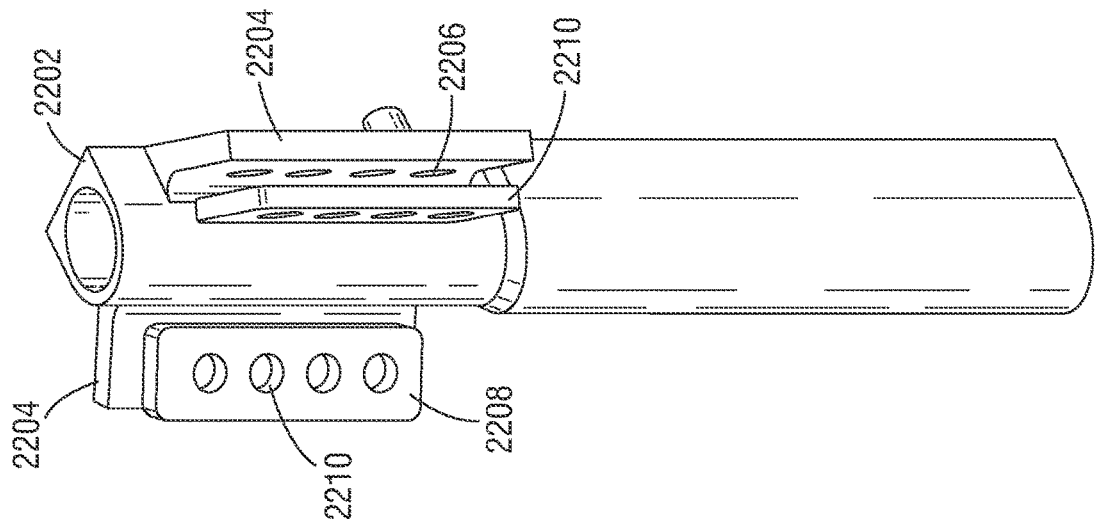
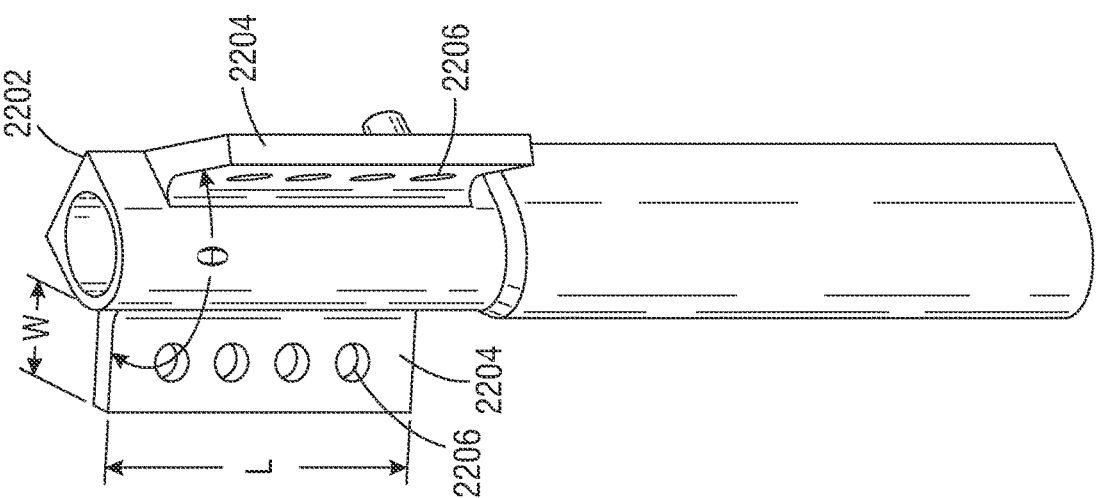

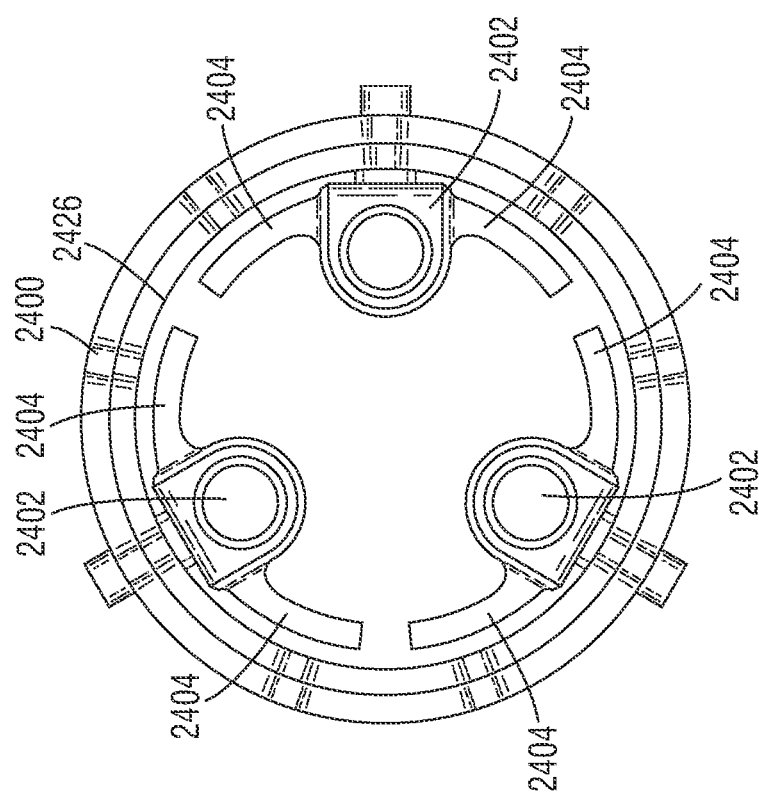
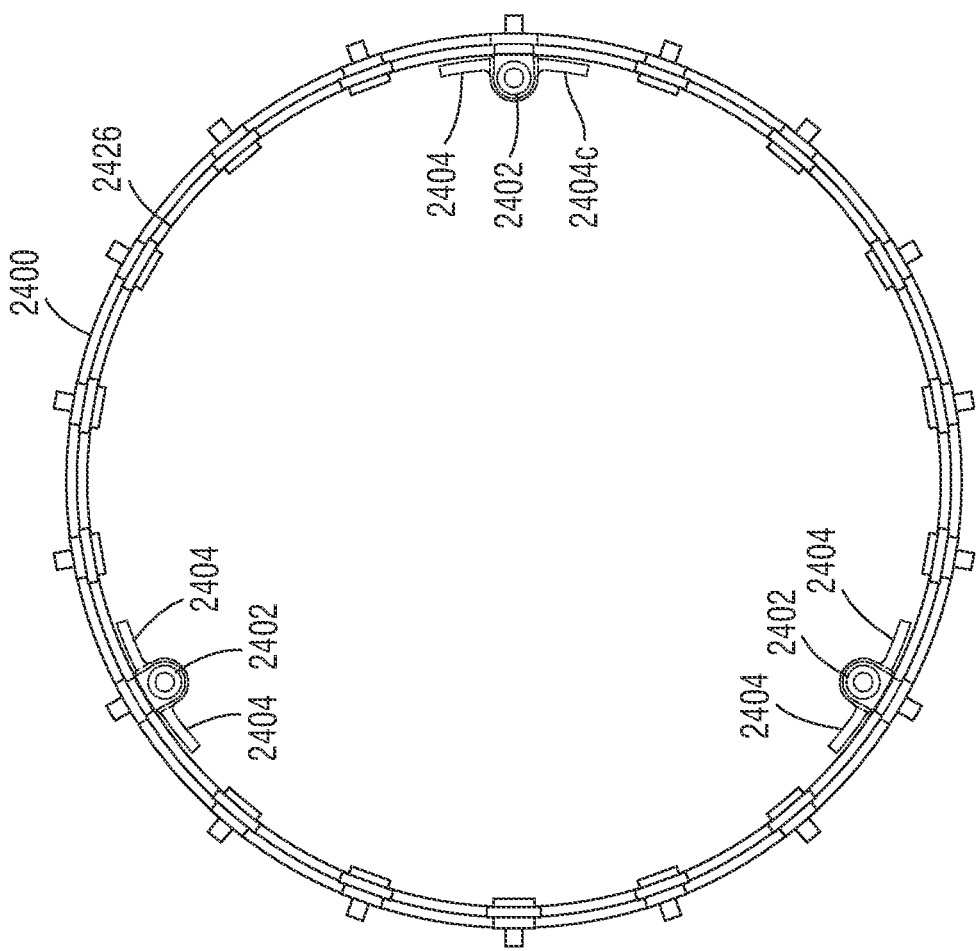

MECHANICALLY EXPANDABLE HEART VALVE

CROSS-REFERENCE TO RELATED APPLICATIONS

This application is a continuation of U.S. application Ser. No. 17/339,316, filed on Jun. 4, 2021, which is a divisional application of U.S. patent application Ser. No. 16/208,263, filed on Dec. 3, 2018, now U.S. Pat. No. 11,026,785, which is a continuation-in-part of U.S. patent application Ser. No. 15/995,528, filed on Jun. 1, 2018, now U.S. Pat. No. 10,869,759, which claims the benefit of U.S. Provisional Application Ser. No. 62/515,437, entitled "MECHANICALLY EXPANDABLE HEART VALVE", filed on Jun. 5, 2017, all of which are incorporated by reference herein.

FIELD

The present disclosure relates to implantable, mechanically expandable prosthetic devices, such as prosthetic heart valves, and to methods and assemblies for providing collapsible frames for, and including, such prosthetic devices.

BACKGROUND

Malfunctions within the human heart, such as those resulting from valvular diseases, frequently require repair of the native valve or replacement of the native valve with an artificial valve. There are a number of known repair devices (e.g., stents) and artificial valves, as well as a number of known methods of implanting these devices and valves in humans. In one known technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position by mechanical expansion or using a self-expanding frame or stent. Current frame assembly designs, however, frequently require manufacturing processes requiring handling and assembling many small parts. Improved implant frame designs and methods for assembly are needed. Such frame assemblies would preferably offer one or more of the following advantages over current approaches: minimizing the number of individual parts needed, maintaining flexibility for movement within the patient, collapsing to a low profile to minimize the size of catheter needed during introduction into the patient, and reducing the risk of rivet embolization.

SUMMARY

Embodiments of improved implantable medical devices, such as prosthetic heart valves, are disclosed herein, as well as methods for providing such devices and assemblies.

In one representative embodiment, a method of assembling an implantable medical device comprises providing a plurality of struts, each strut comprising a length and a plurality of apertures spaced apart from each other along the length. The method can further comprise providing a plurality of strut connectors comprising an elongated support member and a plurality of projections spaced apart from each other along the support member. The method can further comprise connecting the struts to each other with the strut connectors to form an annular frame, wherein the projections of each strut connector extend through respective apertures of one of the struts and into respective apertures of one or more other struts to form a plurality of pivot joints between the struts.

In some embodiments, the plurality of struts comprises a first set of inner struts and a second set of outer struts, wherein the inner struts are connected to the outer struts by the strut connectors.

In some embodiments, the strut connectors are placed against respective outer struts and each strut connector comprises at least first and second projections that extend through apertures of the same outer strut and into apertures of different inner struts.

In some embodiments, the strut connectors are placed against respective inner struts and each strut connector comprises at least first and second projections that extend through apertures of the same inner strut and into apertures of different outer struts.

In some embodiments, the method further comprises mounting a valve member comprising a plurality of leaflets inside of the annular frame.

In some embodiments, the strut connectors are formed using electrochemical machining.

In some embodiments, the strut connectors are formed using laser machining.

In another representative embodiment, an implantable medical device comprises a first set of a plurality of first struts extending in a first direction and a second set of a plurality of second struts extending in a second direction, wherein the first struts are interwoven with the second struts to form an annular frame that is radially compressible and expandable. Each first strut can be pivotally connected to at least one second strut.

In some embodiments, each first strut can comprise a plurality of projections spaced apart from each along a length of the first strut and each second strut can comprise a plurality of apertures extending along a length of the second strut, and wherein the projections of the first struts extend into respective apertures of the second struts.

In some embodiments, each first strut has at least one projection that extends radially inwardly and into an aperture of an adjacent second strut and at least one projection extends radially outwardly and into an aperture of an adjacent second strut.

In some embodiments, the projections are integrally formed on the first struts.

In some embodiments, each first strut passes radially outside of at least one second strut and radially inside of at least one second strut.

In some embodiments, the medical device further comprises a valve member which can comprise a plurality of leaflets mounted inside the annular frame.

In another representative embodiment, a method of assembling a frame for an implantable medical device comprises providing a plurality of individual struts comprising a first set of a plurality of first struts and a second set of a plurality of second struts. The method can further comprise interweaving the first struts with the second struts to form an annular frame.

In some embodiments, the individual struts, prior to the act of interweaving, are curved.

In some embodiments, the individual struts, prior to the act of interweaving, have a radius of curvature substantially the same as the radius of curvature of the annular frame formed by the struts.

In some embodiments, the individual struts are laser cut from a metal tube.

In some embodiments, each of the plurality of first struts is formed with a plurality of radially extending projections and each of the plurality of second struts is formed with a plurality of apertures.

In some embodiments the interweaving comprises connecting the first struts to the second struts by extending each of the plurality of projections through a respective one of the plurality of apertures at junctions between a first strut and a second strut.

In some embodiments, the connecting comprises pivotally connecting each of the first struts to a plurality of the second struts.

In some embodiments, the plurality of radially extending projections are formed with a plurality of projections extending radially inwardly, and a plurality of projections extending radially outwardly.

In some embodiments, the method further comprises mounting the first set of the plurality of struts at a first assembly angle, wherein each of the struts in the first set of struts comprises a plurality of the radially extending projections comprising a central protrusion with at least two ears extending outward therefrom in a plane parallel to the strut formed therein. The method can further comprise mounting the second set of the plurality of struts on the first set of struts at a second assembly angle forming a relative assembly angle between the first assembly angle and the second assembly angle. Each of the struts in the second set of struts comprises a plurality of the apertures, wherein each of the apertures comprises a central opening corresponding to the central protrusion and oblong side openings corresponding to the at least two ears. In this embodiment, the mounting forms the frame.

In certain embodiments, the method can further comprise crimping the frame to cause the at least two ears on the first set of struts to rotate away from the corresponding oblong side openings in the second set of struts. The method can further comprise securing a plurality of mechanical lockers to the frame to limit the relative movement of the first set of struts and the second set of struts to a range of relative angles that does not include the relative assembly angle.

In another representative embodiment, an implantable medical device comprises a radially expandable and compressible annular frame comprising a plurality of interconnected struts, the plurality of struts comprising a first set of a plurality of first struts and a second set of a plurality of second struts, wherein the first struts overlap adjacent second struts at junctions, and expansion or compression of the annular frame causes the first struts to pivot relative to the second struts at the junctions. Each of the first struts can comprise a plurality of pairs of radially extending, first stopper tabs spaced apart from each other along a length of the first strut, and each of the second struts can comprise a plurality of pairs of radially extending, second stopper tabs spaced apart from each other along a length of the second strut.

In particular embodiments, the first stopper tabs of each pair of tabs along the first struts extend to opposite sides of an adjacent second strut at a junction and can engage second stopper tabs of the adjacent second strut upon pivoting movement of the first struts relative to the second struts.

In some embodiments, the first stopper tabs extend radially inward and the second stopper tabs extend radially outward.

In another representative embodiment, an implantable medical device comprises a radially expandable and compressible annular frame comprising a plurality of interconnected struts, the plurality of struts comprising a first set of a plurality of first struts and a second set of a plurality of second struts, wherein the first struts overlap adjacent second struts at junctions and expansion or compression of the annular frame causes the first struts to pivot relative to the second struts at the junctions. Each of the first struts can comprise a plurality of apertures spaced apart from each other along a length of the first strut, and each of the second struts can comprise a plurality of apertures spaced apart from each other along a length of the second strut. The device can further comprise a plurality of rivets, each rivet extending through an aperture of a first strut and an aperture of an adjacent second strut at a junction, and each rivet can further comprise a first flange positioned radially outside of a corresponding first strut and a second flange positioned radially inside of a corresponding second strut.

In some embodiments, each rivet comprises a third flange intermediate the first and second flanges and positioned radially between a first strut and a second strut at a junction.

In another representative embodiment, an implantable medical device comprises a radially expandable and compressible annular frame comprising a plurality of interconnected struts, the plurality of struts comprising a first set of a plurality of first struts and a second set of a plurality of second struts, wherein the first struts overlap adjacent second struts at junctions and expansion or compression of the annular frame causes the first struts to pivot relative to the second struts at the junctions, wherein the frame comprises a plurality of hinges at the junctions extending from the first struts through corresponding non-circular apertures of the second struts at the junctions.

In some embodiments, each hinge comprise a cylindrical pivot portion that can rotate in a corresponding aperture of a second strut and a locking member extending from the pivot portion, wherein the locking member is sized and shaped relative to the corresponding aperture of the second strut so as to prevent radial separation of the first and second struts whenever the locking member is rotationally offset from the corresponding aperture upon radial expansion and compression of the frame.

In some embodiments, the second struts are formed with recessed portions surrounding the non-circular apertures and the locking members of the hinges are disposed within the recessed portions.

In some embodiments, the implantable medical device further comprises one or more actuators mounted on the frame and configured to radially expand and compress the frame between a radially compressed state defining a compressed diameter and a radially expanded state defining an expanded diameter. In particular embodiments, each locking member is rotationally offset from corresponding non-circular apertures in the second struts at the compressed diameter, the expanded diameter, and all diameters in between the compressed and expanded diameters.

In some embodiments, the hinges are integrally formed on the first struts.

In some embodiments, the hinges are separate components from the first and second struts. Each of the first struts can comprise a plurality of non-circular apertures, and each hinge extends through an aperture in a first strut and an adjacent aperture in a second strut at a junction.

In some embodiments, each of the hinges further comprises a retaining member configured to be retained within the non-circular apertures on the first struts.

In some embodiments, each of the hinges further comprises a circular base member configured to be retained within a circular recess surrounding one of the non-circular apertures on the first struts.

In some embodiments, the locking members comprise a non-circular shape.

In some embodiments, the locking members comprise a non-circular central protrusion with at least two ears extending outward therefrom in a plane parallel to the strut.

In another representative embodiment, a method of assembling an implantable medical device comprises providing a plurality of first struts and providing a plurality of second struts, each second strut comprising a plurality of non-circular apertures spaced along a length thereof. The method can further comprise connecting the first and second struts to each other to form an annular frame by inserting hinges through the non-circular apertures of the second struts, each hinge having a cylindrical pivot portion disposed in a corresponding non-circular aperture and a locking member extending from one end of the pivot portion, wherein the locking members are rotationally aligned with corresponding non-circular apertures when the hinges are inserted into the non-circular apertures.

In some embodiments, the method can further comprise pivoting the first struts relative to the second struts to cause the locking members to become rotationally offset from their corresponding non-circular apertures, and mounting one or more actuators on the frame, the one or more actuators configured to radially expand and compress the frame within a predetermined range of diameters corresponding to a predetermined range of angles between the first and second struts at which the locking members are at all times rotationally offset from the non-circular apertures.

In some embodiments, each first strut comprises a plurality of non-circular apertures spaced along a length thereof, and connecting the first and second struts further comprises inserting the hinges through the non-circular apertures of the first struts and the second struts.

In some embodiments, the hinges are integral to the first struts.

In some embodiments, the first struts are interwoven with the second struts.

In another representative embodiment, an implantable medical device comprises a radially expandable and compressible annular frame comprising an inner frame sub-assembly and an outer frame sub-assembly. Each of the frame sub-assemblies can comprise a closed annular frame comprising plurality of interconnected struts. The plurality of struts of each frame sub-assembly can comprises a first set of a plurality of first struts and a second set of a plurality of second struts, wherein the first struts overlap adjacent and are rotatably connected to second struts at junctions, and expansion or compression of the annular frame causes the first struts to pivot relative to the second struts at the junctions.

In some embodiments, each of the first struts can comprise either a plurality of projections spaced apart from each other along a length of the first strut or a plurality of apertures spaced apart from each other along a length of the first strut, and each of the second struts can comprise a plurality of apertures and a plurality of projections spaced apart from each other along a length of the second strut. At each of the junctions, either a projection on a first strut may be inserted through an aperture of an adjacent second strut, or a projection on a second strut may be inserted through an aperture of an adjacent first strut to rotatably connect the first strut to the second strut.

In particular embodiments, each of the inner frame sub-assembly and the outer frame comprises at least three inner struts and three outer struts. In particular embodiments, the outer frame assembly comprises six inner struts and six outer struts.

In some embodiments, a prosthetic valve leaflet assembly is positioned within the inner-frame sub-assembly. In particular embodiments, the prosthetic valve leaflet assembly is positioned within and secured to the inner frame sub-assembly without being secured to the outer frame sub-assembly. In more particular embodiments, the prosthetic valve leaflet assembly is positioned so that the prosthetic valve leaflets are prevented from contacting the outer frame sub-assembly when they open during the cardiac cycle, while in other embodiments such contact is minimized.

In some embodiments, a skirt is positioned on the inner frame sub-assembly. In particular embodiments, the skirt is positioned between a first set of inner struts and a second set of outer struts of the inner frame sub-assembly. In another embodiment, the skirt is positioned on the outside of the inner-frame sub-assembly and disposed between the inner frame sub-assembly and the outer frame sub-assembly.

In some embodiments, one or more actuators are positioned on the frame, the one or more actuators being configured to radially expand and compress the frame. In particular embodiments, the actuators may be configured to expand and compress the frame within a predetermined range of diameters corresponding to a predetermined range of angles between the first and second struts.

In another representative embodiment, a method of assembling an implantable medical device comprises assembling an inner frame sub-assembly comprising a plurality of first struts and a plurality of second struts. The method can further comprise connecting the first and second struts to each other to form a first closed annular inner frame sub-assembly by connecting each of the plurality of first struts to at least two of the plurality of second struts. The method can further comprise assembling an outer frame sub-assembly comprising a plurality of third struts and a plurality of fourth struts. The method can further comprise connecting the third and fourth struts to each other to form a second closed annular outer frame sub-assembly by connecting each of the plurality of third struts to at least two of the plurality of fourth struts. The method can further comprise after assembling the inner frame sub-assembly and the outer frame sub-assembly, inserting the inner frame sub-assembly inside the outer frame sub-assembly and interconnecting the two sub-assemblies at a plurality of junctions along the struts forming a single, closed annular frame assembly.

In some embodiments, the method can further comprise assembling a leaflet assembly on the inner frame sub-assembly. In particular embodiments, the leaflet assembly is assembled on the inner frame sub-assembly without contacting the outer frame sub-assembly. In some embodiments, a skirt is positioned on the inner frame sub-assembly. In particular embodiments, the skirt is positioned between a first set of inner struts and a second set of outer struts of the inner frame sub-assembly. In another particular embodiment, the skirt is positioned on the outside of the inner-frame sub-assembly and disposed between the inner frame sub-assembly and the outer frame sub-assembly. In another particular embodiment, the skirt is positioned along with a leaflet assembly on the inside of the inner frame sub-assembly.

In some embodiments, the inner frame sub-assembly and the outer frame-sub-assembly are rotatably interconnected at junctions along the struts via a plurality of hinge members. The hinge members can comprises, for example, rivets, pins, integral projections, or similar mechanisms. In particular embodiments, the hinge members may pass through two or more of the inner frame sub-assembly, the skirt, and the outer frame sub-assembly. In particular embodiments, the rivets or other projections may pass through three or more of the prosthetic valve sub-assembly, inner frame sub-assembly, inner skirt, and outer frame sub-assembly. In particular embodiments an outer skirt may be attached to the outer frame sub-assembly.

In another representative embodiment, a prosthetic valve assembly can include an annular frame being radially expandable and compressible between a radially compressed configuration and a radially expanded configuration, and a valvular structure comprising a plurality of leaflets mounted inside the annular frame. Each two adjacent leaflets can form a pair of commissure tabs. The prosthetic valve can further include a plurality of posts mounted on an interior surface of the annular frame, and a pair of commissure attachment members extending outwardly from each post and away from each other. A tangent line that is tangent to a circumference of the frame at the post can form an acute angle relative to each corresponding commissure attachment member. Each pair of commissure tabs can be respectively attached to a corresponding pair of the commissure attachment members.

In some embodiments, each post can comprise a component of an actuator configured to radially expand and compress the annular frame.

In some embodiments, the acute angle can be between about 15 degrees and about 45 degrees.

In some embodiments, the acute angle can be about 30 degrees.

In some embodiments, each commissure attachment member can extend from a respective post in a generally circumferential direction when the frame is in the radially expanded configuration, and the commissure attachment member can be configured to resiliently fold inwardly as the frame is compressed to the radially compressed configuration.

In some embodiments, each commissure attachment member can be spaced apart from an adjacent commissure attachment member of an adjacent actuator when the frame is in the radially compressed configuration.

In some embodiments, each commissure attachment member can comprise a plurality of apertures and a corresponding commissure tab is sutured to the commissure attachment member with sutures extending through the plurality of apertures.

In some embodiments, the prosthetic valve can further comprise a plurality of reinforcement members, each of which can be configured to be positioned radially inwardly from a corresponding commissure attachment member. Each commissure tab can be secured between a corresponding pair of a reinforcement member and a commissure attachment member.

In some embodiments, each reinforcement member can have a plurality of apertures and a corresponding commissure tab is sutured to the reinforcement member with sutures extending through the plurality of apertures.

In another representative embodiment, a prosthetic valve assembly can comprise an annular frame being radially expandable and compressible between a radially compressed configuration and a radially expanded configuration, and a valvular structure comprising a plurality of leaflets mounted inside the annular frame. Each two adjacent leaflets can form a commissure. The prosthetic valve can further comprise a plurality of posts mounted on the annular frame, and at least one commissure attachment member extending outwardly from each post. The commissure attachment member can form an acute angle relative to a tangent line that is tangent to a circumference of the frame at the post. Each commissure can be attached to respective commissure attachment member.

In some embodiments, each post can comprise an outer member of an actuator. The actuator can include an inner member received at least partially within the outer member. Axial movement of the inner member relative to the outer member can cause radial expansion or compression the annular frame.

In some embodiments, each commissure attachment member can extend from a respective post in a generally circumferential direction when the frame is in the radially expanded configuration, and the commissure attachment member can be configured to resiliently fold inwardly as the frame is compressed to the radially compressed configuration.

In some embodiments, each commissure attachment member can comprise a plurality of apertures and a corresponding commissure tab can be sutured to the commissure attachment member with sutures extending through the plurality of apertures.

In some embodiments, the assembly can further comprise a plurality of reinforcement members, each of which is configured to be positioned radially inwardly from a corresponding commissure attachment member. Each commissure tab can be secured between a corresponding pair of a reinforcement member and a commissure attachment member.

In some embodiments, for each post, the at least one commissure attachment member can include a first commissure attachment member, and a second commissure attachment member which can extend outwardly from the post and away from each other such that the first and second commissure attachment members form a pair that are symmetrical relative to a radial axis passing through the post. Each commissure can comprise a pair of commissure tabs, and each pair of commissure tabs can be respectively attached to corresponding pair of first and second commissure attachment members.

In another representative embodiment, a prosthetic valve assembly can include an annular frame, a plurality of actuators mounted on the annular frame and configured to radially expand and compress the annular frame between a radially compressed configuration and a radially expanded configuration, and a valvular structure comprising a plurality of leaflets mounted inside the annular frame. Each two adjacent leaflets can form a pair of commissure tabs. The prosthetic valve assembly can further include a pair of commissure attachment members extending outwardly from each actuator and away from each other. Each commissure attachment member can be angled inwardly relative to an interior surface of the frame at the actuator and points away from a central longitudinal axis of the frame. Each pair of commissure tabs can be attached to a corresponding pair of the commissure attachment members.

In some embodiments, each commissure attachment member can form an acute angle relative to a line that is tangent to a circumference of the frame at a corresponding actuator.

In some embodiments, each commissure attachment member can generally conform to a curvature of the interior surface of the frame when the frame is in the radially compressed configuration.

In some embodiments, each commissure attachment member can comprise a plurality of apertures and a corresponding commissure tab can be sutured to the commissure attachment member with sutures extending through the plurality of apertures.

In some embodiments, the assembly can further comprise a plurality of reinforcement members, each of which is configured to be positioned radially inwardly of a corresponding commissure attachment member. Each commissure tab can be secured between a corresponding pair of a reinforcement member and a commissure attachment member.

In another representative embodiment, an implantable medical device can comprise a radially expandable and compressible annular frame comprising a plurality of interconnected struts. The plurality of struts can comprise a plurality of first struts and a plurality of second struts. The first struts can overlap adjacent second struts at junctions. Radial expansion or compression of the annular frame can cause the first struts to pivot relative to the second struts at the junctions. The frame can comprise a plurality of hinges at the junctions extending from the first struts through corresponding apertures of the second struts at the junctions. The hinges can be integrally formed on the first struts. The first struts can have a larger plastic deformation range than the second struts.

In some embodiments, the first struts and the second struts can comprise the same material. The material can be less annealed in the second struts than the first struts.

In some embodiments, the material can be nickel-cobalt-chromium alloy.

In some embodiments, the first struts can comprise a first material and the second struts can comprise a second material. The first material can be more plastically deformable than the second material.

In some embodiments, the first material can comprise stainless steel, and the second material can comprise nickel-cobalt-chromium alloy.

In another representative embodiment, a method can include annealing a plurality of first struts for a first duration, annealing a plurality of second struts for a second duration such that the first struts have a larger plastic deformation range than the second struts, and assembling the plurality of first struts with the plurality of second struts into an annular frame such that the first struts overlap adjacent second struts at junctions and radial expansion or compression of the annular frame causes the first struts to pivot relative to the second struts at the junctions.

In some embodiments, a plurality of projections can be integrally formed on the first struts and assembling the plurality of first struts with the plurality of second struts can include inserting the projections through corresponding apertures in the second struts to form hinges at the junctions.

In some embodiments, the method can further include plastically deforming end portions of the projections to secure the first struts to the second struts.

In some embodiments, the act of annealing the plurality of first struts can include heating the first struts to a first annealing temperature for a first duration, and the act of annealing the plurality of second struts can include heating the second struts to a second annealing temperature for a second duration.

In some embodiments, the first annealing temperature is about the same as the second annealing temperature. The first duration can be longer than the second duration.

In some embodiments, the first and second struts can comprise MP35N. The first and second annealing temperatures can be between about 1010-1180° C. The first duration can be between about 5-10 minutes and the second duration can be about half of the first duration.

The foregoing and other objects, features, and advantages of the invention will become more apparent from the following detailed description, which proceeds with reference to the accompanying figures.

BRIEF DESCRIPTION OF THE DRAWINGS

FIG. 8 is an enlarged perspective view of the distal end portion of the prosthetic valve delivery assembly of FIG. 1.

FIG. 9 is an enlarged side view of a locking unit and the distal end portion of a positioning member of the prosthetic valve delivery assembly of FIG. 1.

FIG. 10A is an enlarged side view of the locking and the positioning member of FIG. 9, illustrating the positioning member decoupled from the locking unit.

FIG. 10B is enlarged side view of the distal end portion of the positioning member of FIG. 10A rotated 90 degrees from the orientation shown in FIG. 10A.

FIG. 11 is an enlarged side view of the locking unit and the positioning member of FIG. 9 rotated 90 degrees from the orientation shown in FIG. 9.

FIG. 19A is a side view of an embodiment of a strut connector that can be used to form multiple hinge connections between struts of a frame.

FIG. 19B is a plan view of the strut connector of FIG. 19A.

FIG. 19C is a perspective view of the strut connector of FIG. 19A.

FIG. 20 is a perspective view of an embodiment of a frame comprising a plurality of struts pivotally secured using a plurality of the strut connectors shown in FIGS. 19A-C.

FIG. 21 is a perspective view of an alternative embodiment of a frame connected using integral hinges and corresponding slots.

FIG. 22 is an enlarged, perspective view of one of the hinges formed by two overlapping struts of the frame of FIG. 21.

FIG. 23 is an enlarged, perspective view of a portion of one of the struts shown in FIG. 22.

FIG. 24 is an enlarged, perspective view of a portion of the other strut shown in FIG. 22.

FIG. 25 is another perspective view of the strut shown in FIG. 23 as viewed from the side of the strut.

FIG. 26 is an enlarged, perspective view of another hinge of the frame of FIG. 21, showing an end portion of an actuator pivotally connected to the hinge.

FIG. 31A is a first perspective view of the components of the hinge assembly of FIG. 29 prior to assembly.

FIG. 31B is a second perspective view of the components of the hinge assembly of FIG. 29 prior to assembly.

FIG. 32A is a first perspective view of the components of the hinge assembly of FIG. 29, with the hinge member inserted through the first strut.

FIG. 32B is a second perspective view of the components of the hinge assembly of FIG. 29, with the hinge member inserted through the first strut.

FIG. 33 is a perspective view of the components of the hinge assembly of FIG. 29, with the hinge member inserted through both struts in an assembly configuration.

FIG. 34 is a perspective view of a flanged rivet that can be used to form a hinge connection between struts of a frame.

FIG. 35A is a perspective view of an embodiment of a frame comprising a plurality of struts pivotally secured using a plurality of the flanged rivets shown in FIG. 34.

FIG. 35B is an enlarged, perspective view of one of the hinges formed by two overlapping struts of the frame of FIG. 35A using the flanged rivet of FIG. 34.

FIG. 36 is a cross-sectional view of the hinge of FIG. 35B.

FIG. 37 is a cross-sectional view of the hinge of FIG. 35B, with the ends of the flanged rivet flared out.

FIG. 53 is a perspective view of a post having a pair of commissure attachment members, according to one embodiment.

FIG. 54 is a perspective view of the post depicted in FIG. 53 and a pair of reinforcement members corresponding to the pair of commissure attachment members.

FIG. 63 is a top plan view of a frame in a radially expanded configuration, where the commissure attachment members have a curved shape.

FIG. 64 is a top plan view of the frame depicted in FIG. 63 in a radially compressed configuration.

DETAILED DESCRIPTION

Described herein are examples of prosthetic implant delivery assemblies and components thereof which can improve a physician's ability to control the size of a mechanically-expandable prosthetic implant, such as prosthetic valves (e.g., prosthetic heart valves or venous valves), stents, or grafts, as well as facilitate separation of the prosthetic implant from the delivery assembly, during the implantation procedure. The present disclosure also provides frames for use with such prosthetic implants. The frames can comprise struts shaped to reduce or eliminate pinching of the soft components of the prosthetic implant (e.g., leaflets of the implant) when the implant is radially compressed to a delivery configuration for delivery into a patient.

Figure 1:
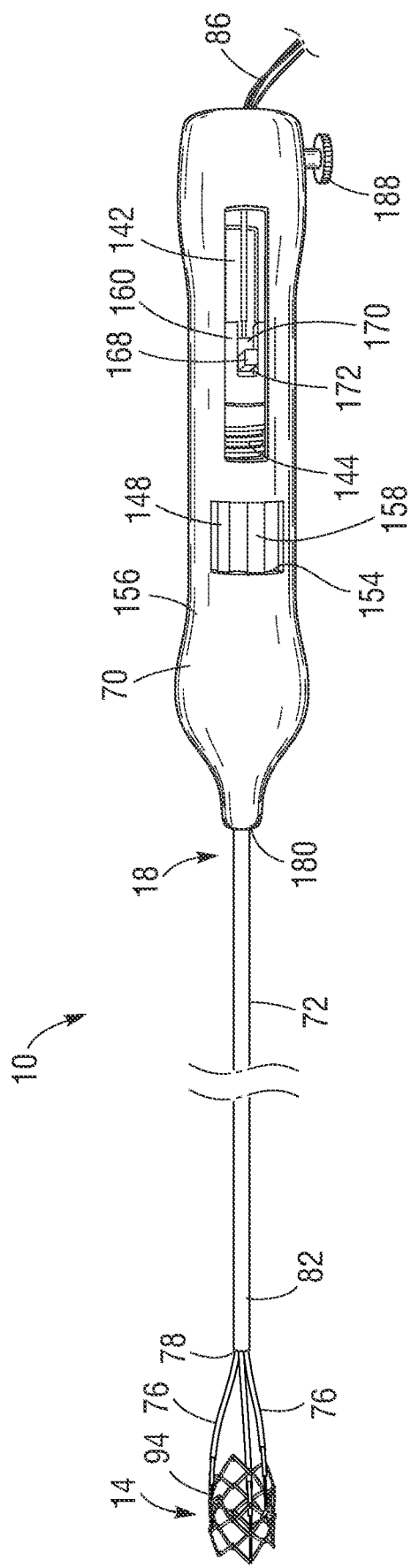
FIG. 1 is a side elevation view of an embodiment of a prosthetic valve delivery assembly.

FIG. 1 shows one example of a prosthetic implant delivery assembly 10 which may be used with one or more of the embodiments of the present disclosure. The delivery assembly 10 can include two main components: a prosthetic heart valve 14 and a delivery apparatus 18. The prosthetic valve 14 can be releasably coupled to the delivery apparatus 18, as further described below. It should be understood that the delivery apparatus 18 and other delivery apparatuses disclosed herein can be used to implant prosthetic devices other than prosthetic valves, such as stents or grafts.

Figure 2:
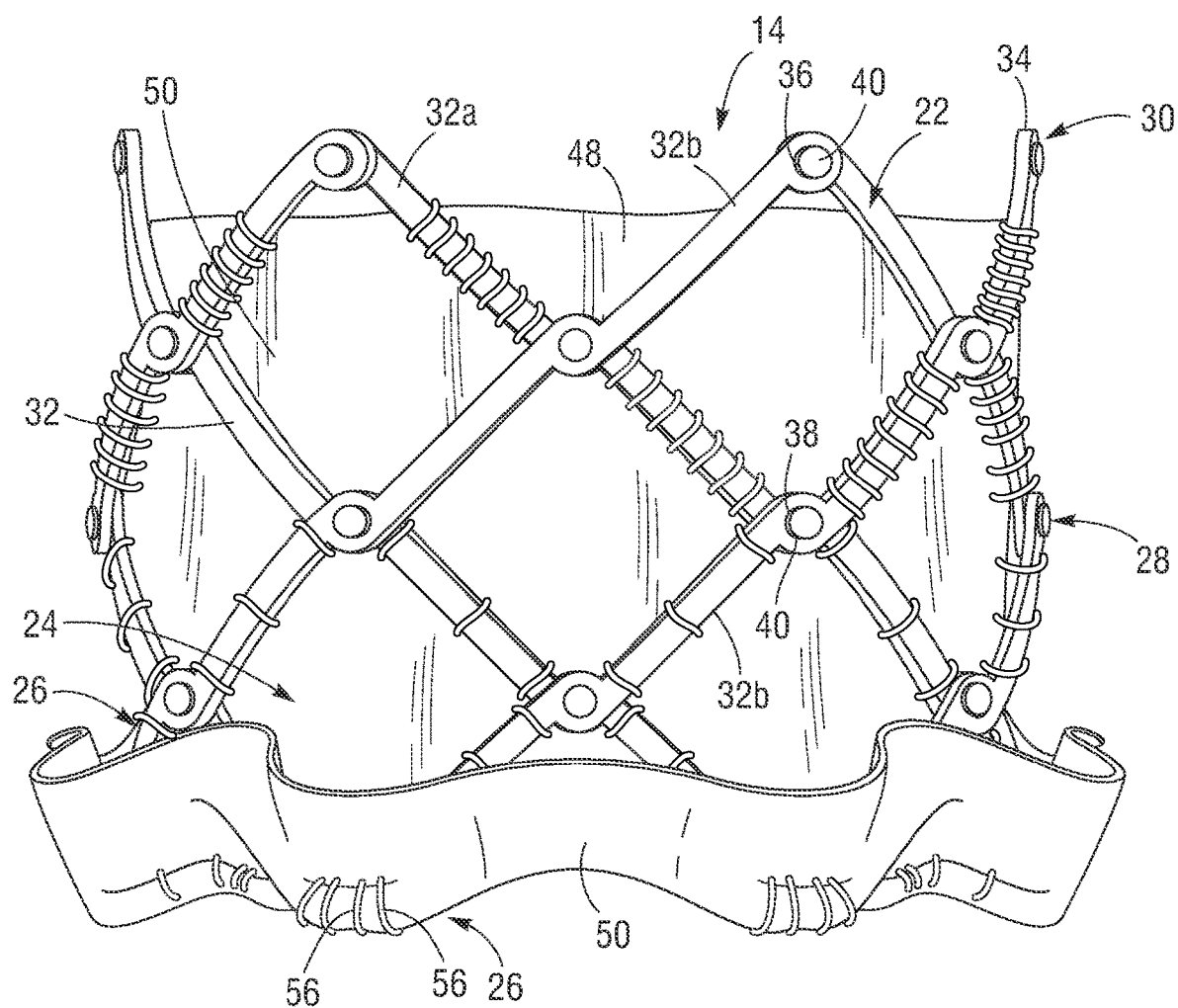
FIG. 2 is a side elevational view of a prosthetic valve, according to one embodiment.

FIG. 2 is a side elevational view of the prosthetic valve 14 shown in its deployed, radially expanded configuration. While only one side of the prosthetic valve 14 is shown in the drawings, it should be appreciated that the opposite side is similar to the portion shown. The prosthetic valve 14 can include an annular stent or frame 22, and a valve structure 24 which can be coupled to the frame 22. The frame 22 can have an inflow end portion 26, an intermediate portion 28, and an outflow end portion 30. The prosthetic valve 14 can define a longitudinal axis extending through the inflow end portion 26 and the outflow end portion 30.

The frame 22 can be made of any of various suitable materials, such as stainless steel or a nickel titanium alloy ("NiTi"), for example Nitinol, or CoCr alloys, as well. The frame 22 can include a plurality of interconnected lattice struts 32 arranged in a lattice-type pattern and forming a plurality of apices 34 at the outflow end 30 of the prosthetic valve 14. The struts 32 can also form similar apices at the inflow end of the prosthetic valve (which are covered by a skirt 50 in FIG. 2). The lattice struts 32 are shown as positioned diagonally, or offset at an angle relative to, and radially offset from, the longitudinal axis of the prosthetic valve. In other implementations, the lattice struts 32 can be offset by a different amount than depicted in FIG. 2, or some or all of the lattice struts 32 can be positioned parallel to the longitudinal axis of the prosthetic valve 14. The lattice struts 32 can comprise a set of inner struts 32a (extending from the upper left to the lower right of the frame in FIG. 2) and a set of outer struts 32b (extending from the lower left to the upper right of the frame in FIG. 2) connected to the inner struts 32a.

The lattice struts 32 can be pivotably coupled to one another. In the illustrated embodiment, for example, the end portions of the struts 32 forming the apices 34 at the outflow end 30 and at the inflow end 26 of the frame 22 can have a respective opening 36. The struts 32 also can be formed with apertures 38 spaced apart along their lengths between the opposite ends of the struts. Respective hinges can be formed at the apices 34 and at the locations where struts 32 overlap each other between the ends of the frame via fasteners 40, which can comprise individual rivets or pins that extend through the apertures 36, 38. The hinges can allow the struts 32 to pivot relative to one another as the frame 22 is expanded or contracted, such as during assembly, preparation, or implantation of the prosthetic valve 14. For example, the frame 22 (and thus the prosthetic valve 14) can be manipulated into a radially compressed or contracted configuration (see, e.g., FIGS. 6 and 7) and inserted into a patient for implantation. Once inside the body, the prosthetic valve 14 can be manipulated into an expanded state (e.g., FIGS. 2 and 4) and then released from the delivery apparatus 18 (e.g., FIG. 1), as further described below.

The frame 22 can be formed using any suitable technique. Suitable techniques include separately forming individual components (e.g., the struts 32 and fasteners 40) of the frame and then mechanically assembling and connecting the individual components to form the frame 22. The struts and fasteners can be formed, for example, by laser cutting those components from sheets or tubes of metal, or by electroforming (electroplating or electrodeposition) or physical vapor deposition, or by electro chemical machining and/or chemical etching.

In some embodiments, electroforming or physical vapor deposition or machining (e.g., laser cutting) can be used to form subcomponents of the frame 22 or the entire frame 22 with pivotable connections between the struts. In one implementation, for example, electroforming, physical vapor deposition, machining or other suitable techniques can be used to form struts 32 having integral fasteners 40. As used herein, two or more components being "integral" or "integrally formed" or "unitarily constructed" with each other means that the two or more components comprise a unitary or one-piece monolithic construction that does not include any welds, fasteners, adhesives or other means for securing separately formed pieces of material to each other. Further, the terms "integral" or "integrally formed" or "unitary construction" refers to a construction of two or more components of an article that does not include any seams between the two or more components of the article. For example, a strut 32 having integral fasteners 40 means that the strut 32 and fasteners 40 have a unitary or one-piece monolithic construction and the individual fasteners 40 are not secured to the strut 32 with any welds, fasteners, adhesives or other means.

The individual struts can be assembled together into a frame by inserting the integral fasteners 40 of each strut through a corresponding aperture of an adjacent strut. In some embodiments, electroforming, physical vapor deposition, machining or other suitable techniques can be used to form the entire frame in its final, cylindrical, or tubular shape. While in the illustrated embodiments, the frame 22 is shown as generally cylindrical in shape, other frame shapes may be used, such as, e.g., conical, hour-glass or barrel shaped. In other embodiments, electroforming, physical vapor deposition, machining or other suitable techniques can be used to form the entire frame in a flattened configuration, after which the ends of the flattened frame are connected to each other to form the final tubular shape of the frame. Frames formed from struts having integral fasteners are further described in detail below.

Figure 65:
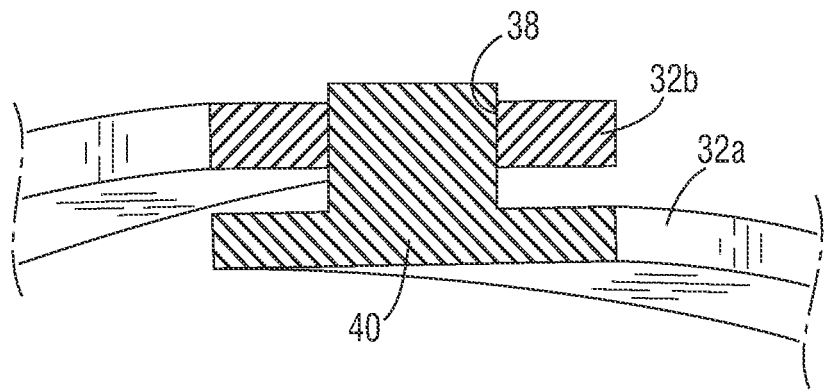
FIG. 65 shows a cross-section of a portion of two overlapping struts of a frame where an integral fastener on an inner strut is inserted through an aperture of a corresponding outer strut.
Figure 66:
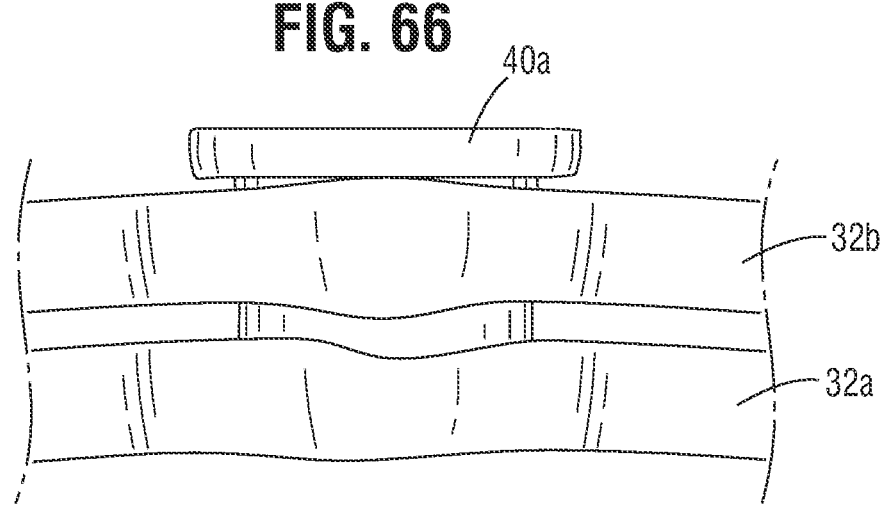
FIG. 66 shows the integral fastener depicted in FIG. 65 plastically deformed so as to create a hinge between the inner strut and the outer strut.

In some embodiments, the inner struts 32a and the outer struts 32b can have different material properties. For example, when the fasteners 40 are formed integrally with the inner struts 32a, the inner struts 32a are desired to have higher plasticity so that the integral fasteners 40 can be plastically deformed during assembly by applying an external crash force to create the required rivets or hinges between the inner struts 32a and the outer struts 32b. For example, as illustrated in FIGS. 65-66, after the fastener 40 of an inner strut 32a is inserted through a respective aperture 38 of an outer strut 32b (e.g., FIG. 65), the outer end of the fastener 40 can be plastically deformed to form a widened end portion 40a that is larger in diameter than the diameter of the corresponding aperture 38 (e.g., FIG. 66). Once formed, the widened end portion 40a prevents separation of the inner and outer struts 32a, 32b at that hinge.

Lack of plasticity may require higher forces to deform the integral fasteners 40, potentially causing material pilling and undesirable burrs in the fasteners 40. On the other hand, the outer struts 32b are desired to have lower plasticity and greater elasticity so as to impart a certain degree of resiliency (referred to as "spring effect") and shape stability to the frame 22. Thus, to provide the fasteners 40 with sufficient plasticity and maintain a desired spring effect and shape stability of the frame 22, the inner struts 32a (including the integral fasteners 40 located on the inner struts 32a) can be configured to have a larger plastic deformation range than the outer struts 32b.

In one embodiment, the inner struts 32a and the outer struts 32b can comprise the same material, such as a nickel-cobalt-chromium alloy (e.g., MP35N alloy). The outer struts 32b can be less annealed than the inner struts 32a (and the integral fasteners 40) so as to form inner struts 32a that have greater plasticity than the outer struts 32b and outer struts that have greater elasticity than the inner struts. Annealing of a material can be achieved by heating the material to its annealing temperature for a predetermined duration. For example, when annealing a strut formed from a nickel-cobalt-chromium alloy (e.g., MP35N alloy), struts can be heated to a temperature in the range of about 1010-1180° C. (typically in a protective or neutral atmosphere) for several minutes (e.g., 1-10 minutes). The inner struts can be more annealed than the outer struts by annealing the inner struts for a longer period of time than the outer struts or by not annealing the outer struts.

In one embodiment, the inner struts 32a are made of a nickel-cobalt-chromium alloy (e.g., MP35N) and can be fully annealed by heating them to a temperature in the range of about 1010-1180° C. for about 5-10 minutes, whereas the outer struts 32b are made of the same material and can be less annealed by heating them to a temperature in the range of about 1010-1180° C. for a shorter duration, such as between about 4-5 minutes, or about 3-4 minutes, or about 2-3 minutes, or about 1-2 minutes.

In another embodiment, in lieu or in addition to subjecting the inner struts to more annealing than the outer struts (or not subjecting the outer struts to any annealing), the inner struts 32a and the outer struts 32b can be formed from different materials with different degrees of elasticity and/or plasticity so that the inner struts 32a (including the integral fasteners 40) are more plastically deformable than the outer struts 32b and/or the outer struts are more elastic than the inner struts. For example, the inner struts 32a (and the integral fasteners 40) can comprise stainless steel (e.g., 316L stainless steel), and the outer struts 32b can comprise a CoCr alloy (e.g., MP35N alloy).

It should be noted the outer struts 32b can be formed to have greater plasticity than the inner struts 32a if the fasteners 40 are formed integrally with the outer struts instead of the inner struts. Thus, in such embodiments, the description above for forming the inner and outer struts can be the same except that the outer struts can be more annealed than the inner struts. Additionally, in lieu of or in addition to subjecting the outer struts to more annealing than the inner struts (or not subjecting the inner struts to any annealing), the outer struts can be formed from a material that has greater plasticity than the inner struts and/or the inner struts are more elastic than the outer struts. For example, the outer struts 32b (and the integral fasteners 40) can comprise stainless steel (e.g., 316L stainless steel), and the inner struts 32a can comprise a nickel-cobalt-chromium alloy (e.g., MP35N alloy).

In other embodiments, the lattice struts 32 are not coupled to each other with respective hinges (e.g., fasteners 40) but are otherwise pivotable or bendable relative to each other to permit radial expansion and contraction of the frame. For example, the frame 22 can be formed (e.g., via laser cutting, electroforming or physical vapor deposition) from a single piece of material (e.g., a metal tube).

In addition to the lattice struts 32, the frame 22 can include one or more longitudinally extending support struts 42. The support struts 42 can be circumferentially spaced about the frame 22 and coupled, including being pivotably coupled, to the lattice struts 32. The support struts 42 can be positioned parallel to, and radially spaced apart from, the longitudinal axis of the prosthetic valve. The support struts 42 can enhance the rigidity to the frame 22 and help the frame 22 maintain a uniform shape as it is expanded or contracted. In some implementations, the frame 22 does not include the support struts 42. The support struts 42 can be connected to the lattice struts 32 at the hinge joints formed by fasteners 40 that can extend through respective apertures in the lattice struts and the support struts.

Figure 3A:
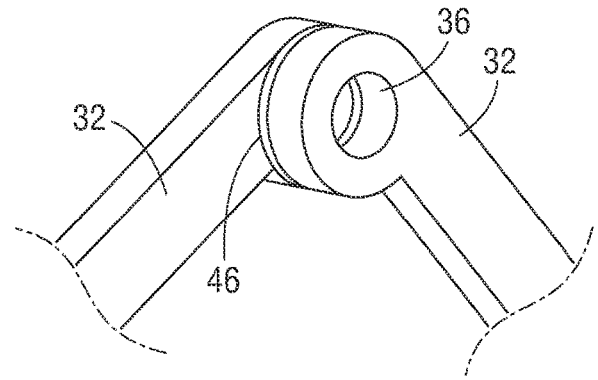
FIGS. 3A and 3B are enlarged perspective views and side views, respectively, of an embodiment of coupled frame struts useable in the prosthetic valve of FIG. 2.
Figure 3B:
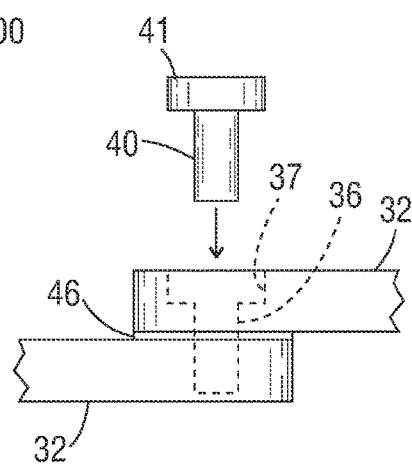

With reference to FIGS. 3A and 3B, a spacer 46, such as a washer or bushing, can be disposed in a joint between lattice struts 32, or a joint between lattice struts 32 and support struts 42 (not shown). When the lattice struts 32 and/or support struts 42 are pivotably coupled to one another, the spacers 46 can assist the lattice struts 32, or lattice struts 32 and support struts 42, in moving relative to one another. The spacer 46 can also act to space the lattice struts 32 from one another, or from the support struts 42. In some implementations, the frame 22 does not include the spacers 46, or the lattice struts 32, or lattice struts 32 and support struts 42, are spaced apart in a different manner.

In particular embodiments, the fasteners 40 do not extend radially outwardly from their respective apertures 36, 38 in the struts and can be contained completely within the apertures. As shown in FIG. 3B, for example, each of the apertures 36 on the radially outermost struts 32 can include a counter-bore or enlarged recessed portion 37 that is sized to receive the head portion 41 of a respective fastener 40 (e.g., a rivet). The head portion 41 can be received entirely within the counter-bore 37 and does not extend radially outwardly from the counter-bore, for example, the head portion 41 can be flush with the outer surface of the strut 32. Similarly, the apertures 38 also can be formed with counter-bores to receive the head portions 41 of the fasteners. In this manner, the fasteners 40 do not increase or contribute to the overall crimp profile of the prosthetic valve and do not interfere with or place undue stresses on the delivery sheath of the valve (e.g., sheath 82 in FIG. 1).

Returning to FIG. 2, the prosthetic valve 14 can include a valvular structure 24 to regulate the flow of blood through the prosthetic valve. The valvular structure 24 can comprise, for example, a leaflet assembly 48 comprising one or more leaflets made of a flexible material. The leaflets can be configured to move between an open position allowing the flow of blood through the valve in a first direction and a closed position blocking the flow of blood through the prosthetic valve in a second direction, opposite the first direction. The leaflets of the leaflet assembly 48 can be made from in whole or part, biological material (e.g., pericardial tissue, such as bovine or equine pericardium), bio-compatible synthetic materials, or other such materials, such as those described in U.S. Pat. No. 6,730,118, which is incorporated herein by reference.

The prosthetic valve can also include an annular skirt or sealing member 50 that can be secured to the outer surface of the inflow end portion 26 of the frame 22, for example, with sutures 56 adjacent the inflow end portion 26 of the frame 22. The inflow end portion of the leaflet assembly 48 can be secured to the frame 22 and/or the skirt 50, for example using sutures 56. The skirt 50 helps establish a seal with the native tissue at the implantation site to prevent or minimize paravalvular leakage. In alternative embodiments, the prosthetic valve can have a skirt or sealing member mounted on the inside of the frame or a skirt or sealing member mounted on the inside and outside of the frame. The skirt can be formed from natural tissue (e.g., pericardial tissue) or any of various biocompatible synthetic materials, including biocompatible fabrics (e.g., polyethylene terephthalate (PET) fabric).

Further details regarding transcatheter prosthetic heart valves, including the manner in which the valve structure 24 can be coupled to the frame 22 of the prosthetic valve 14, can be found, for example, in U.S. Pat. Nos. 6,730,118, 7,393,360, 7,510,575, 7,993,394, and 8,652,202, which are incorporated herein by reference in their entireties.

Figure 4:
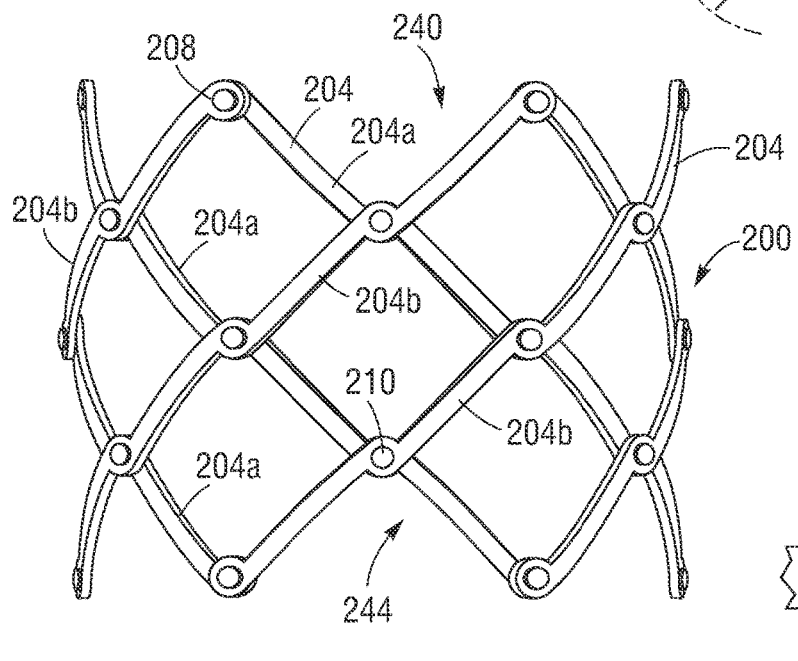
FIG. 4 is a side elevational view of the frame that can be used in the prosthetic valve of FIG. 2.

FIG. 4 is a side elevational view of a portion of a frame 200 that can be used with a prosthetic valve in at least certain embodiments of the present disclosure. While only one side of the frame 200 is depicted in FIG. 4, it should be appreciated that the frame 200 forms an annular structure having an opposite side that is identical to the portion shown. The frame 200 is similar to the frame 22 discussed above but does not include the longitudinal struts 42.

The frame 200 can include a plurality of lattice struts 204, including a set of inner struts 204a and a set of outer struts 204b pivotably connected to the inner struts 204a. Each of the lattice struts 204 can include a plurality of apertures 208. The apertures 208 can be used to connect the lattice struts 204 to one another using fasteners 210, such as described above for the lattice struts 32 (FIG. 2). In other implementations, the apertures 208 and fasteners 210 can be omitted.

For example, the lattice struts 204 can be fixedly connected to one another, such as by welding or adhesion, or by laser-cutting the individual struts of the frame from a metal tube. Although not shown in FIG. 4, a spacer may be included between the lattice struts 204, such as intermediate the portions of the lattice struts 204 having the apertures 208. In a particular example, the spacers can be configured as described above for the spacer 46. Similarly, if desired, the frame 200 can include support struts (not shown) that can be analogous to the support struts 42 (FIG. 2).

Figure 5:
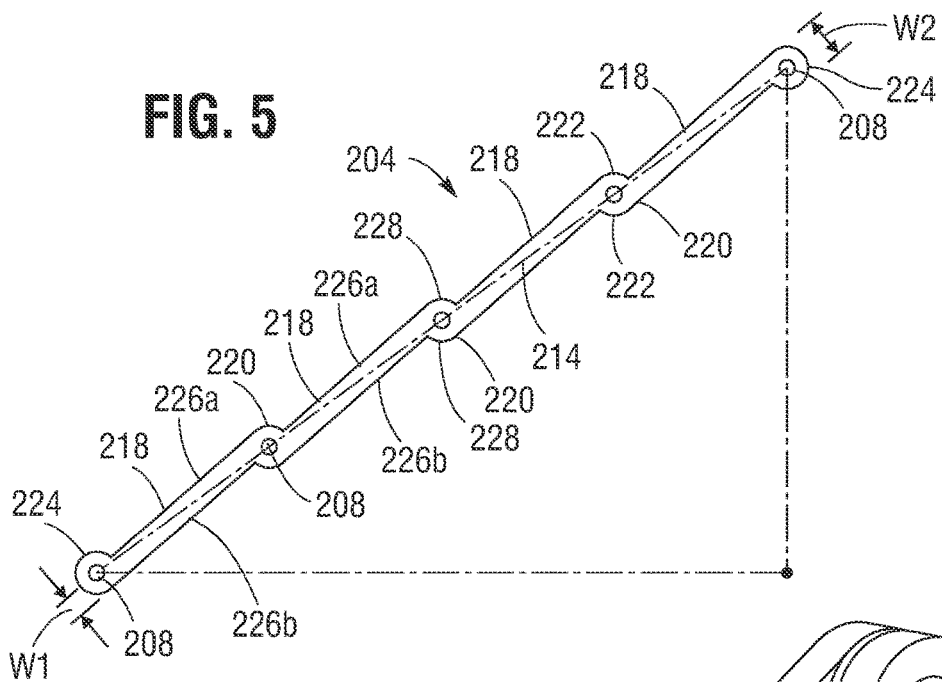
FIG. 5 is a side view of an embodiment of a flattened strut for a frame of a prosthetic valve, such as the frame of FIG. 4.

As best shown in the flattened view of the strut in FIG. 5, in one design that may be used with certain embodiments of this disclosure, each lattice strut 204 can have an offset, or zig-zag, pattern defined by a plurality of offset linear portions or segments 218. The linear segments 218 in the illustrated embodiment are arranged end-to-end relative to each other with adjacent ends interconnected to each other by intermediate segments 220. The strut 204 can have enlarged end portions 224 that form the apices at the inflow and outflow end of the frame. Each linear segment 218 is slightly laterally offset from an adjacent linear segment 218 in a direction perpendicular to the overall length of the strut 204 to provide the zig-zag pattern to the strut. Each of the intermediate segments 220 and end portions 224 can have a respective aperture 208 at its geometric center for receiving a fastener 210.

The amount of offset of each linear segment 218 relative to an adjacent linear segment along the length of the strut 204 can be constant such that an imaginary line 214 can pass through the aperture 208 of each intermediate segment 220 along the entire length of the strut. In alternative embodiments, the amount of offset between two adjacent linear segments 218 can vary along the length of the strut. For example, the amount of offset between linear segments 218 adjacent the outflow end of the frame can be greater than the amount of offset between linear segments 218 adjacent the inflow end of the frame, or vice versa.

The linear segments 218 can include at least substantially flat or linear opposing longitudinal edges 226a, 226b extending between curved or rounded edges 228 of the intermediate segments 220. In alternative embodiments, the opposing edges 228 of the intermediate segments 220 can be substantially flat or linear edges that extend at an angle between respective ends of the edges 226a, 226b of the liner segments 218.

As best shown in FIG. 5, the width W1 of each liner segment 218 is defined as the distance measured between the opposing edges 226a, 226b of a segment 218. In the illustrated embodiment, the width W1 is constant along the length of the strut 204. As such, each longitudinal edge 226a is laterally offset from an adjacent longitudinal edge 226a of an adjacent linear segment 218, and each longitudinal edge 226b is laterally offset from an adjacent longitudinal edge 226b of an adjacent linear segment 218. The width W2 of each intermediate segment 220 and end portion 224 can be greater than the width W1 of the linear segments 218.

In alternative embodiments, the width W1 of each linear segment 218 can vary along the length of a strut. For example, the width W1 of a linear segment 218 adjacent the inflow end of the frame can be greater than the width W1 of a linear segment 218 adjacent the outflow end of the frame, or vice versa. Further, where the width W1 of the linear segments 218 vary along the length of a strut 204, a linear segment can have one longitudinal edge 226a or 226b that is collinear with a longitudinal edge of an adjacent linear segment on the same side of the strut, while the other longitudinal edge 226a, 226b is laterally offset from the longitudinal edge of an adjacent linear strut on the same side of the strut. In other words, the strut 204 can have an overall zig-zag or offset pattern by virtue of the varying widths W1 of the linear segments.

Figure 6:
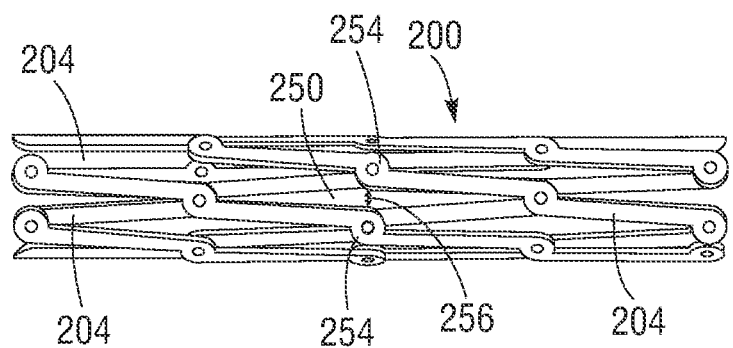
FIG. 6 is a side view of the frame of FIG. 4 shown in a radially compressed state.
Figure 7:
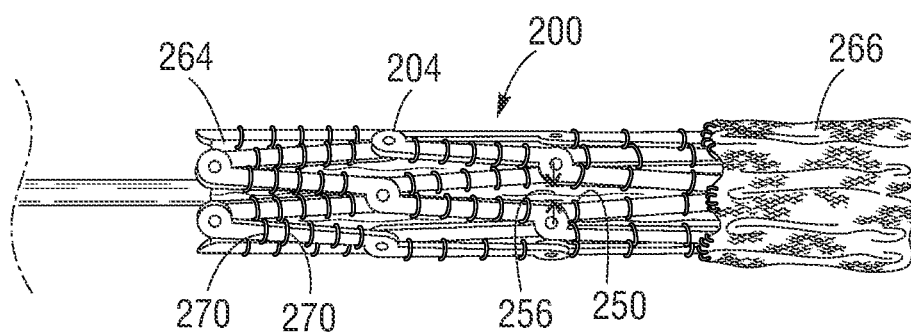
FIG. 7 is a side view of a prosthetic valve incorporating the frame of FIG. 4 shown in a radially compressed state.

The offset, or zig-zag, pattern of the strut segments 218 can help space apart the struts 204 in the circumferential direction when the frame 200 is in a radially compressed state, as shown in FIGS. 6 and 7. As shown, the open lattice structure of the frame 200 defining open cells 250 between the struts 204 can be preserved even when the frame 200 is fully compressed or contracted. For example, with reference to FIG. 6, although the width of the cells 250 along the length of the frame 200 can vary between adjacent struts, a gap 256 remains at the middle of a cell 250 between two adjacent pivot joints 254.

When the frame 200 is incorporated in a prosthetic valve (e.g., the prosthetic valve 14), the spaced-apart nature of the struts 204, including the gaps 256, can assist in protecting the soft components of the prosthetic valve as the frame 200 is expanded and contracted. FIG. 7, for example, shows a prosthetic valve comprising the frame 200, a skirt 266 mounted on the outside of the frame 200 and a leaflet assembly 264 mounted inside of the frame 200. An inner skirt (not shown) also can be mounted inside of the frame. The skirt 266 and leaflet assembly 264 can be coupled to the frame 200, such as with sutures 270. The sutures 270 can extend through the material of the skirt 266 and/or the leaflet assembly 264 and radially about the struts 204. The gaps 256 created by the offset configuration of the struts 204 can protect the leaflets 264, the skirt 266, and/or the sutures 270 from being pinched or sheared between adjacent struts 204 when the prosthetic valve is radially compressed. In this manner, the soft components of the prosthetic valve are protected against damage that can occur from contact with the metal struts of the frame.

The delivery apparatus 18 of FIG. 1 is particularly suited for implanting the prosthetic valve 14 or any of the other prosthetic valves disclosed herein. However, it should be noted that any of the prosthetic valves disclosed herein can be implanted using other suitable delivery apparatuses. For example, any of the prosthetic valves disclosed herein can be crimped over an inflatable balloon of a conventional balloon catheter. Once delivered to the implantation site, the balloon can be inflated to expand the prosthetic valve to its fully functional size.

Referring again to FIG. 1, the delivery apparatus 18 can include a handle 70, an elongate shaft 72 extending distally from the handle 70, a plurality of first actuation members 76 (also referred to as elongate positioning members), such as in the form of positioning tubes, extending through the shaft and distally outwardly from a distal end 78 of the shaft 72, a plurality of release members 106 (FIG. 9) extending through respective positioning members 76, and a plurality of second actuation members 86 (also referred to as "tethers") extending through respective release members 106. The positioning members 76 can be at least partially disposed radially within, and extend axially through, one or more lumens of the shaft 72. For example, the positioning members 76 can extend through a central lumen of the shaft 72 or through separate respective lumens formed in the shaft 72.

Figure 12:
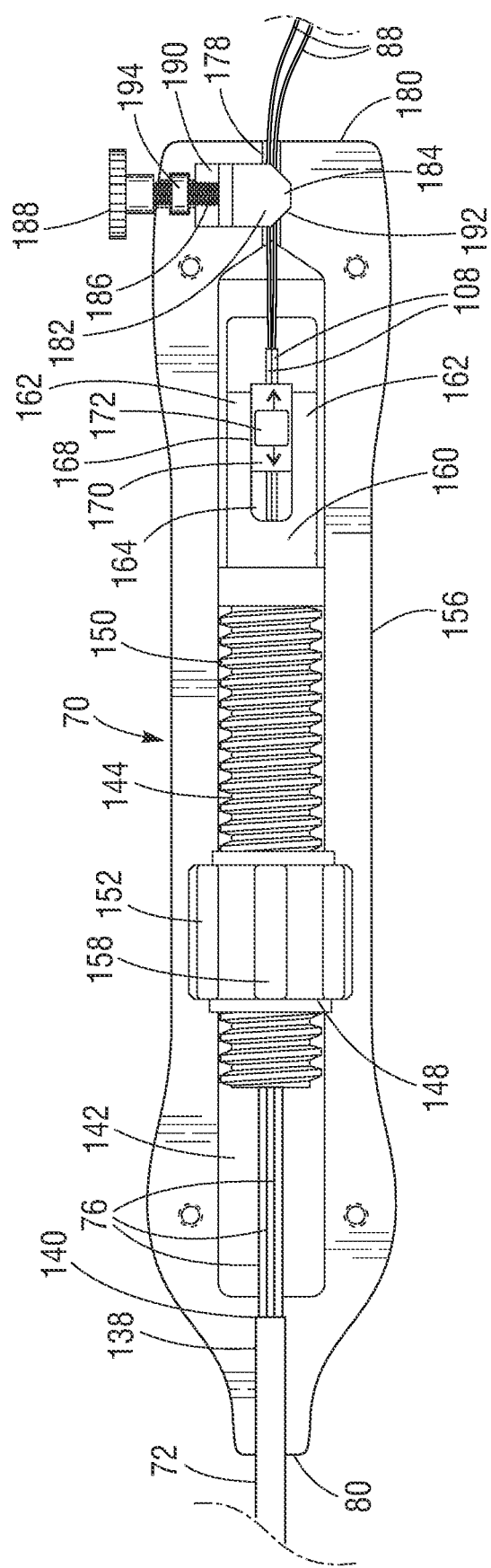
FIG. 12 is an enlarged cross-sectional view of the handle of the prosthetic valve delivery assembly of FIG. 1.

The shaft 72 can have a distal end portion 82 that can function as a sheath for containing or housing the prosthetic valve 14 in a radially compressed state for delivery through a patient's vasculature. In this regard, the distal end portion 82 can have a lumen that is sized to receive the prosthetic valve 14 in a radially compressed state. As shown in FIG. 12, the proximal end portion of the shaft 72 can extend into an axially extending bore 138 formed in the distal end portion of the handle 70. The proximal end portion of the shaft 72 can be retained within the axial bore 138 through pressure or frictional contact with the bore 138, using an adhesive, a clamp, a fastener, by thermally bonding the catheter 72 to the bore 138, or by some other technique or mechanism.

The positioning members 76 have distal end portions that can be releasably connected to the prosthetic valve 14 via respective release-and-locking units 94 (as best shown in FIG. 8). As shown in FIG. 12, the positioning members 76 can extend through the shaft 72, and proximally beyond a proximal end 140 of the shaft, and into a central bore 142 of the handle 70. A lead screw 144 can be disposed within the central bore 142 of the handle 70. The proximal ends of the positioning members 76 can be secured to the lead screw 144, such as being received within a bore (not shown) of the lead screw 144, where they can be secured by pressure or frictional contact with the bore of the lead screw 144, using an adhesive, a clamp, a fastener, thermal bonding, or another suitable technique or mechanism.

As shown in FIGS. 8 and 9, each actuation member 86 can extend through a lumen of a respective positioning member 76. The actuation members 86 can be coupled at their distal end portions to the distal end 60 of the frame 22. For example, the distal end portion of each actuation member 86 can be connected to an apex 34 at the distal end 60 of the frame, such as by welding, an adhesive, or a mechanical fastener. Each actuation member 86 can also extend through a lumen of a respective locking unit 94 that can be coupled to the frame 22, such as to an apex 34 at a proximal end 62 of the frame. The actuation members 86 can extend proximally into and through the handle 70. Proximal end portions 88 of the actuation members 86 can be releasably retained by a clamping member 182 mounted in or on the handle 70 (FIG. 12).

The actuation members 86 function to apply a proximally directed pulling force to the distal end 60 of the frame in cooperation with the positioning members 76 that apply a distally directed pushing force to the proximal end 62 of the frame to effect radial expansion of the frame 22. In particular embodiments, the actuation members 86 can comprise a relatively flexible but relatively non-elastic material that can effectively transfer pulling forces generated at the handle 70 to the distal end of the frame 22. For example, the actuation members 86 can comprise wires, sutures, strings, or similar materials. In other embodiments, the actuation members 86 can be relatively stiffer component, such as shaft or rod, that can transfer proximally directed pulling forces to the frame as well as distally directed pushing forces to the frame.

The release members 106 have distal end portions 107 that extend coaxially through respective locking units 94 (FIG. 9) and proximal end portions 108 that extend into the handle 70 (FIG. 12). The proximal end portions 108 of the release members 106 can extend through the lead screw 144 and can be secured to a release knob 168 within the handle 70.

Referring to FIGS. 1 and 12, a threaded actuator nut 148 can be disposed about the lead screw 144. Internal threads (not shown) of the threaded actuator nut 148 can engage threads 150 of the lead screw 144. An outer surface 152 of the threaded actuator nut 148 can extend through an aperture or window 154 formed in the outer surface 156 of the handle 70. The outer surface 152 of the threaded actuator nut 148 can include a texture, such as ridges 158, to aid a user in grasping and rotating the threaded actuator nut 148.

Rotation of the threaded actuator nut 148 in a first direction can cause the lead screw 144 to translate axially in the distal direction relative to the handle 70, thereby causing the positioning members 76 to translate distally through the lumen of the shaft 72. Rotation of the threaded actuator nut 148 in the opposite direction can cause the lead screw 144 to translate proximally relative to the handle, thereby causing the positioning members 72 to retract or translate proximally through the lumen of the shaft 72.

In particular implementations, the number and spacing of the threads 150 of the lead screw 144 (and thus the mating threads of the threaded actuator nut 148), and the axial length of the lead screw 144, can be selected to provide a desired degree of travel for the positioning members 76 and the release members 106. For example, the desired degree of travel can be sufficient to allow the frame 22 (and thus the prosthetic valve 14) to be manipulated between a fully expanded state (such as shown in FIGS. 2 and 8) and a fully contracted or compressed state (such as shown in FIGS. 6 and 7), including states in between being fully compressed or contracted and fully expanded, as further described below.

The release-and-locking units 94 (also referred to as "locking units") in the illustrated embodiment are configured to releasably connect the positioning members 76 to the frame 22 of the prosthetic valve 14 and to selectively secure the actuation members 86 to retain the prosthetic valve 14 in a deployed and expanded state. With reference to FIGS. 8-11, the locking units 94 can comprise a generally cylindrical body 96, which can be secured to the frame 22 of the prosthetic valve 14 by a fastener 130 (e.g., a pin or rivet). The fastener 130 can extend through an aperture 132 (FIG. 11) formed in the body 96 and through one or more corresponding apertures 36 in the frame struts 32 forming the apices 34 of the frame (FIG. 8).

The body 94 can comprise a locking feature, such as in the form of a clamp 98, disposed adjacent a distal end 100 of the locking unit 94 for selectively engaging an actuation member 86. The clamp 98 can comprise, for example, a pair of diametrically opposed jaws 102 that are biased radially inwardly toward each other (as best shown in FIG. 11). A release member 106 can be disposed within a lumen of each locking unit 94 to retain the jaws 102 of the clamp in a non-engaged or non-locking state during delivery of the prosthetic valve 14 (FIG. 9). Each release member 106 can extend proximally through a respective positioning member 76 to the handle 70. As discussed above, the proximal end portions 108 of the release members can be secured to a release knob 168 in the handle (FIG. 12). Each actuation member 86 can extend proximally through a lumen of a respective release member 106 into the handle 70.

In particular implementations, the release members 106 can be made from any suitable biocompatible metallic material or a polymeric material. In at least some examples, the material can be selected to allow the release members 106 to be easily moveable relative to the jaws 102 during valve deployment, as further described below. For example, the release members 106 can be made from a lubricious or low friction material (e.g., PTFE) or can have an outer layer made from a lubricious or low friction material (e.g., PTFE).

When the release members 106 are disposed within the locking units 94 extending between the jaws 102, the jaws 102 are held in an unlocked state and are prevented from contacting the actuation members 86. In the unlocked state, the actuation members 86 and the positioning members 76 can move freely in the axial direction with respect to one another to control radial expansion and compression of the prosthetic valve 14. When the prosthetic valve 14 is to be released from the delivery apparatus 18, the release members 106 can be retracted proximally relative to the locking units 94 and the positioning members 76. As shown in FIGS. 10A and 11, once the release members 106 are removed from engagement with the jaws 102, the jaws 102 can move to a locked or engaged state engaging the actuation members 86, thus securing the actuation members 86 from further axial movement, thus retaining the frame 22 of the prosthetic valve 14 in a desired expanded state.

Referring back to FIGS. 10A and 10B, the locking units 94 can be releasably coupled to the positioning members 76 by the release members 106. In the illustrated embodiment, for example, a distal end portion 110 of each positioning member 76 can include a coupling portion 112 that can include a tab 114 and a notch 116. Each locking unit 94 can include a corresponding notch 120 configured to receive the tab 114 of the positioning member 76. Similarly, each locking unit 94 can include a tab 122 to be inserted into, and received by, the notch 116 of a respective positioning member 76. The tabs 114, 122 and notches 120, 116, along with the release member 106, collectively can form a releasable, interlocking joint. The engagement of the tabs 114, 122 with the notches 120, 116 prevent axial separation of the positioning member 76 from the locking unit 94, while the release member 106, which extends through the tabs 114, 122 in the locked state, prevents lateral separation of the positioning member 76 from the locking unit 94.

As shown in FIG. 10B, the tab 114 of the positioning member 76 can include an axially extending slot 128. The slot 128 can be sized to allow the tab 114 to be placed around the actuation member 86 or removed from the actuation member 86 by passing the actuation through the slot 128. However, the slot 128 desirably is narrower than the diameter of the release member 106 to prevent lateral separation of the positioning member 76 from the locking unit 94 when the release member 106 is in a position extending through the tabs 114, 122 as depicted in FIG. 9. As noted above, retraction of the release member 106 from the jaws 102 of the clamp 98 allows the jaws to engage the actuation member 86. Further retraction of the release member 106 until the distal end of the release member 106 is proximal to the tab 122 and the notch 116 allows the distal end portion 110 of the positioning member 76 to be separated from the locking unit 94 in a lateral direction (in a direction perpendicular to the length of the locking unit and the positioning member), as depicted in FIG. 10A. As the positioning member 76 moves in a lateral direction away from the locking unit 94, the actuation member 86 can pass through the slot 128 in the tab 114.

As further shown in FIG. 10A, the tabs 114, 122 can be formed with respective inclined cam surfaces 124, 126, respectively, to facilitate the separation of the positioning member 76 from the locking unit 94. Each cam surface 124, 126 is inclined relative to the longitudinal axis of the positioning member 76 at angle less than 90 degrees. As such, applying a proximally directed force to the positioning member 76 in the direction of arrow 134 (such as by applying a pulling force to the positioning member at handle 70) causes the positioning member 76 to slide laterally away from the locking unit 94 in the direction of arrow 136.

The locking units 94 and/or the positioning members 76 can include a cutting mechanism to cut the portions of the actuation members 86 that extends proximally beyond the jaws 102 of the clamps 98 after the prosthetic valve is expanded and the release members are retracting to actuate the clamps. For example, a blade, or other cutting surface, can be placed across the slot 128, such that the actuation members 86 can be severed when they pass through the slot 128 during lateral separation of the positioning member 76 away from the locking unit 94.

In another example, the locking units 94 can include a clamping member that can include cutting jaws (such as sharpened or serrated jaws) positioning proximal to the jaws 102. The cutting jaws, like the jaws 102, can be retained in an open position away from the actuation member by the release member 106. When the release member 106 is retracted out of engagement with the cutting jaws, the cutting jaws can deflect radially inwardly against the actuation member 86, thereby severing it at that location. In further examples, a separate cutting device can be used to sever the actuation members 86 at a desired location after the positioning members 76 are released from the prosthetic valve 14, and optionally, after the delivery apparatus 18 is removed from the body.

Referring again to FIGS. 1 and 12, the lead screw 144 includes an extension portion 160 that extends proximally from the threaded portion of the lead screw. The extension portion 160 can comprise two leg portions 162 defining a U-shaped aperture or slot 164 between the leg portions 162. The release knob 168 can comprise a slidable member 170 disposed between the leg portions 162 and a user-engageable portion 172 extending radially outwardly from the slidable member 170. The proximal end portions 108 of the release members 106 can be fixedly secured to the slidable member 170, such as with a suitable adhesive, such that axial movement of the slidable member 170 in the distal and proximal directions causes corresponding movement of the release members.

The release knob 168 can be configured to be movable with, and also independently of, the lead screw 144. As noted above, axial movement of the lead screw 144 causes corresponding movement of the positioning members 76. Thus, when the release knob 168 is retained relative to the extension portion 160 of the lead screw 144, axial movement of the lead screw 144 causes the release knob 168 and the release members 106 to move with the positioning members 76, such as during deployment and expansion of the prosthetic valve. When the release knob 168 is not retained relative to the extension portion 160 of the lead screw 144, the release knob 168 can be translated axially relative to the extension portion, thereby effecting axial movement of the release members 106 relative to the positioning members 76 to actuate the clamping mechanism 98 of the locking unit 94 and release the positioning members 76 from the frame 22 of the prosthetic valve.

Various mechanisms can be used to selectively and releasably retain the release knob 168 axially relative to the extension portion 160 of the lead screw 144. For example, a moveable pin or similar mechanism can be inserted through the slidable member 170 and one or both leg portions 162 of the extension portion 160 to retain the axial position of the slidable member 170 relative to the lead screw 144. Removing the pin from the slidable member 170 and/or the leg portions 162 allows axial movement of the release knob 168 relative to the lead screw.

In another embodiment, the slidable member 170 can be configured to move between a first position where it is frictionally engaged by the extension portion 160 and a second position where the slidable member 170 is no longer frictionally engaged by the extension portion 160. In the first position, the axial movement of the lead screw 144 causes corresponding movement of the release knob 168. In the second position, the release knob 168 can be moved axially independently of the lead screw 144 in the distal and proximal directions.

The actuation members 86 can extend proximally beyond the proximal end portions 108 of the release members 106 and through an axially extending bore or opening 178 formed in the proximal end portion 180 of the handle 70. The actuation members 86 can be selectively secured relative to the handle 70 using a clamping, or retaining, mechanism 182. The retaining mechanism 182 can comprise a plug member 184, a screw member 186 connected at one end of the plug member 184, and knob 188 connected to the opposite end of the screw member 186. The plug member 184 can be positioned in a radially bore 184 formed in the proximal end portion 180 of the handle 70. The plug member 184 can include a triangular or trapezoidal lower surface that can be placed in, and removed from, contact with a corresponding shaped surface 192 of the radial bore 190. In other implementations, the plug member 184 can have a different shape. The screw member 186 extends through a captured nut 194 such that rotation of the knob 188 causes the plug member 184 to move toward or away from the surface 192 of the radial bore 190.

When the knob 188 is fully tightened (such as by rotating the knob 188 in a first direction), the lower surface of the plug member 184 can clamp the actuation members 86 against the surface 192, thereby securing the actuation members 86 against movement relative to the handle 70, the shaft 72, the locking units 94, and the frame 22 of the prosthetic valve. When the knob 190 is rotated in the opposite direction, the plug member 184 can move away from the surface 192 and the actuation members 86, allowing the actuation members to move relative to the handle 70, the shaft 72, the locking units 94, and the frame 22 of the prosthetic valve.

To use the delivery apparatus 18 to delivery and implant the prosthetic valve 14 at a desired location within the heart (e.g., the native aortic valve), the prosthetic valve 14 is connected to the positioning members 76 using the locking units 94 and the release members 106, as shown in FIGS. 8 and 9. The release knob 168 is retained relative to the lead screw 144 to prevent relative movement between the positioning members 76 and the release members 106. The prosthetic valve 14 can then be radially compressed or crimped to a compressed state, as shown in FIG. 7. The compressed prosthetic valve 14 can be loaded into the sheath 82 of the shaft 72.

Conventional techniques and devices can be used to insert and advance the delivery apparatus 18 and the prosthetic valve 14 through a patient's vasculature to the desired implantation site. For example, a prosthetic aortic valve can be delivered in a retrograde approach by advancing the delivery apparatus through a femoral artery and the aorta to the native aortic valve. At or adjacent the implantation site, the prosthetic valve 14 can be deployed from the sheath 82 by rotating the actuator nut 148 in a direction to cause the lead screw 144 to move distally relative to the handle 70. This causes the positioning members 76 and the release members 106 to move distally relative to the shaft 72. The positioning members 76 push the prosthetic valve 14 distally relative to the shaft 72. The actuator nut 148 can be rotated until the prosthetic valve is deployed from the distal end of the sheath 82. In some implementations, the inherent resiliently of the frame 22 may cause the prosthetic valve to at least partially expand when advanced from the sheath 82.

As the prosthetic valve 14 is deployed from the sheath 82, the retaining mechanism 182 can be in a release position allowing the actuation members 86 to move distally with the prosthetic valve. In this manner, the actuation members 86 do not apply any expansion forces to the prosthetic valve as it is being deployed from the sheath. To apply an expansion force to the prosthetic valve, the retaining mechanism 182 is tightened to retain the actuation members 86 relative to the handle 70. Continued rotation of the actuator nut 148 causes the positioning members to continue to apply a distally directed force on the proximal end of the frame 22 while the actuation members 86 (which are now restrained by the retaining mechanism 182) become taught and apply a proximally directed force on the distal end of the frame 22. The application of these forces causes the frame 22 to foreshorten axially and expand radially.

In some embodiments, the retaining mechanism 182 can be kept in the locked or engaged position against the actuation members 86 during valve deployment so long as the actuation members are long enough and contain enough slack to avoid applying any expansion force on the prosthetic valve as it is advanced from the sheath 82. For example, the lengths of the actuation members 86 can be selected to avoid applying any expansion force on the prosthetic valve as it is advanced from the sheath 82 and after the prosthetic valve is fully deployed from the sheath, the actuation members 86 become taught and begin to apply an expansion force on the frame opposite the expansion force of the positioning members 76 to expand the prosthetic valve.

If re-positioning or complete withdrawal of the prosthetic valve from the body is required, the user can rotate the actuator nut 148 in the opposite direction, which causes the positioning members 76 to pull the prosthetic valve back into the sheath 82. The action of the distal end portions 110 of the positioning members 76 being retracted into the sheath 82 causes the prosthetic valve to compress radially. If desired or needed, the prosthetic valve can be partially compressed without being retracted into the sheath and then re-positioned and re-expanded by rotating the actuator nut 148. In some cases, the prosthetic valve can be completely retracted back into the sheath 82 for re-positioning or complete withdrawal of the prosthetic valve from the body.

Once the prosthetic valve is expanded and positioned at the desired location, the release members 106 can be retracted from the locking units 94. This can be accomplished by releasing the release knob 168 from the lead screw 144 and retracting the release knob 168 proximally, which causes the release members 106 to retract relative to the locking units 94. When the distal ends of the release members 106 are proximal to the jaws 102 of the clamping mechanism 98, the jaws can engage the actuation members 86 to retain the prosthetic valve in the expanded state. Further retraction of the release members 106 past the tabs 122 of the locking units 94 allows the positioning members 76 to be released from the locking units. Retraction of the positioning members 76 by rotation of the actuator nut 148 or retracting the handle 70 causes the distal end portions 110 of the positioning members to pull free of the locking units 94. As discussed above, the portions of the actuation members 86 proximal to the clamping mechanisms 98 can be severed and removed from the body. Thereafter, the delivery apparatus can be withdrawn from the body.

The frame designs discussed above in connection with FIGS. 2 and 4 include a set of inner struts and a set of outer struts pivotably connected to inner struts by rivets or equivalent fasteners (e.g., inner and outer struts 204a, 204b, respectively, of FIG. 4). This may require anywhere from 10 to 50 additional small parts that are secured to the frame by welding or plastic deformation. Individual rivets, for example, may be less than a millimeter (e.g., 0.8 mm) in length and less than a millimeter (e.g., 0.8 mm) in diameter. As can be appreciated, the assembly process for assembling the frame can be time-consuming and can add significant cost to the manufacturing process. And, these additional elements can increase the overall crimp profile of the frame, as well.

Additionally, the outer struts typically are slightly longer than the inner struts to account for the fact that the outer struts are positioned radially outward of the inner struts and have a greater radius of curvature than the inner struts. As such, full pivoting movement between the inner and outer struts may be inhibited when the frame foreshortens upon radial expansion due to the different lengths of the inner and outer struts. To accommodate the different lengths of the inner and outer struts and allow for full movement of the struts, the apertures at the junctions of the inner and outer struts (e.g., apertures 208) that receive rivets or other connectors can be slightly elongated and/or enlarged, although this can present challenges for manufacturing and reliability. Additionally, such designs may introduce additional loads such as twisting and bending moments that act on the hinges between the struts.

Figure 13:
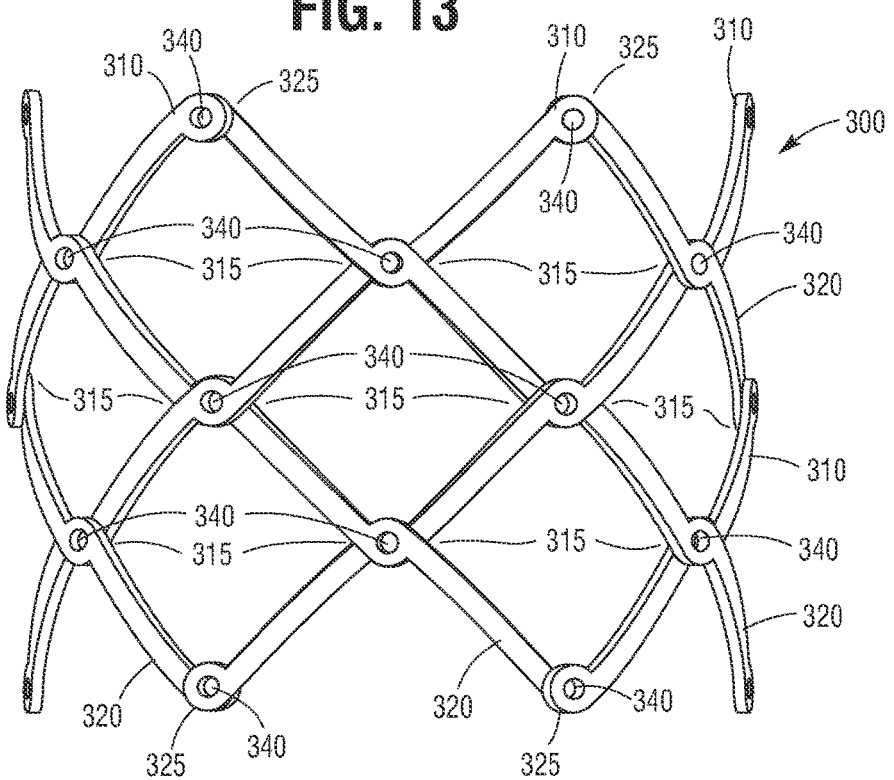
FIG. 13 is a side elevational view of another embodiment of a frame formed from interwoven struts.

As shown in FIG. 13, a frame 300 for a prosthetic heart valve, according to another embodiment, comprises a first set of struts and a second set of struts. The first set of struts comprises a plurality of first struts 310 (shown in the figure as extending from the lower left to the upper right). The second set of struts comprises a plurality of second struts 320 (shown in the figure as extending from the upper left to the lower right) interwoven with the first struts 310 in such a manner that each strut passes over and under struts of the other set. Since in this embodiment, there are no "inner struts" and "outer struts," but rather two sets of interwoven struts, the struts of both may be of the same length. In some embodiments, then, the same basic part may be used for all struts; in other words, all struts may have of the same size and shape. In some other embodiments, structurally similar struts with differences in manufacturing only in and around the areas of potential junctions with other struts may be used.

Also, in embodiments where the first struts 310 and the second struts 320 are of the same length, the frame may reduce or eliminate any "mismatch" in foreshortening (i.e., all struts can foreshorten the same amount and permit full movement of struts during radial expansion) without the need to enlarge or elongate the apertures 340 at the junctions of the struts.

In some embodiments, the frame 300 can include separate fasteners (e.g., fasteners 40) that extend through respective apertures 340 at the junctions 315, 325 of the struts. Advantageously, interweaving the struts 310 and 320 can reduce the number of hinge connections at the junctions 315, 325 between the struts. For example, in some embodiments, the frame can include fasteners (e.g., fasteners 40) only at the junctions 325 that define the apices at the inflow and outflow ends of the frames. The junctions 315 located axially between the junctions 325 at inflow and outflow ends of the frame can be without any fasteners interconnecting a pair of overlapping struts. Instead, due to interweaving of the struts and the inherent elasticity of the struts, the struts can be placed in tension, thereby urging first and second struts together at each junction. The tension imparted on the struts at junctions 315, along with the mechanical connections at junctions 325, can be sufficient to hold the assembly of struts together.

In alternative embodiments, the frame 300 can include fasteners at selected junctions 315 to reinforce the connection between the struts 310, 320, depending on the overall size and shape of the frame. For example, in one implementation, the frame 300 can include fasteners only at the junctions 315 at the middle of the frame (i.e., the junctions 315 that intersect a plane bisecting the frame halfway between inflow and outflow ends of the frame). For purposes of illustration, each strut 310, 320 is shown having an aperture at each junction 325 with an overlapping strut. However, in the embodiments described above where there are no fasteners at selected junctions 315, the struts 310, 320 need not be formed with any apertures 340 at the selected junctions. As can be appreciated, reducing the number of fasteners needed to assemble the frame can greatly reduce manufacturing costs.

In other embodiments, rather than employing separately formed fasteners (e.g., rivets) that typically are manually inserted into the apertures at each junction to form a hinge, the frame 300 can have integral fasteners at strut junctions 315, for example as shown in the embodiments in FIGS. 14A-18, as discussed further herein. Similar to the integral fasteners 40 described with respect to FIG. 2, the struts with integral fasteners can be configured to have a larger plastic deformation range than the struts that do not have fasteners. Variance in strut plasticity can be achieved by controlling the annealing process and/or selecting materials having desired elastic and/or plastic properties as described above.

Figure 14A:
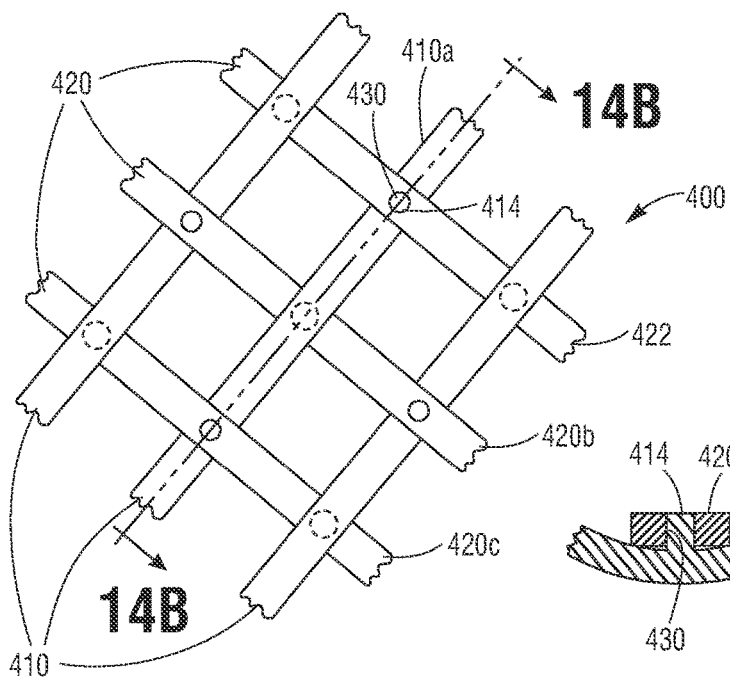
FIG. 14A is an enlarged, partial view of another embodiment of a frame formed from interwoven struts.
Figure 14B:
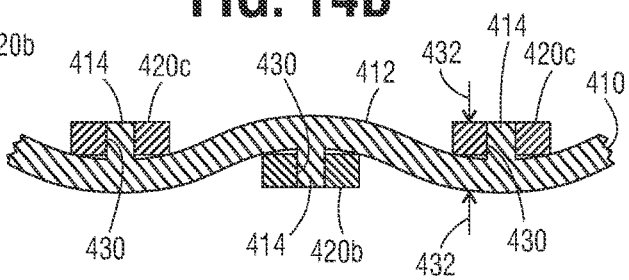
FIG. 14B is a cross-sectional view of the frame of FIG. 14A taken along line 14B-14B of FIG. 14A.

FIGS. 14A and 14B illustrate one embodiment frame 400 for a prosthetic heart valve, wherein the frame has integral fasteners for forming hinges between overlapping struts. In this embodiment, the frame 400 comprises a first set of struts 410 interwoven with a second set of struts 420. For example, a first strut 410a of the first set of struts 410 can be interwoven with at least a second strut 420a, a third strut 420b and a fourth strut 420c of the second set of struts 420.

Each first strut 410 can include a plurality of integral protrusions or projections 414 spaced apart from each other along the length of the strut. Each second strut 420 can include a plurality of openings or apertures 430 spaced apart from each other along the length of the strut, with each aperture receiving a respective projection 414 to form a hinge between two overlapping first and second struts. As shown, the projections 414 extend alternately from one side of the strut 410 and from the other side of the strut from one projection to the next to allow each projection 414 to extend into a corresponding aperture 430 of an overlapping strut 420 in the weave.

In some embodiments, an integral projection 414 (or other feature of a strut) is formed directly on the strut rather than being separately formed and subsequently attached to the strut.

As shown in FIG. 14B, the first strut 410 can be elastically deformed from weaving the first strut through successive second struts 420a, 420b, 420c. Due to the elasticity of the struts, the struts are placed in tension, urging the first strut against each second strut at each junction (illustrated by force lines 432), which helps retain each projection 414 within an aperture 430. In some embodiment, the struts can initially be straight and then can be elastically bent as they are woven together. In other embodiments, first and/or second struts may be pre-formed with curves or bends (such as by heat setting a shape memory material) at the locations of the junctions to facilitate assembly of the frame. The struts can be formed from, for example, super-elastic materials (Nitinol) or non-super-elastic materials (e.g., stainless steel or cobalt chromium alloys), although super-elastic materials are desirable in certain embodiments to maximize the elastic retention forces 432 at the junctions of the struts.

In the illustrated embodiment, the struts 410, 420 of the frame 400 are arranged in a basic, or plain weave pattern, where each first strut 410 extends over then under each successive second strut 420. In alternative embodiments, the struts 410, 420 can be arranged in various other weave patterns. The placement of the projections 414 can be modified from the configuration shown in FIG. 14B to correspond with the locations of the junctions formed by the particular weave pattern of the struts.

The struts 410, 420 can be manufactured using any of various suitable techniques, as previously described herein. In some embodiments, the struts can, for example, be laser cut from a tube, or laser cut or punched from a flat sheet of metal. Optionally, the struts can undergo an additional rolling process to shape the struts into their final shape prior to assembly. In some embodiments, the struts can be formed with a plurality of spaced apart tab portions that are plastically bent or heat set to form the plurality of projections.

Figure 15A:
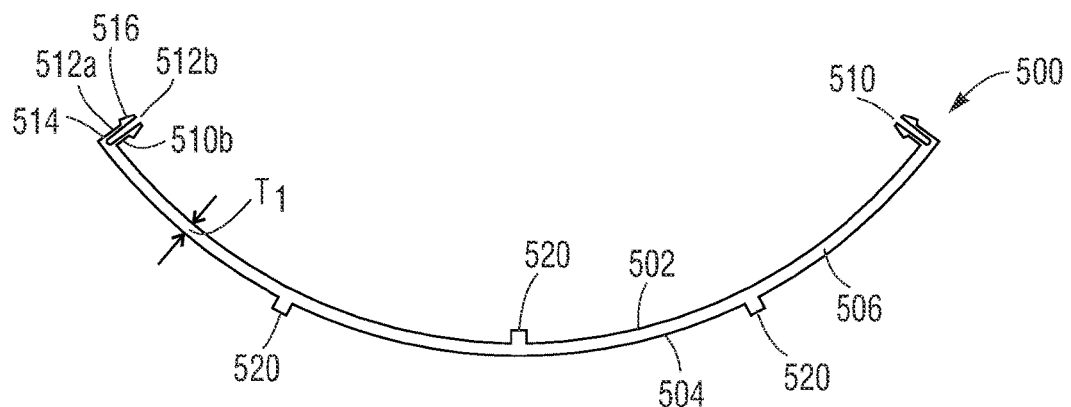
FIG. 15A is a plan view of one embodiment of a first strut having integral fasteners.
Figure 15B:
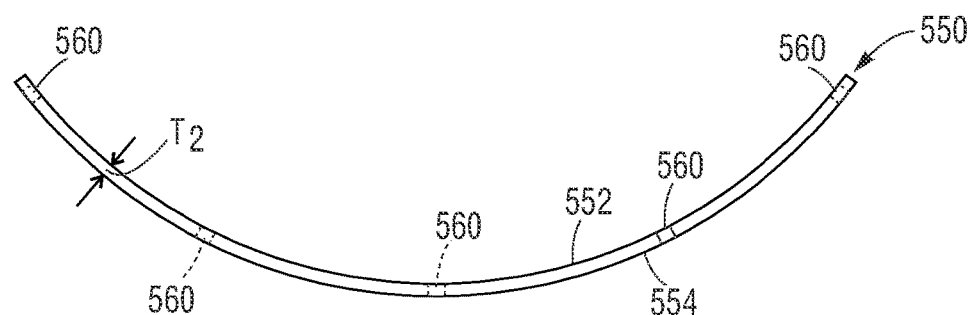
FIG. 15B is a plan view of one embodiment of a second strut that, along with additional such struts, can be used with multiple of the struts shown in FIG. 15A to form a frame.

FIGS. 15A and 15B illustrate an alternative embodiment pair of first and second struts 500 and 550, respectively, which can be used to form a frame from a plurality of the first struts 500 and a plurality of the second struts 550. In particular embodiments, each strut 500, 550 can be formed (e.g., laser cut) from a flat sheet of material (e.g., a flat sheet of metal) to form a strut having a radius of curvature that defines the outer curved surface of a frame with other similar struts that are assembled together to form the frame.

FIGS. 15A and 15B show the struts as viewed from an axial end of the frame. Thus, the strut 500 has a radially inwardly facing inner surface 502 that forms part of the inner surface of the frame and a radially outwardly facing surface 504 that forms part of the outer surface of the frame. The strut 500 has a radial thickness T1 defined between the surfaces 502, 504. The strut 500 also has longitudinally extending, axially facing side surfaces 506, 508 (see also FIG. 16A) defining a width W1 equal to the thickness of the sheet of material from which the strut is formed.

Similarly, the strut 550 has a radially inwardly facing inner surface 552 that forms part of the inner surface of the frame and a radially outwardly facing surface 554 that forms part of the outer surface of the frame. The strut 550 has a radial thickness T2 defined between the surfaces 552, 554. The strut 550 also has longitudinally extending, axially facing side surfaces 556, 558 (see also FIG. 16A), which as best shown in the side view of FIG. 15C define a width W2 equal to the thickness of the sheet of material from which the strut is formed.

Figure 15C:
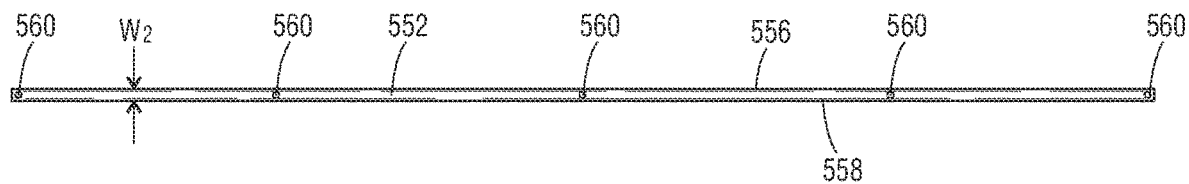
FIG. 15C is a side view of the inwardly facing surface of the strut of FIG. 15B.

The struts 500, 550 can be formed with integral features that mate with corresponding features of an overlapping strut to form hinges at the junctions of two struts. In particular, the strut 500 can be formed with integral projections 510 at opposite ends of the strut and integral projections 520 spaced apart along the length of the strut between the end projections 510. The strut 550 can be formed with a plurality of apertures 560 spaced apart along the length of the strut at locations corresponding to the locations of the projections 510, 520, as best shown in FIGS. 15B and 15C. Each projection 510, 520 can be received in a corresponding aperture 560 of an overlapping strut to form a hinge at a junction of two struts 500, 550. As shown in FIG. 15A, the projections 510, 520 in the illustrated embodiment alternatively extend along the inner surface 502 and the outer surface 504. Thus, some of the projections extend radially inward from a surface 502, 504 and some projections extend radially outward from a surface 502, 504. In this manner, each first strut 500 can be interwoven with a plurality of second struts 550, similar to struts 310, 320 of FIG. 13.

A strut 500, 550 having integral features for forming the hinges interconnecting two struts can be formed using any of various suitable techniques, including, without limitation, laser cutting, stamping, machining, electro-etching, electro-forming, three-dimensional printing, or the like. For example, the integral projection 510, 520 can be formed directly on the strut 500 by forming the entire shape shown in FIG. 15A from a single piece of material.

Each projection 510 at an opposite end of the strut 500 forms an apex of a frame when inserted into a corresponding aperture 560 of a strut 550. As further shown in FIG. 15A, the projections 510 can be configured to form a snap-fit connection or engagement with corresponding apertures 560. For example, in the illustrated embodiment, each projection 510 comprises a split projection having a first portion 512a and second portion 512b separated by a gap. Each of the first and second portions 512a, 512b can have a relatively narrow base 514 at the inner surface 502 and tapered, relatively wider end portion 516 spaced from the inner surface 502. The gap allows the first and second portions 512a, 512b to be displaced toward each other when the wider end portions 516 are inserted through an aperture 560. When the end portions 516 are passed completely through the aperture 560, the first and second portions 512a, 512b can return to their non-deflected state (shown in FIG. 15A) under their own resiliency, such that the wider end portions 516 prevent the projection 510 from backing out or separating from the aperture.

The projections 520 do not necessarily need to be fastened or retained inside corresponding apertures 560 with a snap-fit connection or other fasteners. In particular embodiments, the connections between two struts at the apices of a frame, along with intervening struts as described above, can be sufficient to retain the projections 520 within corresponding apertures 560 when the frame is assembled.

In particular embodiments, a frame can be assembled with a plurality of struts 500, 550 without using any other components (e.g., separate rivets and/washers) to form the hinge connections at the junctions of two struts 500, 550. As can be appreciated, the assembly process is much less time-consuming and costly than frames that require separate component to form the hinge connections.

In alternative embodiments, all of the projections 510, 520 can be formed on a single side of the strut 500 (side 502 or side 504), in which case the struts 500, 550 are not interwoven with each other. In still other embodiments, the projections may be alternated at other intervals, other than a single interval, so as to correspond to different "weaving" patterns for the struts 500, 550. For example, a single strut 500 can extend under two adjacent struts 550 and then over the next two adjacent struts 550.

Figure 16A:
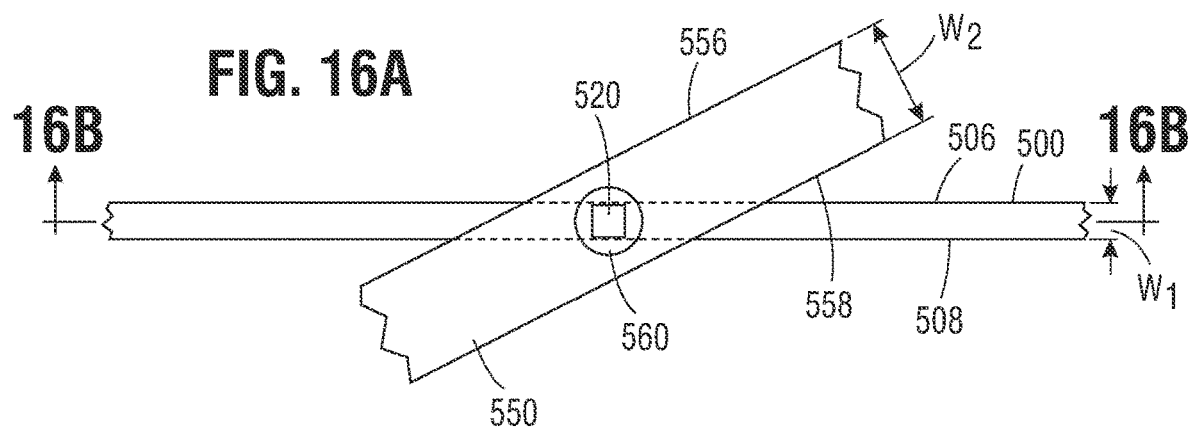
FIG. 16A is a side view of a hinge of a frame formed from the struts shown in FIGS. 15A and 15B.

FIG. 16A is a side view of a junction formed between a first strut 500 and a second strut 550, according to one embodiment. As shown, the first strut 500 passes under the second strut 550 at the point of engagement, or junction, between the struts. At this junction, the projection 520 of the first strut 500 extends into an aperture hole 560 in the second strut 550, providing a hinged connection around which the struts can rotate as a frame assembled from multiple struts 500, 550 radially expands or contracts.

Figure 16B:
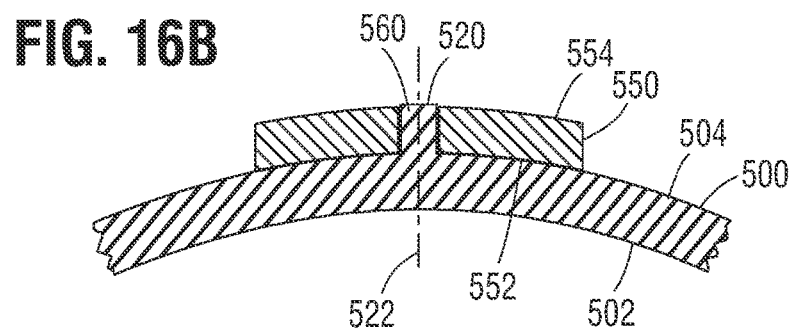
FIG. 16B is a cross-sectional view of the hinge of FIG. 16A taken along line 16B-16B of FIG. 16A.

FIG. 16B is a cross-sectional view taken along the line 16B-16B of FIG. 16A. It is understood that at other junctions along the first strut 500 where it interacts with other second struts 550, the first strut may instead pass over the next second strut with the projection 520 facing radially inwardly towards the second strut 550 to extend into the corresponding aperture 560 of that second strut. Additionally, certain junctions between first struts 500 and second struts 550 may have neither a projection 520 nor an aperture 560 formed in the struts, so long as each of the struts is connected to another strut at an apex of the frame.

In the embodiment of FIGS. 16A and 16B, the projection 520 has a square cross-sectional profile in a plane perpendicular to a pivot axis 522 of the projection. In other embodiments, the projection may have other cross-sectional shapes, such as a circle, triangle, etc.

Figure 17:
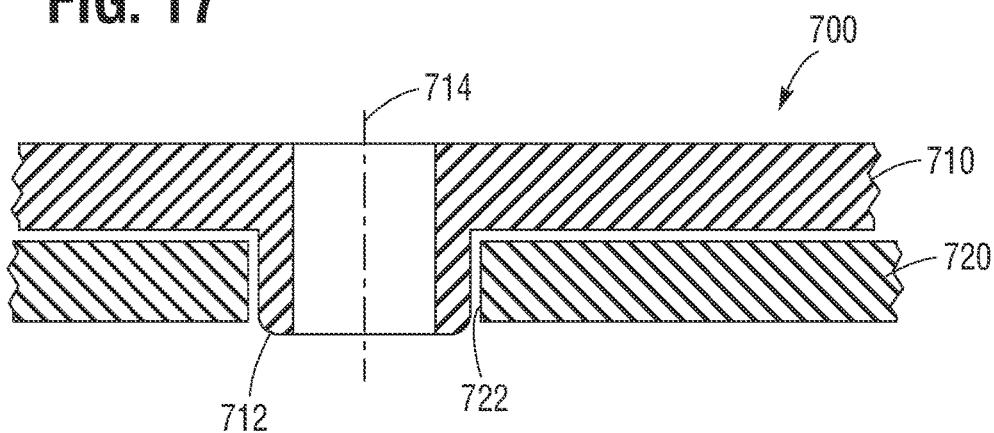
FIG. 17 is a cross-sectional view of another embodiment of a hinge formed from two struts of a frame.

FIG. 17 shows another embodiment of a hinged connection 700 formed by a first strut 710 and a second strut 720. The first strut 710 has a projection 712 that can be formed by flow drilling. As in the embodiment shown in FIG. 15B, the second strut 720 can include an aperture 722 cut or drilled therein, within which the projection 712 may sit, so that the two struts are pivotally engaged and can pivot relative to each other about a pivot axis 714. In another embodiment, rather than drilling an aperture 722 entirely through second strut 720, the second strut instead can include a blind hole or recess, such as formed by stamping, etching, or other means, into which projection 712 can extend to provide pivotal engagement between the struts.

Figure 18A:
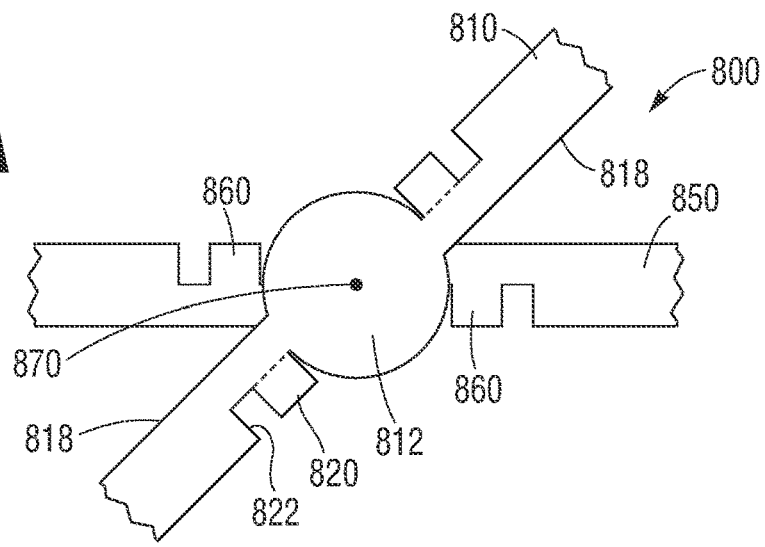
FIG. 18A is a side view of another embodiment of a hinge formed from two struts of a frame.
Figure 18B:
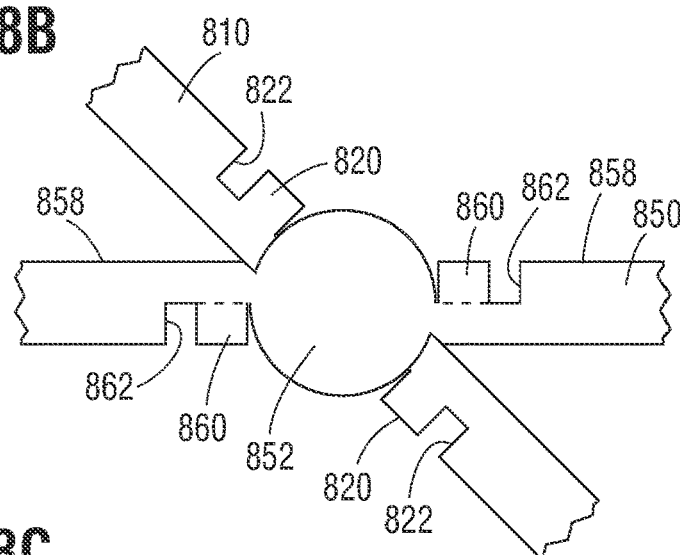
FIG. 18B is a side view of the opposite side of the hinge of FIG. 18A.
Figure 18C:
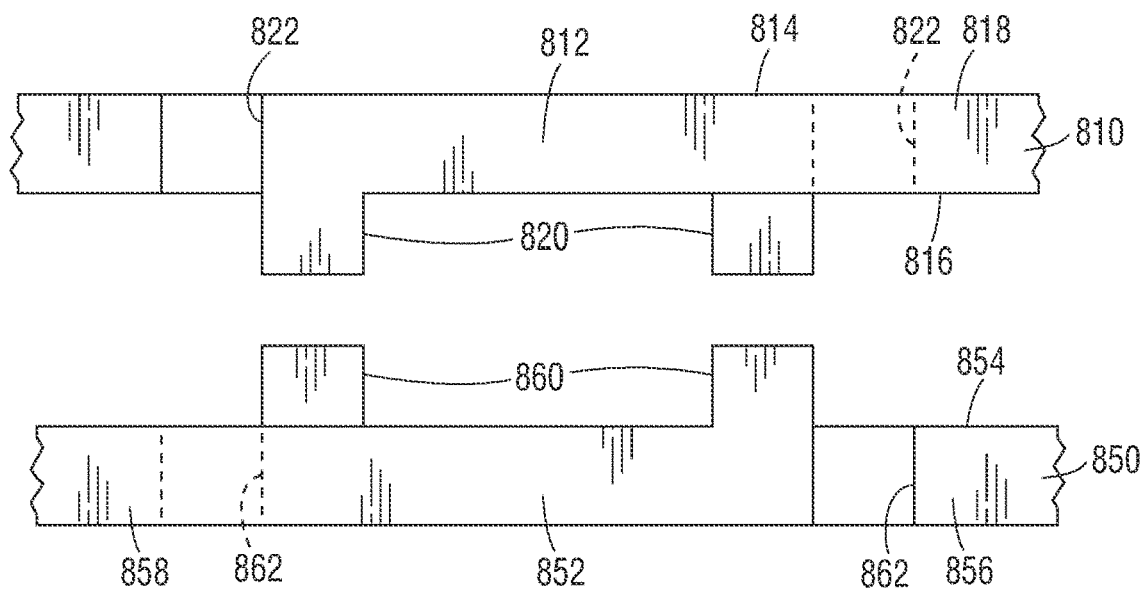
FIG. 18C is an exploded view of the hinge of FIG. 18A.

FIGS. 18A-18C show another embodiment of a hinge connection 800 between two struts 810, 850 formed by integral features on the struts. In this embodiment, a first strut 810 can comprise an enlarged node 812 at the location of each junction between two struts. The node 812 is wider than the remainder of the strut and may be circular in shape as shown, although other shapes can be used in other embodiments.

The first strut 810 includes a radially outwardly facing surface 814, a radially inwardly facing surface 816, and two longitudinally extending, axially facing surfaces 818. Two stopper tabs 820 are formed on either side of the node 812 and extend radially inwardly toward the second strut 850. One stopper tab 820 extends radially inwardly from one surface 818 and the other stopper tab 820 extends radially inwardly from the other surface 818. The first strut 810 also can have notches 822 formed in surfaces 818 adjacent the stopper tabs 820.

The second strut 850 similarly is formed with an enlarged node 852 at the location of each junction. The second strut 850 includes a radially outwardly facing surface 854, a radially inwardly facing surface 856, and two longitudinally extending, axially facing surfaces 858. Two stopper tabs 860 are formed on either side of the node 852 and extend radially outwardly toward the first strut 810. One stopper tab 860 extends radially outwardly from one surface 858 and the other stopper tab 860 extends radially inwardly from the other surface 858. The second strut 850 also can have notches 862 formed in surfaces 858 adjacent the stopper tabs 860.

As shown in FIGS. 18A and 18B, the struts 810, 850 are placed against each other so that the node 812 of the first strut overlies the node 852 of the second strut to form a hinge 800. The stopper tabs 820 of the first strut 810 extend radially inwardly along opposite sides of the node 852 of the second strut 850, while the stopper tabs 860 of the second strut 850 extend radially outwardly along opposite sides of the node 812 of the first strut 810. When the struts 810, 850 are pivoted relative to each other about a pivot axis 870, the stopper tabs 820 of the first strut can engage opposing sides 858 of the second strut, while the stopper tabs 860 of the second strut can engage opposing sides 818 of the first strut. In this manner, the stopper tabs 820, 860 limit the rotational movement of the struts relative to each other. Thus, a frame formed from multiples of the struts 810, 850 can have a maximum expanded diameter and a minimum compressed diameter determined by the range of movement of the struts allowed by the stoppers, can help avoid over-expansion and/or over-compression beyond desired limits.

Further, the engagement of the stopper tabs 820 against the outer side surface of the node 852 and the engagement of the stopper tabs 860 against the outer side surface of the node 812 can resist separation of the struts at least in the axial direction. In some embodiments, the struts 810, 850 can be interwoven, as shown in FIGS. 13, to place the struts in tension against each other to resist separation of the struts in the radial direction. Where the struts are interwoven, pairs of stopper tabs 820 spaced along the length of the strut can alternately extend from surface 814 and from surface 816. Similarly, pairs of stopper tabs 860 spaced along the length of the strut can alternately extend from surface 854 and from surface 856.

FIGS. 19A-19C illustrate a strut connector 900 (also referred to as a "rivet chain" in some embodiments) that can be used to interconnect struts of a frame of a prosthetic heart valve, according to another embodiment. In the illustrated embodiment, the strut connector 900 comprises a plurality of rivets or projections 910 connected by a support member 912, which is desirably formed as a unitary part with the projections 910 integrally formed on the support member 912. In one embodiment, the strut connector may 900 be manufactured using electro chemical machining (ECM), but it can be made using a number of other suitable different technologies, such as electrical discharge machining (EDM), laser machining or computer numerical control (CNC) machining, or molding. Other suitable processes may also be used.

The strut connector 900 need not be made of the same material as the frame to which it is affixed, since it is a separate part from the frame struts. The strut connector 900, including the projections 910 and the support member 912 can be formed form any of various biocompatible metals (e.g., stainless steel, nitinol) or polymers (e.g., polyurethane). The strut connector 900 desirably has sufficient flexibility to conform to the curvature of the outer or inner surface of the strut against which it is placed, as further described below.

FIG. 20 is a perspective view of a frame 1000, according to one embodiment, that can be assembled using strut connectors 900. The frame 1000 in the illustrated embodiment comprises a plurality of first, outer struts 1002 connected to a plurality of second, inner struts 1004. The frame 1000 can have a construction similar to the frame 200 of FIG. 4, except for hinged connections between the struts. Each strut 1002, 1004 can be formed with a plurality of apertures at the locations where the struts overlap each other, as previously described in connection with the frame 200. A strut connector 900 can be placed along the outer surface of each outer strut 1002, with each projection 910 extending through an aperture in the outer strut 1002 and into a corresponding aperture of an inner strut 1004. The hinged connection is thereby formed at each junction of a first strut 1002 and a second strut 1004.

In alternative embodiments, a strut connector 900 can be placed against the inner surface of each inner strut 1004, with each projection 910 extending through an aperture in the inner strut 1004 and into a corresponding aperture of an outer strut 1002. In still other embodiments, a strut connector 900 need not be formed with projections at every junction between the struts 1002, 1004. For example, in one specific implementation, a strut connector 900 can be formed with projections 910 at its opposite ends so as to form hinged connections at the apices along the inflow and outflow ends of the frame and optionally can include projections 910 at one or more selected locations along the length of the strut connector to form hinged connections between the inflow and outflow ends of the frame.

Further, while the illustrated frame 1000 includes single strut connector 900 aligned along each strut 1002, in other embodiments, multiple strut connectors 900 can be placed end-to-end along the length of each strut 1002 (or each strut 1004 if placed on the inside of the frame). Moreover, the strut connectors 900 can be implemented in other frame designs. For example, in one implementation, a frame can be formed from a plurality of interwoven first and second struts, similar to FIG. 13.

As can be appreciated, the use of strut connectors 900 to assemble the frame can greatly facilitate the manufacturing process by eliminating the step of manually placing individual rivets at each junction between the struts.

FIGS. 21-28 illustrate another embodiment of a frame 1100 for a prosthetic heart valve. As shown in FIG. 21, the frame 1100 in the illustrated embodiment is formed from a plurality of inner struts 1110 and a plurality of outer struts 1120 connected by hinges 1115 at junctions 1105. In alternative embodiments (not shown), the struts may be interwoven, as in the embodiment of FIG. 13.

The frame 1100 can include a plurality of actuators 1130 configured to radially expand and contract the frame and retain an expanded shape when deployed inside a patient's body. Each actuator 1130 can include an inner member, or piston, 1132 that extends through an outer member, or cylinder 1134. The inner member 1132 can be connected at one end thereof to a junction 1105 at one end of the frame, while the outer member 1134 can be connected to another junction 1105 of the frame. Longitudinal movement of the inner member 1132 relative to the outer member 1134 is effective to radially expand and contract the frame 1100, as previously described in connection with the embodiment of FIGS. 1 and 8-12. The inner members 1132 can be releasably connected to corresponding actuators of a delivery apparatus. Further details of the actuators 1130 are disclosed in co-pending application Ser. No. 15/831,197, filed Dec. 4, 2017, which is incorporated by reference in its entirety herein.

The components forming the hinges 1115 can be integrated into the construction of the struts. As best shown in FIGS. 22-26, for example, each strut 1110 comprises a plurality of integral projections 1112 spaced along the length of the strut at the locations of the junctions 1105. Each projection 1112 can include a cylindrical base 1114 and a locking member in the form of a plurality of ears 1118 extending laterally from the end of the base 1114. In the illustrated embodiment, each projection includes two ears 1118 that extend in opposite directions from the end of a base 1114, although more than two ears 1118 may be used in alternative embodiments.

Each strut 1120 can be formed with a plurality of openings or apertures 1122 spaced along the length of the strut at the locations of the junctions 1105. Each opening 1122 can include two oblong side portions 1124 corresponding to the shape of the ears 1118. Each opening 1122 can be formed within a recessed portion 1126 formed on an outer surface of a strut 1120.

In the assembled state of the frame 1100, the base 1114 of each projection 1112 extends through a corresponding opening 1122 with the ears 1118 residing in the recessed portion 1126 surrounding the opening. The depth of the recessed portion 1126 desirably is equal to or greater than the height of the ears 1118 so that the projections do not extend radially beyond the outer surfaces of the outer struts 1120. The ears 1118 and the correspondingly shaped oblong side portions 1124 allow the ears of the projection 1112 to be inserted through the side portions 1124 when the ears 1118 and the oblong side portions 1124 are rotationally aligned with each other and then prevent separation of the two struts 1110, 1120 when the ears 1118 and the side portions 1124 are rotationally offset or misaligned from each other.

During assembly, the ears 1118 of a strut 1110 are aligned with the oblong side portions 1124 of an opening 1122 of a strut 1120 corresponding to a predetermined angle between the struts 1110, 1120 which is greater than the maximum angle between the struts 1110, 1120 allowed by the actuators 1130 during radial expansion of the frame 1100. Thus, once the projections 1112 of struts 1110 are inserted through corresponding openings 1122 of struts 1120 to form the frame, the struts are then rotated relative to each other, which causes the ears 1118 to become offset from the oblong side portions 1124. The actuators 1130 can then be mounted on the frame. The actuators 1130 are configured to radially expand and contract the frame, as noted above, but desirably limit the radial expansion and contraction of the frame within a predetermined range of diameters and a predetermined range of angles between the struts 1110, 1120 at which the ears 1118 are still rotationally offset from the oblong side portions 1124. In this manner, the actuators 1130 can prevent radial expansion of the frame to a diameter at which the ears 1118 are rotationally aligned with the oblong side portions 1124, thereby preventing separation of the struts 1110, 1120 at any of the junctions 1105. Similarly, the actuators 1130 can prevent radial contraction of the frame to a diameter at which the ears 1118 are rotationally aligned with the oblong side portions 1124, thereby preventing separation of the struts 1110, 1120 at any of the junctions 1105 when the frame is compressed to a delivery configuration.

In this manner, the hinges 1115 formed by projections 1112 and corresponding openings 1122 can be referred to as "self-locking" hinges in that the mechanical engagement of the ears 1118 with the adjacent surface of the recessed portion 1126 locks the struts together at a junction 1105 and need not rely on placing the struts in tension against each other to retain a connection between the struts. Consequently, the struts need not be formed from super-elastic materials (e.g., Nitinol) to maximize tension on the struts. While the struts can be formed from super-elastic materials or non-super-elastic materials (e.g., stainless steel or cobalt chromium alloys), non-super-elastic materials are desirable in some embodiments because they can provide greater crush resistance and typically are less expensive than super-elastic materials.

The self-locking hinges 1115 can be formed from the projections 1112 and openings 1122 having any of various shapes in addition to those shown in the illustrated embodiment. In general, the projections 1112 can be formed with a locking member that has a non-circular shape (in a plane perpendicular to the central axis of the projection) and the openings 1122 can have any non-circular shape that be rotationally aligned with the locking member to permit assembly of the struts and then rotationally offset from the locking member to prevent separation of the struts at the hinge.

Figure 27:
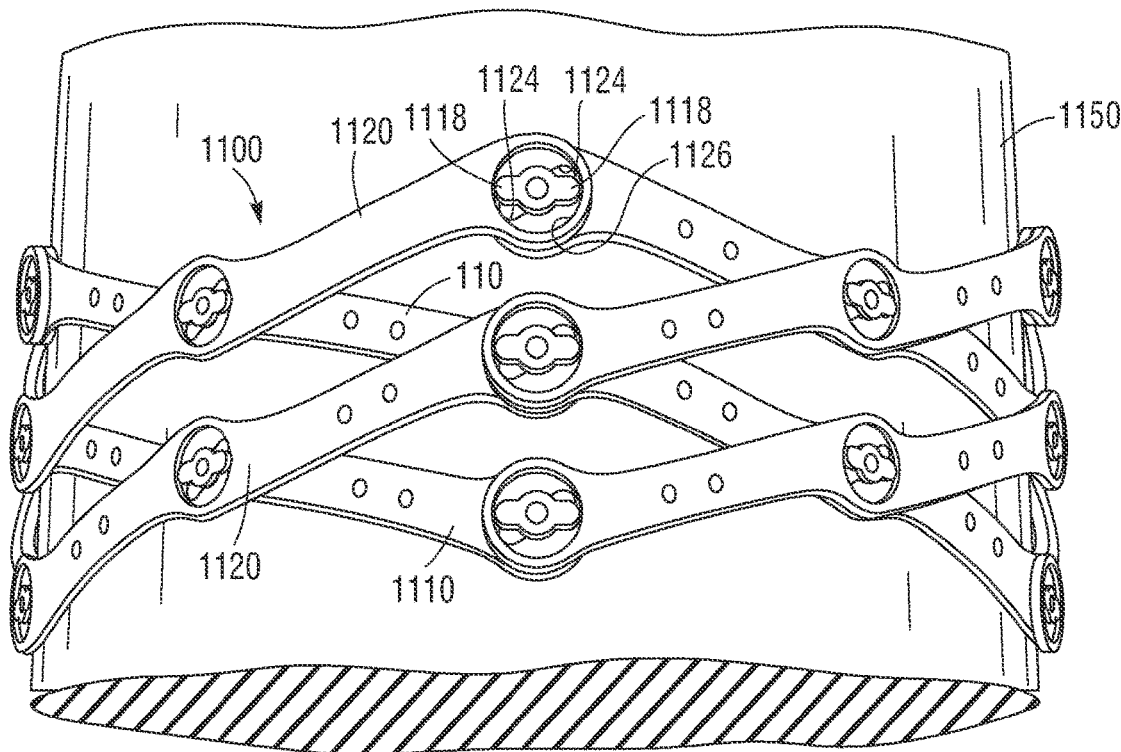
FIG. 27 is a perspective view showing the frame of FIG. 21 assembled on a mandrel.
Figure 28:
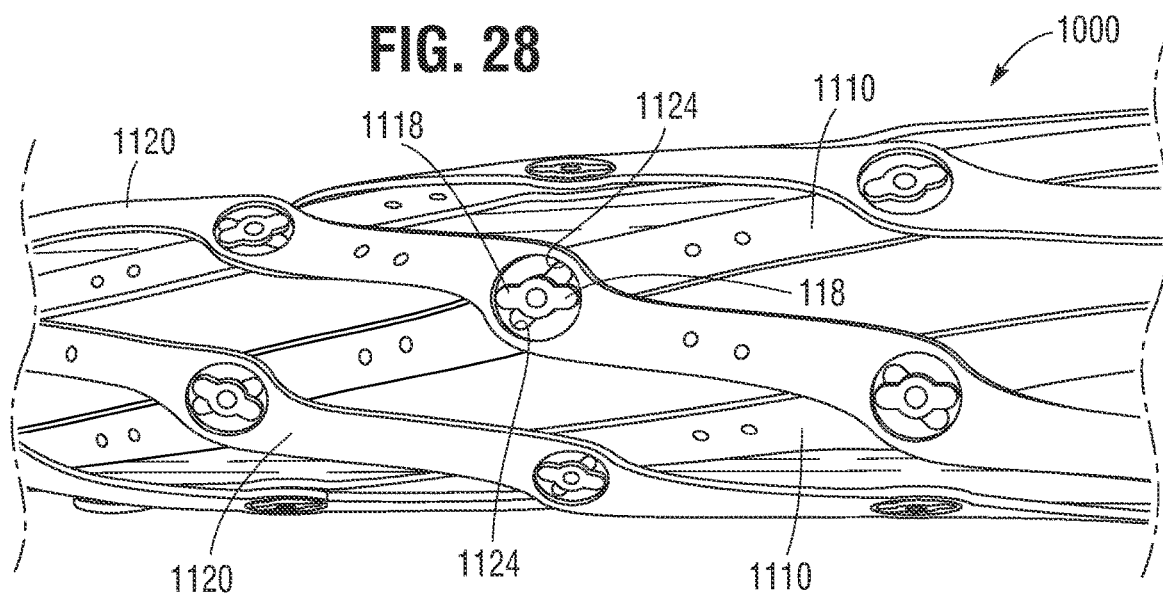
FIG. 28 is a side view of the frame of FIG. 21 in a compressed state.

In particular embodiments, the frame 1100 can be assembled as follows. Referring to FIG. 27, the inner struts 1110 can be mounted on mandrel 1150, and then the outer struts 1120 can be placed over the inner struts 1110. The inner and outer struts are placed at a predetermined angle relative to each other to rotationally align the ears 1118 of the inner struts 1110 with the oblong openings 1124 of the outer struts 1120, which allows the projections to be inserted through the openings such that the ears 1118 can reside within the recessed portions 1126. Thereafter, the frame may be crimped slightly, causing the ears 1118 to become rotationally offset from the oblong openings 1124, thus locking the struts in place at each junction 1105, as depicted in FIG. 27. The actuators 1130 can then be mounted on the frame 1100. As noted above, the actuators 1130 desirably limit radial expansion of the frame so that the struts do not reach the angle at which the struts were assembled. For example, the actuators 1130 can be configured to limit radial expansion of the frame to the expanded configuration shown in FIG. 27. FIG. 28 shows a radially compressed state of the frame 1110, which can be the minimum diameter of the frame allowed by the actuators 1130. As shown, in the smallest compressed state allowed by the actuators, the ears 1118 are still rotationally offset from the oblong openings 1124 to prevent separation of the struts in the compressed state.

Figure 29:
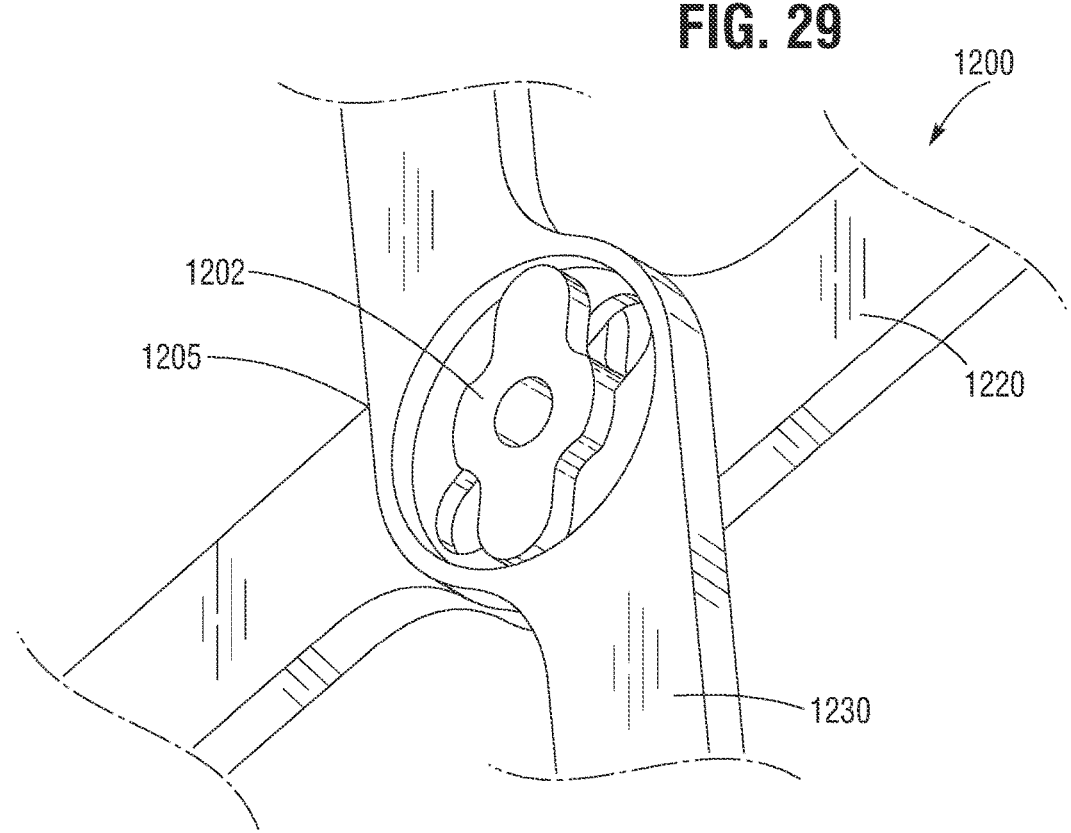
FIG. 29 is an enlarged, perspective view of an alternative embodiment of a hinge connection of a frame connected using separate hinges, such as shown in FIGS. 30A-33.

FIGS. 29-33 illustrate another embodiment of a hinge assembly 1200 for a prosthetic heart valve. As shown in FIG. 29, the hinge assembly 1200 in the illustrated embodiment is formed from an inner strut 1220 and an outer strut 1230 connected by a separate hinge member 1202 at a junction 1205. Hinge assembly 1200 is similar to the hinge shown in FIG. 22, except that in FIG. 22, the connector between the two struts is formed from an integral protrusion from one of the struts, which fits into an opening of the corresponding strut. In the embodiment shown in FIG. 29, the hinge assembly 1200 is formed using a separate hinge member 1202 that is not integral to either inner strut 1220 or outer strut 1230, as best shown in FIGS. 30-32B. It is understood that a plurality of such hinge assemblies may be used to form a frame, and that in alternative embodiments (not shown), rather than providing inner struts and outer struts, the struts may be interwoven, as in the embodiment of FIG. 13. It is further understood that while described as being first inserted through inner strut 1220, hinge member 1202 may be first inserted through outer strut 1230.

Figure 30A:
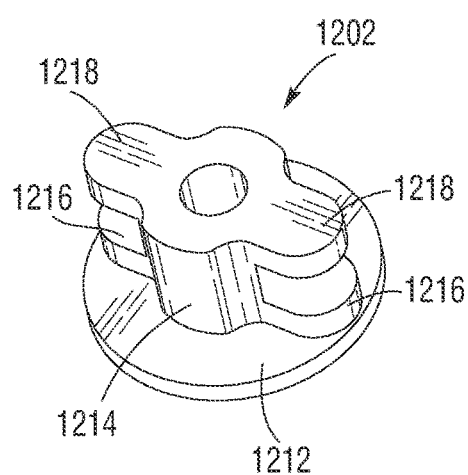
FIG. 30A is a perspective view of a hinge member that can be used to form a hinge connection between struts of a frame.
Figure 30B:
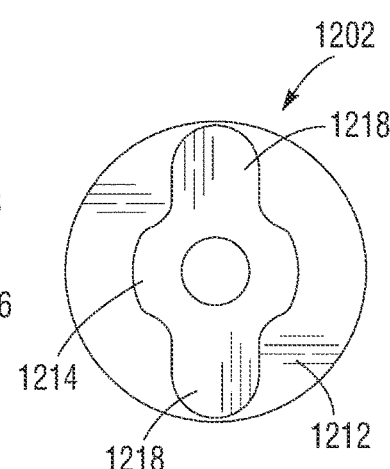
FIG. 30B is a plan view of the hinge member of FIG. 30A.
Figure 30C:
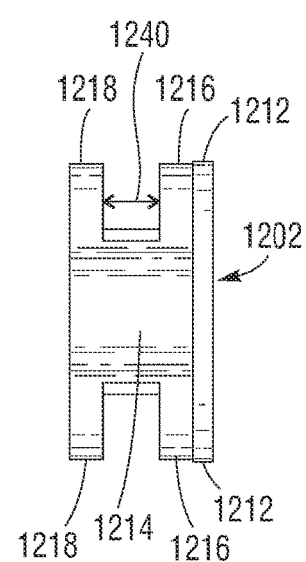
FIG. 30C is a side view of the hinge member of FIG. 30A.

As best shown in FIGS. 30A-30C, the hinge member 1202 may include a disc-shaped base 1212, from which a cylindrical projection 1214 extends. At a first end of the cylindrical projection adjacent the base 1212 are one or more retaining members in the form of a first set of one or more ears 1216 extending laterally from the cylindrical projection 1214. At a second end of the cylindrical projection (opposite the base 1212) are one or more locking members in the form of a second set of one or more ears 1218. In the illustrated embodiment, each set of ears 1216 and 1218, respectively, comprises two ears that extend in opposite directions from the cylindrical projection 1214, although more than two ears may be used in alternative embodiments.

An inner strut 1220 can be formed with a plurality of inner openings or apertures 1222 spaced along the length of the strut at the locations of junctions 1205 with an outer strut 1230, similar to the embodiment of frame 1100. As best shown in FIG. 31A, each inner opening 1222 can include two inner oblong side portions 1224 corresponding to the shape of the two sets of ears, 1216 and 1218. Each inner opening 1222 can be formed within an inner circular recessed portion 1226 formed on an inner surface of inner strut 1220, within which the disc-shaped base 1212 of hinge member 1202 may sit, as best shown in FIG. 32A. The depth of the inner circular recessed portion 1226 desirably is equal to or greater than the height of the disc-shaped base 1212 so that the hinge member 1202 does not extend radially beyond the inner surface of the inner strut 1220 when hinge frame assembly 1200 is assembled. As best shown in FIG. 32B, when the cylindrical projection 1214 and second set of ears 1218 of the hinge member 1202 are inserted through the inner opening 1222 of the inner strut 1220, the first set of ears 1216 are retained within the oblong side portions 1224 of the inner opening 1222, preventing axial and rotational movement of hinge member 1202 relative to the inner strut 1220.

An outer strut 1230 likewise can be formed with a plurality of outer openings or apertures 1232 spaced along the length of the strut at the locations of junctions 1205 with an inner strut 1220, similar to the embodiment of frame 1100. As best shown in FIG. 31B, each outer opening 1232 can include two outer oblong side portions 1234 corresponding to the shape of the second set of ears 1218. Each outer opening 1232 can be formed within an outer circular recessed portion 1236 formed on an outer surface of outer strut 1230, within which the second end of the cylindrical projection 1214 and the second set of ears 1218 can be retained, as best shown in FIG. 33, which shows the assembly configuration of the hinge frame assembly 1200. The depth of the outer circular recessed portion 1236 desirably is equal to or greater than the height of the second set of ears 1218 so that the hinge member 1202 does not extend radially beyond the outer surface of the outer strut 1230 when hinge frame assembly 1200 is assembled.

Once assembled on a frame, the cylindrical projection 1214 extends through a corresponding opening 1232 in the outer strut 1230, with the second set of ears 1218 residing in the outer recessed portion 1226 surrounding the opening. The portion of the outer strut 1230 surrounding the opening 1232 within the recessed portion 1236 resides within a gap 1240 (FIG. 30C) between the first set of ears 1216 and the second set of ears 1218, allowing the outer strut 1230 to pivot or rotate relative to the inner strut 1220 and the hinge member 1202. The second set of ears 1218 and the correspondingly shaped outer oblong side portions 1234 allow the second set of ears 1218 to be inserted through the outer oblong side portions 1234 during assembly when the second set of ears 1218 and the outer oblong side portions 1234 are rotationally aligned with each other and then prevent separation of the two struts 1220, 1230, when the second set of ears 1218 and the outer oblong side portions 1234 are rotationally offset or misaligned from each other.

During assembly, in a similar fashion as described above with regard to the embodiment of frame 1100, after the second set of ears 1218 of the hinge member 1202 are first inserted through an inner strut 1220, they are aligned with the outer oblong side portions 1234 of an opening 1232 of an outer strut 1230 corresponding to a predetermined angle between the struts 1220, 1230 which is greater than the maximum angle between the struts 1220, 1230 allowed by, e.g., actuators 1130 during radial expansion of the frame. Thus, once the second set of ears 1218 of hinge member 1202 are inserted through the corresponding openings 1224 and 1234 of both sets of struts to form a hinge of the frame, the struts are then rotated relative to each other, which causes the second set of ears 1218 to become offset from the outer oblong side portions 1234, as best shown in FIG. 29.

As with frame 1100, after assembling all of the hinges, actuators 1130 can then be mounted on the frame. The actuators 1130 are configured to radially expand and contract the frame, as noted above, but desirably limit the radial expansion and contraction of the frame within a predetermined range of diameters and a predetermined range of angles between the struts 1220, 1230 at which the second set of ears 1218 are still rotationally offset from the outer oblong side portions 1234.

For example, a frame diameter in the assembly configuration of FIG. 33 may be 29 mm, while the range of frame diameters between the minimum (crimped) diameter of the frame and the maximum allowable operational diameter of the frame may be between 8 mm and 28 mm, respectively. In this manner, the actuators 1130 can prevent radial expansion of the frame to a diameter at which the second set of ears 1218 are rotationally aligned with the outer oblong side portions 1234, thereby preventing separation of the struts 1210, 1230 at any of the junctions 1205. Similarly, the actuators 1130 can prevent radial contraction of the frame to a diameter at which the ears 1218 are rotationally aligned with the oblong side portions 1234, thereby preventing separation of the struts 1210, 1230 at any of the junctions 1205 when the frame is compressed to a delivery configuration. Additionally, once rotationally offset from the outer oblong side portions 1234, the second set of ears 1218 may interact with the outer surface of the outer strut 1230 to prevent radial movement of the hinge member 1202 relative to the struts 1220, 1230.

In this manner, the hinge assembly can be referred to as "self-locking" in that the mechanical engagement of the ears 1218 with the adjacent surface of the outer recessed portion 1236 locks the struts together at a junction 1105 and need not rely on placing the struts in tension against each other to retain a connection between the struts. Consequently, the struts need not be formed from super-elastic materials (e.g., Nitinol) to maximize tension on the struts. While the struts can be formed from super-elastic materials or non-super-elastic materials (e.g., stainless steel or cobalt chromium alloys), non-super-elastic materials are desirable in some embodiments because they can provide greater crush resistance and typically are less expensive than super-elastic materials. Additionally, providing separate hinge members may simplify the manufacturing process for the struts by eliminating the need to specially manufacture a strut having three dimensional hinge protrusions. This may reduce overall manufacturing costs.

The hinge assembly 1200 can comprise hinge members 1202 having features corresponding to openings in the struts wherein the features have any of various shapes in addition to those shown in the illustrated embodiment. In general, a hinge member can be formed with a locking member (e.g., ear 1218) that has a non-circular shape (in a plane perpendicular to the central axis of the hinge member) and the corresponding opening in the outer strut 1232 can have any non-circular shape that can be rotationally aligned with the locking member to permit assembly of the struts and then rotationally offset from the locking member to prevent separation of the struts at the hinge.

Similarly, a hinge member can be formed with a retaining member (e.g., ear 1216) that has a non-circular shape (in a plane perpendicular to the central axis of the hinge member) and the corresponding opening 1222 in the inner strut 1220 can have any non-circular shape that can be rotationally aligned with the retaining member to permit insertion of the hinge member through the opening 1222 and prevent rotation of the hinge member relative to the inner strut 1220. In alternative embodiments, the hinge member can be formed without features (e.g., ears 1216) that prevent relative rotation between the hinge member and the inner strut 1220.

In particular embodiments (not shown), a frame using a plurality of hinge assemblies 1200 can be assembled in a similar fashion to the frame 1100 shown in FIGS. 27 and 28. In such embodiments, the hinge members 1202 may first be inserted at each of the appropriate openings 1222 in the inner struts 1220, as shown in FIGS. 31A-32B prior to mounting them on a mandrel 1150, as described above. Thereafter, the outer struts 1230 can be mounted over the inner struts 1220 and assembly can continue in a manner similar to that described with reference to FIGS. 27 and 28. As noted briefly above, in other embodiments, the hinge members 1202 can be inserted through the struts 1220, 1230 in the opposite direction, such that the base 1212 of each hinge member is adjacent an outer surface of an outer strut and the ears 1218 are adjacent an inner surface of an inner strut.

FIGS. 34-37 illustrate a flanged rivet or connector 1300 that can be used to interconnect struts of a frame of a prosthetic heart valve, according to another embodiment. Referring to FIG. 34, in the illustrated embodiment the rivet 1300 comprises two elongated cylindrical end portions 1302, 1304 separated by a wide central portion or flange 1306. Additionally, a cylindrically shaped, axially extending opening or bore 1308 can extend completely though the rivet 1300.

FIG. 35A is a perspective view of a frame 1400, according to one embodiment, that can be assembled using flanged rivets 1300. The frame 1400 in the illustrated embodiment comprises a plurality of first, inner struts 1410 connected to a plurality of second, outer struts 1420. The frame 1400 can have a construction similar to the frame 200 of FIG. 4, except for the configuration of the hinged connections between the struts. Each strut 1410, 1420 can be formed with a plurality of apertures 1402 at the locations where the struts overlap each other, as previously described in connection with the frame 200. Additionally, as shown in greater detail in FIG. 36, each of the apertures 1402 can include a counter-bore or enlarged recessed portion 1412, 1422 as previously described in FIG. 3B, that is sized to receive one of the two elongated end portions 1302, 1304, respectively, both in an initial configuration, and in a second configuration following the deformation of the two elongated end portions 1302, 1304, as will be further described herein.

As shown in FIGS. 35B and 36, in an initial (non-deformed) configuration, the wide flange 1306 of the flanged rivet 1300 is placed between a first inner strut 1410 and a first outer strut 1420 at their apertures 1402. In this initial configuration, the radially innermost terminal end of the end portion 1302 can extend beyond the inner surface of the inner strut 1410. Similarly, the radially outermost end of the end portion 1304 can extend beyond the outer surface of the outer strut 1420.

As shown in FIG. 37, in a second configuration, the end portions 1302, 1304 are deformed, such as by plastic deformation, so as to form end flanges 1312, 1314 at the opposing ends of the rivet. Each end flange has a diameter that is greater than that of the aperture 1402 in the adjacent strut 1410, 1420. Desirably, at least one of the end flanges is not seated tightly against the adjacent surface of the adjacent strut, allowing at least one of the struts to pivot freely relative to the rivet and the other strut.

In particular embodiments, the end flanges can each be received entirely within the enlarged recessed portions 1412, 1422 of the adjacent struts 1410, 1420. For example, the end flange 1312 formed by end portion 1302 can be flush with the inner surface of the inner strut 1410 and the end flange 1314 formed by end portion 1304 can be flush with the outer surface of the outer strut 1420. In this manner, the flanged rivets 1300 do not increase or contribute to the overall crimp profile of the prosthetic valve and do not interfere with or place undue stresses on the delivery sheath of the valve (e.g., sheath 82 in FIG. 1).

The end portions 1302, 1304 may be deformed simultaneously, or may be deformed separately. For example, the end portions 1302, 1304 can be deformed by applying axially directed compressive forces on the opposite ends of the rivet and/or by applying radially outwardly directed forces within the bore 1308 (e.g., using a swaging tool) to cause the end portions 1302, 1304 to deform to the shape shown in FIG. 37. In one alternative embodiment (not shown), rather than placing the rivet 1300 between two struts in an initial configuration, the end portion 1302 of the rivet 1300 may be inserted through an aperture 1402 in a first, inner strut 1410 and the first end portion 1302 may be deformed to form the end flange 1312, so that the rivet 1300 is effectively retained by the first, inner strut 1410. Subsequently, the first, inner strut 1410 can be connected to a second, outer strut 1420 by inserting the second end portion 1304 of the same rivet 1300 through the opening in the outer strut and deforming the second end portion 1304 to form end flange 1314. In still another alternative embodiment, a rivet 1300 may first be connected to an outer strut 1420 in a similar manner before the outer strut is connected to an inner strut 1410.

Providing flanged rivets such as those described in this disclosure may provide benefits to both safety and ease of assembly. Since the rivet is held between struts, this may reduce the risk of separation of the rivet from the struts. Additionally, in embodiments where the rivet is pre-mounted to a strut, this may simplify assembly by holding the rivet in place while it is mounted to the corresponding strut. Additionally, manufacturing the struts separately from the rivets may minimize the cost for manufacturing the struts by allowing them to be manufactured from a flat sheet, while also enabling optimization of the engineering for these separate components (i.e., the rivets and the struts), which serve different functions and may require different mechanical properties.

Figure 38A:
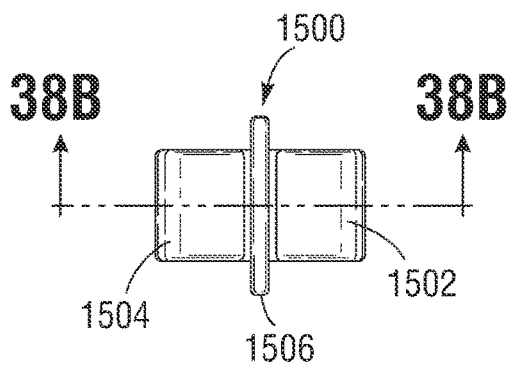
FIG. 38A is a side view of another embodiment of a flanged rivet that can be used to form a hinge connection between the struts of a frame.
Figure 38B:
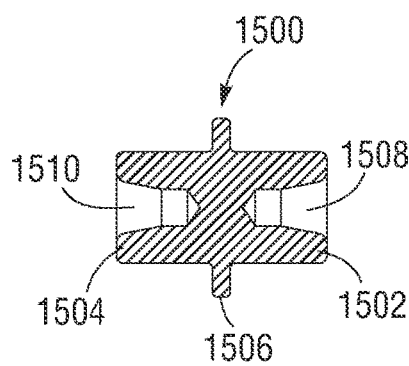
FIG. 38B is a cross-sectional view of the flanged rivet of FIG. 38A taken along line 38B-38B of FIG. 38A, showing drilled holes in its ends.
Figure 39:
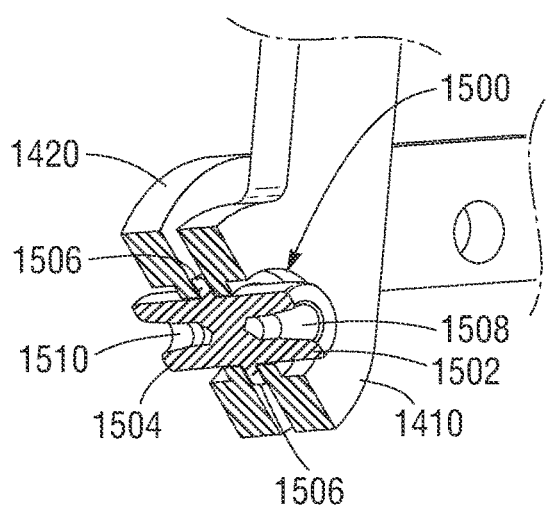
FIG. 39 is a cross-sectional view of a hinge formed by two overlapping struts using the flanged rivet of FIGS. 38A and 38B.

FIGS. 38A, 38B and 39 show another embodiment of a flanged rivet 1500 formed by drilling or otherwise forming first and second blind holes 1508, 1510, in first and second end portions 1502, 1504 of the rivet. The rivet 1500 can have a wide flange or central portion 1506 intermediate the end portions. The rivet 1500 can be assembled on two struts 1410, 1420 as previously described by deformed end portions 1502, 1504.

Figure 40A:
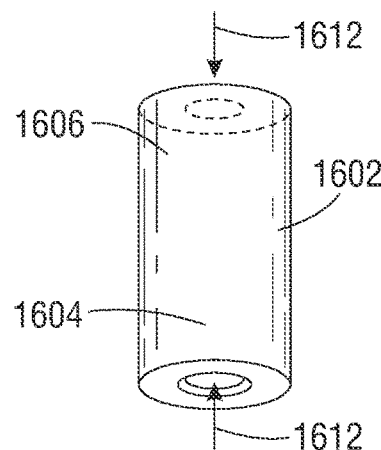
FIG. 40A is a perspective view of a tubular member used to form a rivet.
Figure 40B:
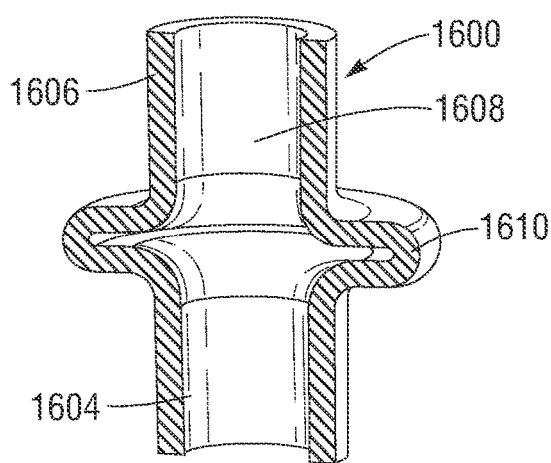
FIG. 40B is a cross-sectional view of a flanged rivet formed from the tubular member of FIG. 40A.
Figure 40C:
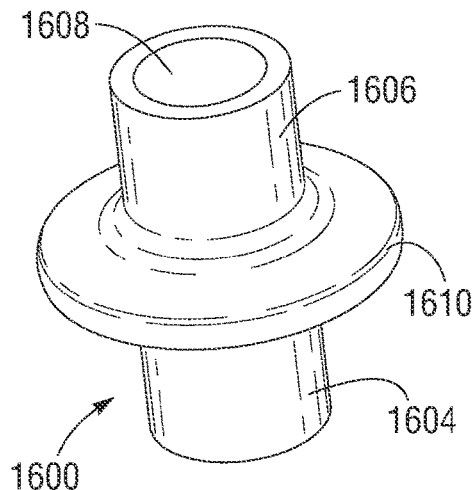
FIG. 40C is a perspective view of the flanged rivet embodiment of FIG. 40B.

FIGS. 40A-40C show another embodiment of a flanged rivet 1600, formed by deforming a simple tube or cylindrical member 1602 (FIG. 40A) having first and second end portions 1604, 1606, respectively, and a longitudinal opening or bore 1608 extending therethrough. Compressive forces can be applied to the opposing ends of the tube 1602 (indicated by arrows 1612), causing the tube to plastically deform and form a central portion or flange 1610 between the first and second end portions 1604, 1606. The rivet 1600 may be assembled on two struts 1410, 1420 as previously described by deforming the end portions 1604, 1606.

Figure 41:
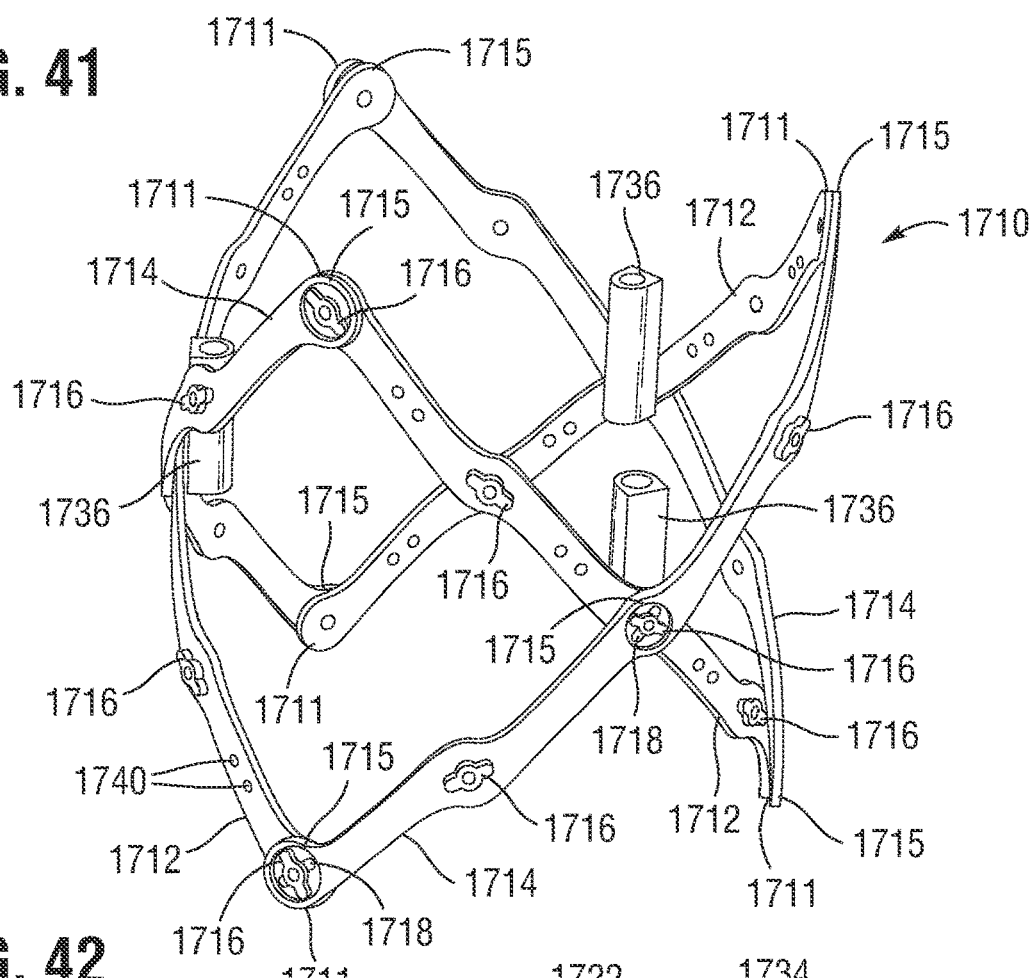
FIG. 41 is a perspective view of an embodiment of an inner frame sub-assembly for a prosthetic valve.
Figure 42:
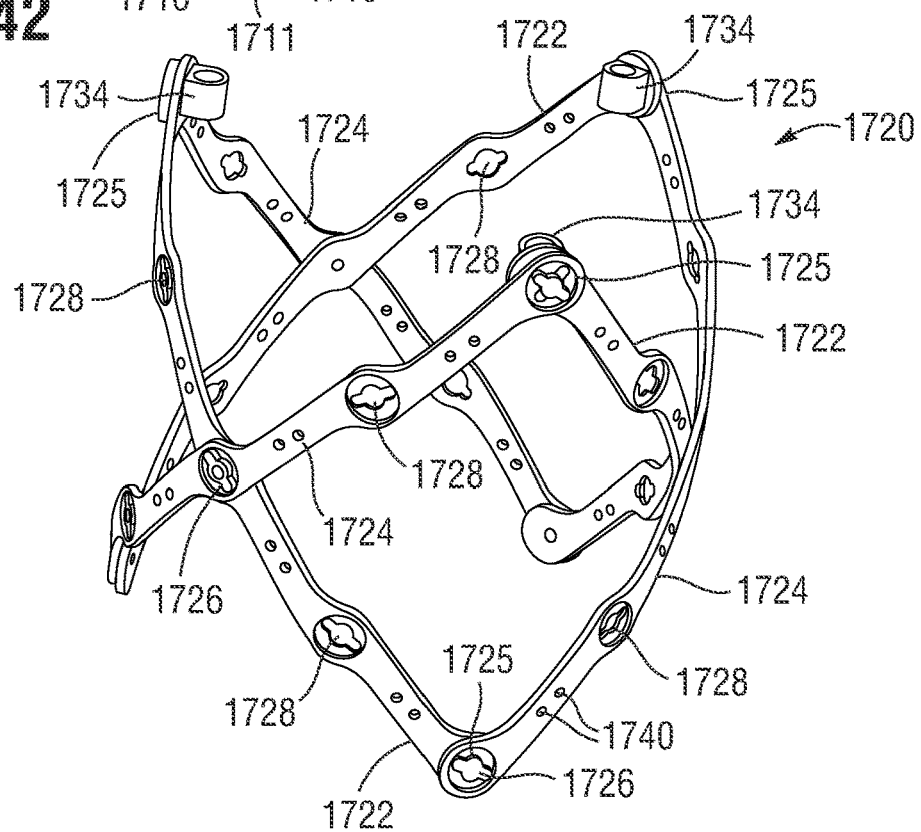
FIG. 42 is a perspective view of an embodiment of an outer frame sub-assembly for a prosthetic valve.
Figure 43:
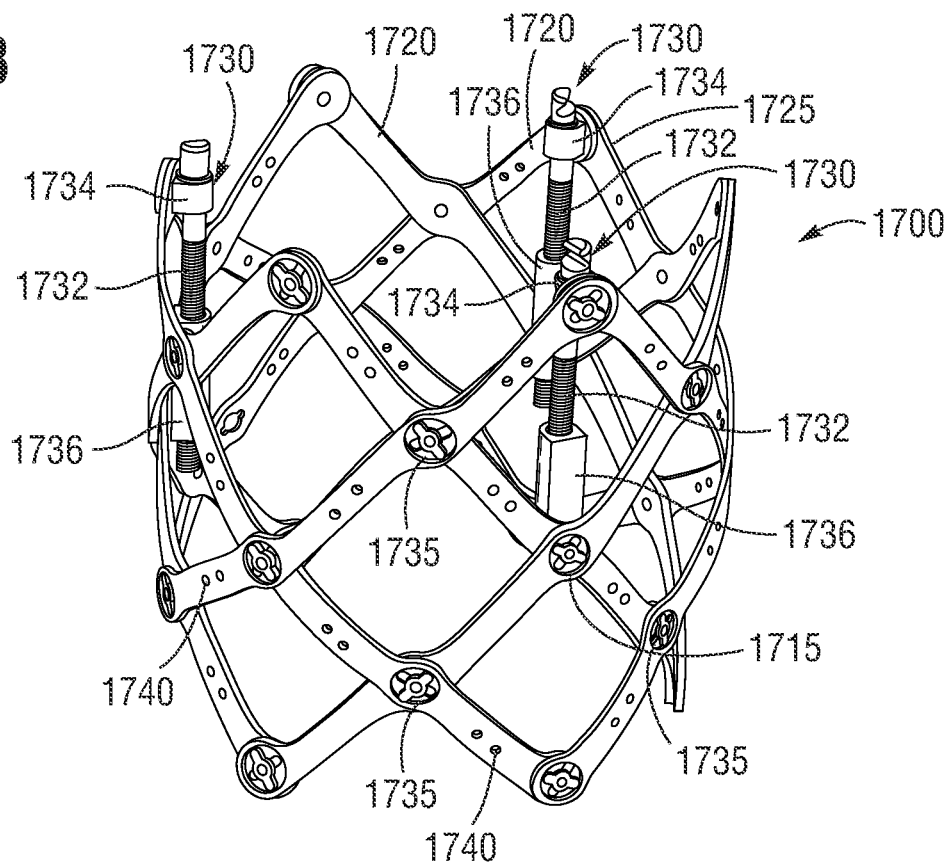
FIG. 43 is a perspective view of a frame for a prosthetic valve formed by assembling the inner frame sub-assembly of FIG. 41 and the outer frame sub-assembly of FIG. 42, and mounting threaded actuators thereon for frame expansion.

FIGS. 41-44 illustrate the assembly of another embodiment of a frame 1700 for a prosthetic heart valve. As shown in FIG. 43, the frame 1700 in the illustrated embodiment is formed from at least two separate frame sub-assemblies, including a first, inner frame sub-assembly 1710 (shown in FIG. 41), and a second, outer frame sub-assembly 1720

(shown in FIG. 42), as further described herein. The two frame sub-assemblies may be further connected to each other and expanded using a plurality of actuators 1730, also described in more detail herein. In other embodiments, the frame 1700 can include additional frame sub-assemblies positioned radially inward and/or radially outward of frame sub-assemblies 1710, 1720.

Similar to frame 1100 shown in FIG. 21, the inner frame sub-assembly 1710, best illustrated in FIG. 41, may comprise a plurality of inner struts 1712 and a plurality of outer struts 1714 connected by hinge projections 1716 passing through apertures 1718 at junctions 1715. In alternative embodiments (not shown), the struts may be interwoven, as in the embodiment of FIG. 13. In other alternative embodiments, rather than using integral projections and apertures, inner struts 1712 and outer struts 1714 may be assembled using rivets at apices 1711, and/or by using rivets at some or all of the junctions 1715. In some embodiments, a separate hinge, such as shown in FIGS. 30A-33, or other separate hinges, such as shown in FIGS. 34-40C, or other suitable separate hinges may be used.

The components forming the hinge projections 1716 can be integrated into the construction of the struts. As best shown in FIG. 41, for example, three inner struts 1712 and three outer struts 1714 each comprises a plurality of integral hinge projections 1716 spaced along the length of the strut, including at the locations of the junctions 1715, which may be similar to the hinge projections 1112 illustrated in FIG. 25. Additional hinge projections 1716 may be provided at additional locations along the struts, which may be used to join the inner frame sub-assembly 1710 to the outer frame sub-assembly 1720 at junctions 1735. Outer struts 1714 can further each be formed with a plurality of openings or apertures 1718 spaced along the length of the strut at the locations of the junctions 1715, which may be similar to apertures 1122, as illustrated in FIG. 24, which may be used to join the inner struts 1710 to the outer struts 1714 by a process similar to that described above with regard to frame 1100.

Similar to the inner frame sub-assembly 1710, the outer frame sub-assembly 1720, best illustrated in FIG. 42 may comprise a plurality of inner struts 1722 and a plurality of outer struts 1724 connected by hinge projections 1726 of the inner struts 1722 passing through apertures 1728 of the outer struts 1724 at junctions 1725. In alternative embodiments (not shown), the struts may be interwoven, as in the embodiment of FIG. 13. In other alternative embodiments, rather than using integral hinges and apertures, inner struts 1722 and outer struts 1724 may be assembled using rivets or the other connection mechanisms described herein and in the incorporated patents and applications at apices 1711, and/or at some or all of the junctions 1725. In some embodiments, a separate hinge, such as shown in FIGS. 30A-33, or other separate hinges, such as shown in FIGS. 34-40C, or other suitable separate hinges may be used.

The components forming the hinge projections 1726 can be integrated into the construction of the struts. As best shown in FIG. 42, for example, three inner struts 1722 and three outer struts 1724 each comprises a plurality of integral hinge projections 1726 spaced along the length of the strut, including at the locations of the junctions 1725, which may be similar to the hinge projections 1112 illustrated in FIG. 25. Outer struts 1724 can further each be formed with a plurality of openings or apertures 1728 spaced along the length of the strut at the locations of the junctions 1725, which may be similar to apertures 1122, as illustrated in FIG. 24, which may be used to join the inner struts 1722 to the outer struts 1724 by a process similar to that described above with regard to frame 1100. Additional apertures 1728 may be provided at additional locations along the struts, which may be used to join the outer frame sub-assembly 1720 to the inner frame sub-assembly 1710 at junctions 1735.

Figure 44:
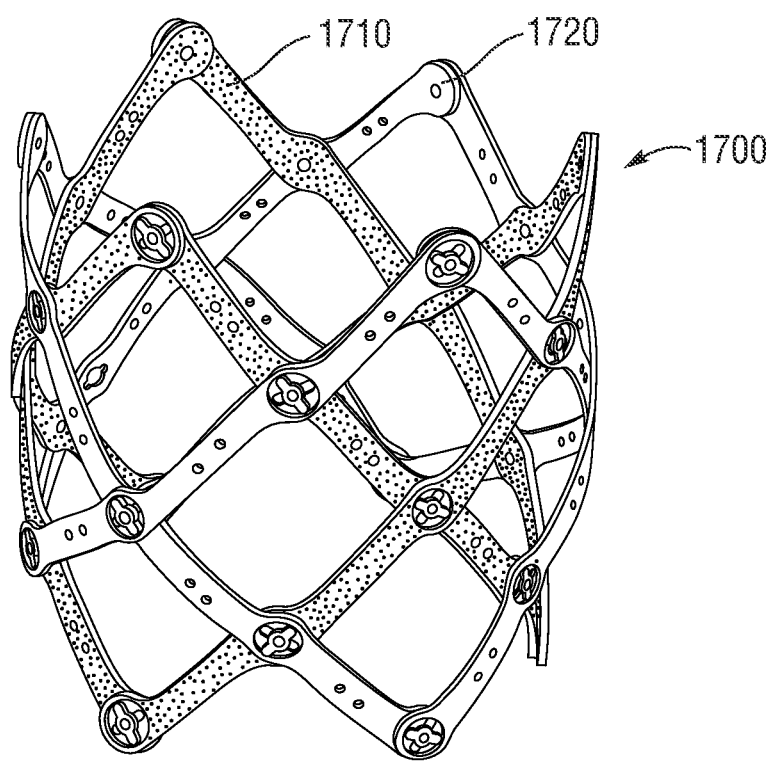
FIG. 44 is a perspective view of the frame of FIG. 43, shown without the actuators.

The struts of each of the sub-assemblies are arranged to form a plurality of closed cells (each sub-assembly in the illustrated embodiment forms three diamond-shaped cells), which helps retain their pre-assembled annular shape prior to being attached to each other. Once separately assembled as shown in FIGS. 41 and 42, the inner frame sub-assembly 1710 can be inserted into outer frame sub-assembly 1720, such as with the frames rotated by a half cell shift (in this case, 60 degrees), and joined at junctions 1735 by inserting the hinge projections 1716 on the struts 1712, 1714 of the inner frame sub-assembly 1710 through the corresponding apertures 1728 of the struts 1722, 1724 of the outer frame sub-assembly 1720, as illustrated in FIG. 43. FIG. 44 shows the assembled frame 1700 with stippling added to the struts of the inner frame sub-assembly 1710 for purposes of illustration only. The stippling is added to distinguish the inner frame sub-assembly 1710 from the outer frame sub-assembly 1720 and does not represent actual surface ornamentation.

Alternatively, hinge projections on the outer frame assembly may be inserted through apertures on inner frame assembly (in embodiments where hinge projections extend radially inwardly from the struts to which they are connected). Or, separate rivets or other connection mechanisms, such as those described herein and in the incorporated patents and applications, may pass through apertures on both sub-assemblies at the junctions. Or, a combination of suitable connection mechanisms, including those described herein, may be used.

One or more of the struts 1712, 1714 of the inner frame sub-assembly 1710 and one or more of the struts 1722, 1724 of the outer frame sub-assembly 1720 can be formed with openings or apertures 1740 spaced along the length of the struts. The apertures 1740 can be used to suture leaflets, an inner skirt, and/or an outer skirt to selected struts of the frame, as further described below.

The frame 1700 can include a plurality of actuators, which may be threaded actuators 1730 configured to radially expand and contract the frame and retain the frame in an expanded shape when deployed inside a patient's body. Each actuator 1730 can include an inner member in the form of a screw 1732, which may comprise external threads, and which extends through a first outer member, sleeve, or cylinder 1734 positioned at a junction 1725 at one end of the outer frame sub-assembly 1720, and into a second outer member, sleeve, or cylinder 1736 that may be positioned at a junction 1715 on the inner frame sub-assembly 1710. One or both of these outer members 1734, 1736 may have internal threads to threadably engage the inner member 1732. Also, the outer members 1734, 1736 can be mounted at other locations on the frame 1700. For example, the first outer member 1734 can be mounted on the inner frame sub-assembly 1710 and the second outer member 1736 can be mounted on the outer frame sub-assembly 1720; or alternatively, both outer members 1734, 1736 can be mounted on the inner frame sub-assembly 1710 or both outer members 1734, 1736 can be mounted on the outer frame sub-assembly 1720.

Rotational movement of the inner member 1732 relative to the outer members 1734, 1736 is effective to radially expand and compress the frame 1700. The actuators 1730 can be releasably connected to corresponding actuators of a delivery apparatus, for example, each screw 1732 can be releasably connected to a corresponding drive shaft or drive wire of the delivery apparatus. Further details of the actuators 1730 are disclosed in co-pending application Ser. No. 15/831,197, filed Dec. 4, 2017, which is incorporated by reference in its entirety herein. In other embodiments, the actuators for radially expanding and compressing the frame 1700 can be push-pull type actuators as previously described in connection with the embodiments of FIGS. 1, 8, 12 and 21.

In the assembled state of the frame 1700, a plurality of the hinge projections 1716, 1726 extend through corresponding apertures 1718, 1728. During assembly, the projections are aligned with the apertures, and then the struts are rotated relative to one another, which causes the projections to rotate relative to the apertures, as described above in connection with the method of assembly of frame 1100 described with reference to FIGS. 27-28, securing the struts of the inner frame sub-assembly and the outer frame sub-assembly together. While in an alternative embodiment, not all junctions between the struts may have hinge projections inserted through apertures, the inner and outer struts of each frame sub-assembly are connected at least at the apices, e.g., apices 1711 of the inner frame sub-assembly, best illustrated in FIG. 41.

After assembling the frame 1700, the actuators 1730 can then be mounted on the frame. In other embodiments, the outer sleeves 1734, 1736 of the actuators can be mounted on the frame sub-assemblies 1720, 1710, respectively, prior to assembling the inner and outer frame sub-assemblies, and the screws 1732 are added after assembling the inner and outer frame sub-assemblies. The actuators 1730 are configured to radially expand and compress the frame, as noted above, but desirably limit the radial expansion and compression of the frame within a predetermined range of diameters and a predetermined range of angles between the struts of the inner frame sub-assembly 1710 and the struts of the outer frame sub-assembly 1720 so as to prevent separation of the two subassemblies at the junctions 1735, similar to the process described above with regard to frame 1100, making frame 1700 a "self-locking" frame assembly.

Soft components of the prosthetic valve, such as valve leaflets or an inner skirt may (not shown), can be added to the inner frame sub-assembly 1710, while other soft components, such as an outer skirt (not shown) can be added to the outer frame sub-assembly 1720. In particular embodiments, the valve leaflets and/or an inner skirt can be mounted or assembled on the inner frame sub-assembly 1710 and/or an outer skirt can be mounted or assembled on the outer frame sub-assembly 1720 before the inner frame sub-assembly 1710 and the outer frame sub-assembly 1720 are connected to each other to form the fully assembled frame 1700. Forming separate inner and outer frame sub-assemblies is advantageous in that is facilitates the assembly of the leaflets and/or the skirt(s) of the prosthetic valve, as further described below. Additional details regarding the assembly of soft components to a frame sub-assembly are described below. In alternative embodiments, the frame 1700 can be fully assembled prior to assembling the leaflets and the skirt(s) to the frame 1700.

Figure 45:
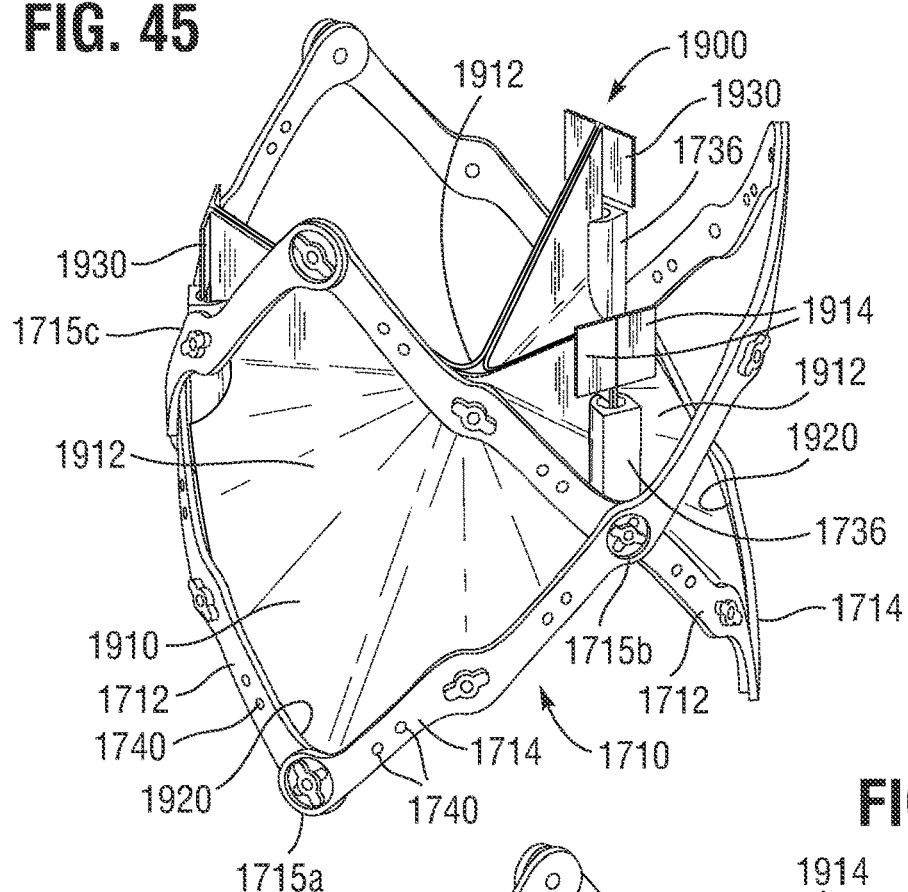
FIG. 45 is a perspective view of a valve sub-assembly comprising the inner frame sub-assembly of FIG. 41 and a prosthetic valve leaflet assembly.
Figure 46:
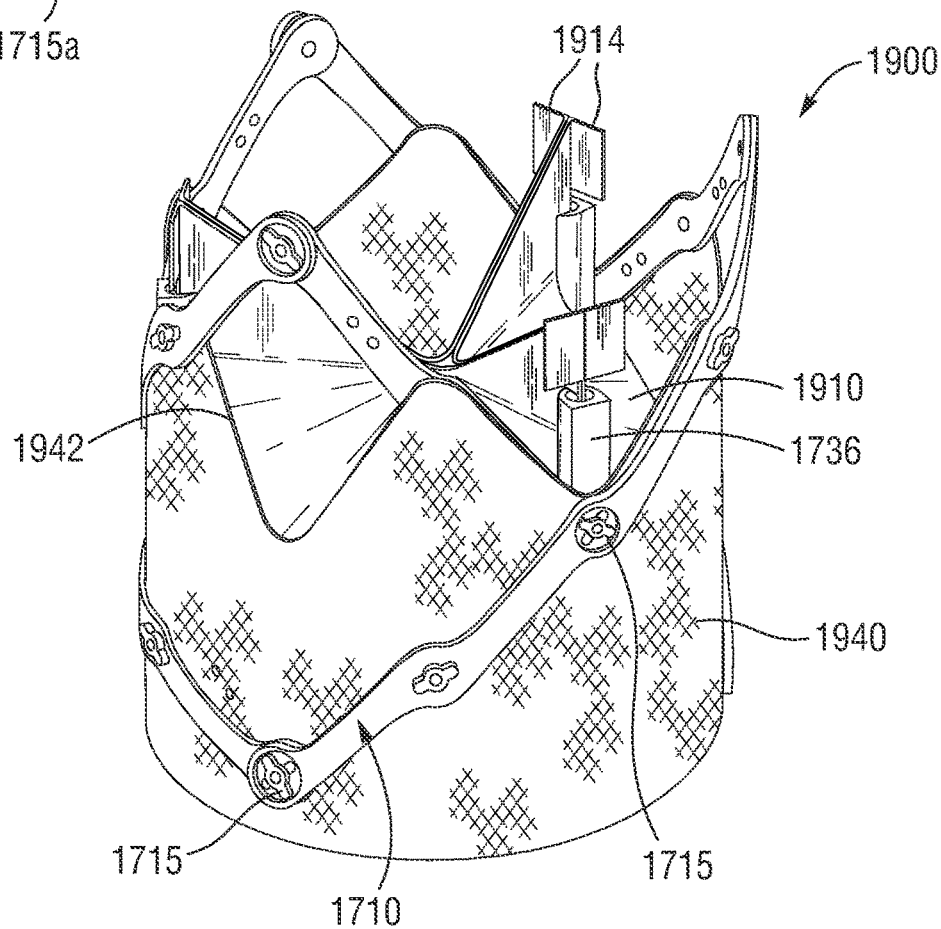
FIG. 46 is a perspective view of another valve sub-assembly comprising the inner frame sub-assembly of FIG. 41, a prosthetic valve leaflet assembly and a skirt positioned between the struts of the inner frame sub-assembly.
Figure 47:
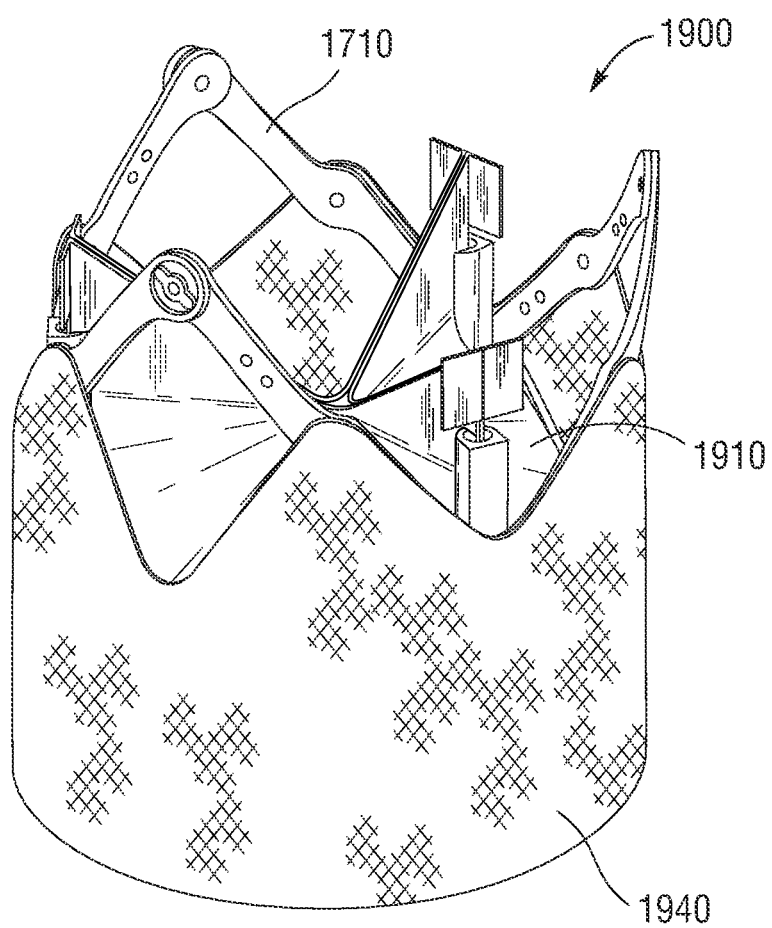
FIG. 47 is a perspective view of another valve sub-assembly comprising the inner frame sub-assembly of FIG. 41, a prosthetic valve leaflet assembly and a skirt positioned entirely external to the inner frame sub-assembly.

FIGS. 45-47 illustrate a valve sub-assembly 1900, according to another embodiment. As shown in FIG. 45, the valve sub-assembly 1900 comprises an inner frame sub-assembly 1710 and a prosthetic valve leaflet assembly 1910 at least partially mounted on the inner frame-sub assembly 1710. An external frame sub-assembly 1720 can be placed around the inner frame sub-assembly 1710 as previously described in connection with FIGS. 43-44.

The valve leaflet assembly may comprise three leaflets 1912 (as in the illustrated embodiment), although it is to be understood that other numbers of leaflets may be used. Each leaflet 1912 can be formed with commissure tabs 1914 on opposite sides of the leaflet. Each commissure tab 1914 can be paired with an adjacent commissure tab 1914 of an adjacent leaflet to form a commissure 1930. The commissures 1930 can be attached, for example, to struts of an outer frame sub-assembly 1720 or to components of the actuators 1730 (e.g., to the sleeves 1736). Further details regarding mounting the commissures 1930 of the leaflets to the frame are disclosed in U.S. Provisional Application Nos. 62/506,430, filed May 15, 2017 and 62/614,299, filed Jan. 5, 2018, and U.S. application Ser. No. 15/978,459, filed May 14, 2018, which are incorporated herein by reference.

The lower or inflow portion of the leaflets may comprise scalloped inflow or cusp edges 1920 that may be attached, such as by suturing or other suitable techniques, to the lower portions of inner struts 1712 and outer struts 1714. For example, the inflow edges 1920 can be stitched to the struts 1712, 1714 with sutures passing through the leaflets and openings 1740 in the struts 1712, 1714, such as using in-and-out stitching or whip stitching extending along the struts. Alternatively, the sutures can pass through the leaflets and around the struts 1712, 1714. An inner skirt 1940 (discussed further below) can be used to reinforce the attachment of the inflow edges 1920 of the leaflets to the struts 1712, 1714. One or more narrow reinforcing strips (e.g., a narrow strip of fabric) can be placed along the cusp edge 1920 of each leaflet and sutured thereto to reinforce the connection of the cusp edge with the struts. For example, the cusp edges 1920 can be "sandwiched" or disposed between two reinforcing strips that can be sutured to each other and to the cusp edges.

Because the inflow edges 1920 of the leaflets 1912 in the illustrated embodiment are attached solely to the inner frame sub-assembly 1710, the secured leaflet edges need not pass over a "crossing strut." In other words, each inflow edge 1920 of a leaflet is secured along a length of two struts where the two struts do not cross another strut at a junction 1715. As best shown in FIG. 45, in the illustrated embodiment, each inflow edge 1920 is secured to a first strut 1712 and a second strut 1714 along the lower halves of the struts between a junction 1715*a* at an apex formed by the intersection of the struts 1712, 1714 and junctions 1715*b*, 1715*c* formed by the intersection of each strut 1712, 1714 with an adjacent crossing strut without passing over the junctions 1715*b*, 1715*c*. Further, when the outer frame 1720 sub-assembly is attached to the inner frame sub-assembly 1710 in the manner shown in FIGS. 43-44, the outer frame sub-assembly 1720 is entirely external to the connection between the inflow edges of the leaflets such that the struts of the outer frame sub-assembly need not be used for attachment of the inflow edges 1920 of the leaflets.

Avoiding attachment of the inflow edges of the leaflets to any crossing struts provides a more secure leaflet connection, with less stress on the leaflets between the inflow edges 1920 and the commissure tabs 1912. In addition, this manner of connecting the leaflets to the struts provides reduces the risk of leaflet abrasion and a symmetric and smooth attachment line to improve valve performance. Moreover, it is relatively easier to secure the leaflets to the struts 1712, 1714 prior to fully assembling the frame by virtue of the fact that inner frame sub-assembly has less struts than a fully formed frame and therefore there is much greater access to the interior of the frame for the assembler to insert tools and their fingers into the frame during the assembly process. This can greatly simply the process of stitching the leaflets to the struts and/or to any reinforcing strips or skirts.

FIG. 46 shows one way of mounting an inner skirt 1940 to the valve sub-assembly 1900. In the illustrated embodiment, the inner skirt 1940 is "sandwiched" or disposed between the inner struts 1712 and outer struts 1714 of the inner frame sub-assembly 1710. As such, the connection of the inner struts 1712 and outer struts 1714 at junctions 1715 may be used to help secure the skirt to the inner frame sub-assembly 1710, such as by passing the projections 1716 through corresponding slits or openings in the skirt. The skirt 1940 can be further secured to the struts 1712, 1714 with sutures that pass through the skirt and through apertures 1740 of selected struts 1712, 1714 (and/or around selected struts 1712, 1714). The skirt 1940 can be formed with an undulating outflow edge 1942 that is shaped to correspond with the shape a circumferentially extending row of strut segments adjacent the row of strut segments defining the outflow end of the frame assembly.

In another embodiment, as illustrated in FIG. 47, an inner skirt 1940 is mounted entirely external to the inner frame sub-assembly 1710. The skirt 1940 can be secured to the struts 1712, 1714 of the inner frame sub-assembly 1710 with sutures extending through apertures 1740 and/or around selected struts of the inner frame sub-assembly 1710.

Figure 48:
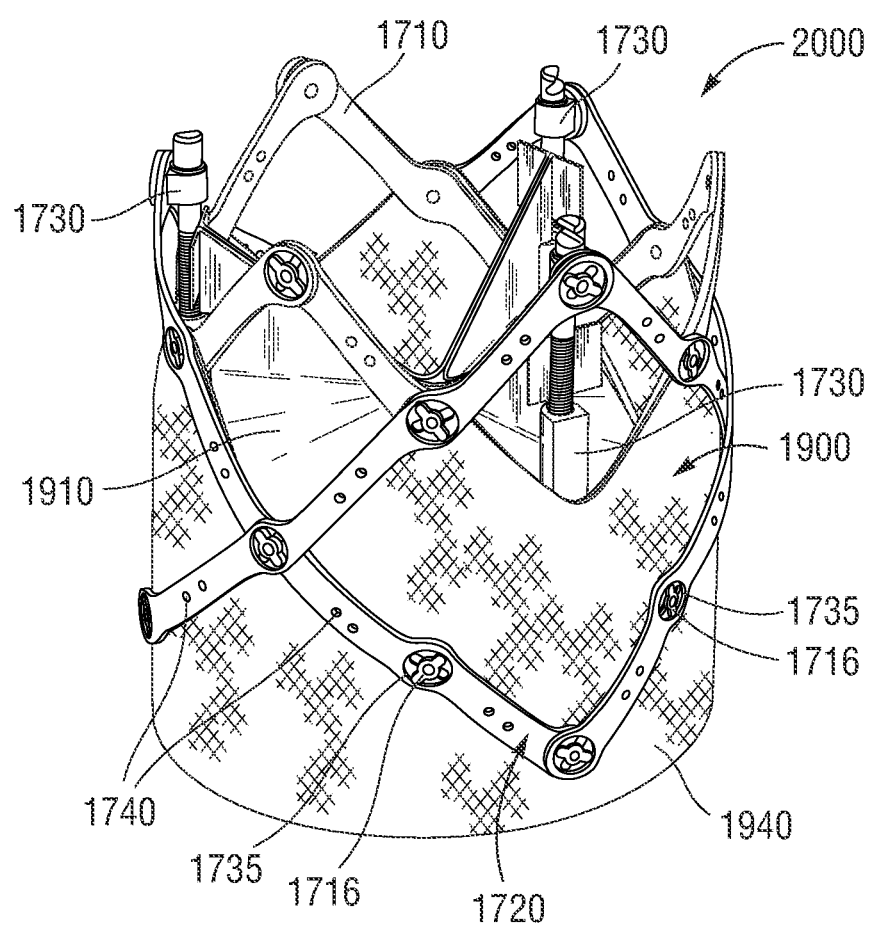
FIG. 48 is a perspective view of a valve assembly formed by combining the valve sub-assembly of FIG. 47 with the outer frame sub-assembly of FIG. 42, providing threaded actuators for frame expansion.

FIG. 48 illustrates another exemplary prosthetic valve 2000. The prosthetic valve 2000 may be formed by first assembling the valve sub-assembly 1900 of FIG. 47, with an inner skirt 1940 provided entirely external to the inner frame sub-assembly 1710. An outer frame assembly 1720 can then be formed and placed around the skirt 1940 and secured to the inner frame sub-assembly 1710 as previously described in connection with FIGS. 43-44, except that the connection between the inner frame sub-assembly 1710 and the outer frame sub-assembly 1720 at junctions 1735 may be used to secure the inner skirt 1940 to the frame 1700 in lieu of or in addition to sutures that are used to secure the skirt 1940 to the struts of the frame. In particular, the skirt 1940 can be retained in place by inserting the projections 1716 of the inner frame sub-assembly 1710 that extend through apertures 1728 of the outer frame sub-assembly 1720 through slits or openings in the skirt. In this manner, selected projections 1716 of the inner frame sub-assembly 1710 extend through respective slits or openings in the skirt 1940 and through respective openings 1728 in the outer frame sub-assembly 1720.

In alternative embodiments where separate rivets or hinge members are used in lieu of integral projections 1716 (e.g., such as shown in FIGS. 29-40), one or more rivets or hinge members can extend through an opening in a strut of the inner frame sub-assembly 1710, through a slit or opening in the skirt 940, and through an opening in a strut of the outer frame sub-assembly 1720.

In this way, the inner skirt 1940 can be sandwiched or held between inner and outer struts of the inner frame sub-assembly 1710 (FIG. 46) or between the inner frame sub-assembly 1710 and the outer frame sub-assembly 1720 (FIG. 48) to provide a strong, durable connection for the inner skirt 1940. In still other embodiments, the skirt 1940 can be disposed between the inner and outer struts of the outer frame sub-assembly 1720 and held in place with the projections of the inner struts extending though the slits or openings of the skirt.

This form of connecting the skirt to the frame can simplify the assembly process, potentially reducing the amount of stitching by using the projections, rivets, hinges, or other connection mechanisms themselves to connect the skirt to the struts of the frame. In particular, positioning the skirt 1940 between the inner and outer frame sub-assemblies 1710, 1720 after forming each of the frame sub-assemblies can save considerable time in assembling the entire valve. Additionally, in some embodiments, the entire skirt can be secured to the frame via the projections on the struts (or other hinge mechanisms) without the use of sutures. Additionally, using the relative position of the projections, rivets, hinges, or other connection mechanisms to secure the two frame sub-assemblies at the junctions 1735, as well as to connect the inner skirt 1940 to the frame sub-assemblies, allows these connection mechanisms at junctions 1735 to serve as self-alignment features for the frame components and soft components, as each projection (or other hinge member) aligns with a pre-formed slit or opening in the soft component (e.g., skirt 1940). In other words, the spacing and positioning of the pre-formed slits or openings in the soft components corresponds to the spacing and positioning of the projections on the struts to facilitate proper positioning of the soft component relative to the frame struts during the assembly process.

The prosthetic valve 2000 can further include an outer skirt (not shown) that can be positioned entirely outside of the outer frame sub-assembly 1720. The outer skirt can be secure to the frame using sutures and/or hinge members that secure the inner and outer struts of the outer frame sub-assembly 1720.

Still another advantage provided by the prosthetic valve 2000 is that, with the outer frame sub-assembly 1720 assembled separately and positioned completely external to the inner frame sub-assembly 1710, the struts facing the articulating portions of the leaflets (e.g., the struts located at positions where the leaflets of valve leaflet assembly move toward and away from the frame) are part of the outer frame sub-assembly 1720. This creates a gap between the articulating portions of the leaflets (especially the coaptation edges) so as to prevent or minimize contact between the leaflets and the frame during operation of the prosthetic valve, thereby protecting against leaflet abrasion. This can also allow for use of a relatively larger leaflet for improved hemodynamics.

In alternative embodiments, the leaflets 1912 or portions thereof can be secured to the struts of the frame in a similar manner using one or more hinge members that extend through the leaflets and two overlapping struts in lieu of or in addition to suture attachment of the leaflets. In one implementation, for example, the inflow edges 1920 of the leaflets can be positioned against the inner surfaces of struts 1712, 1714 a held in place with hinge members (e.g., rivets) that extend through a leaflet, a strut 1712, 1714 and a strut 1722, 1724 of the outer frame. In another implementation, the leaflets 1912 can be placed between the inner and outer struts 1712, 1714 at junctions 1715*a*, 1715*b*, 1715*c* and retained in place via the projections 1716 (or other hinge members) that interconnect the struts at those junctions.

Figure 49:
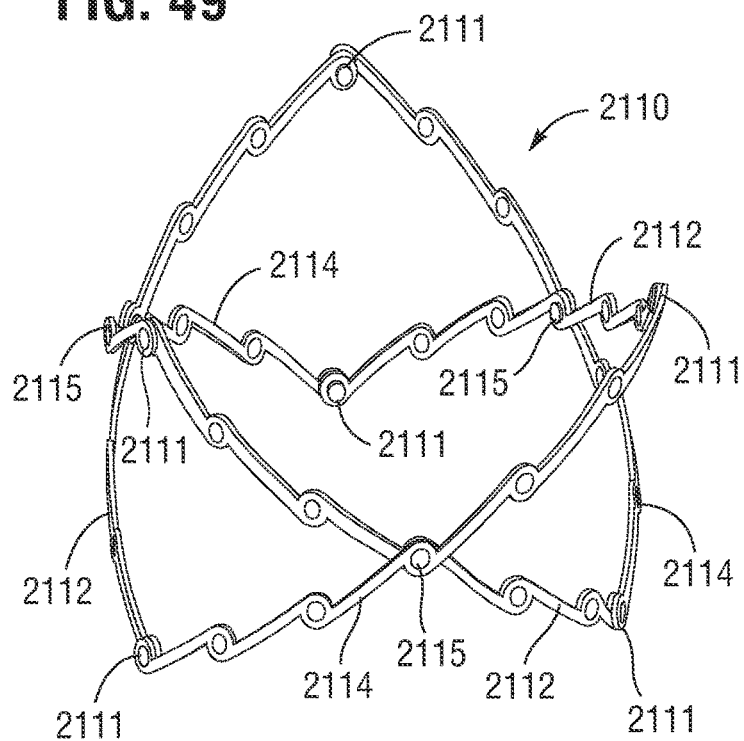
FIG. 49 is a perspective view of another embodiment of an inner frame sub-assembly for a prosthetic valve.
Figure 50:
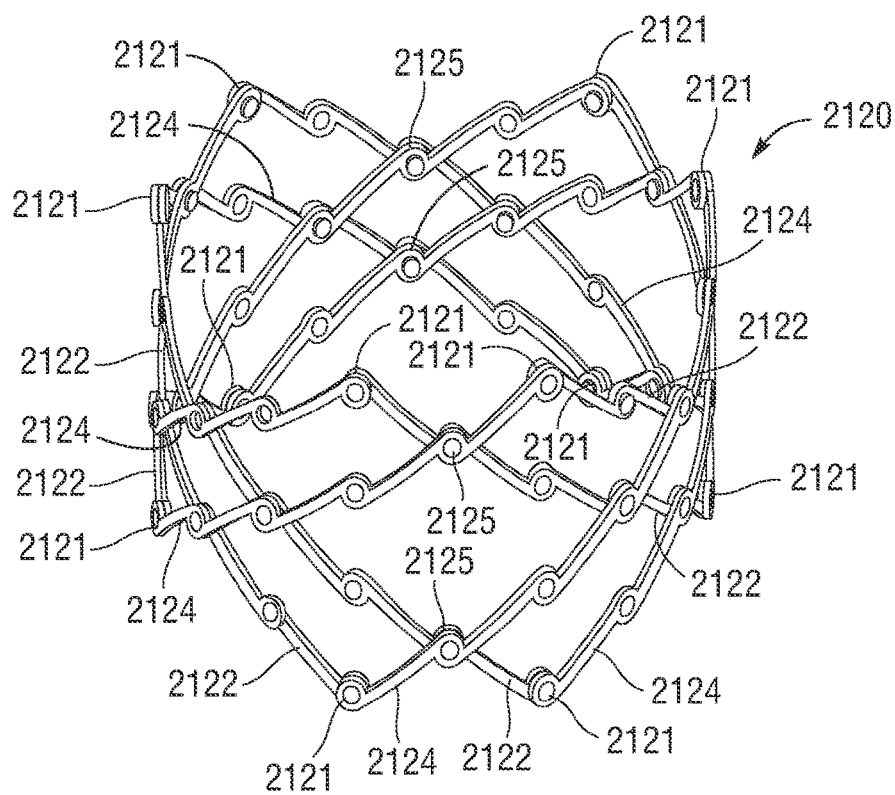
FIG. 50 is a perspective view of another embodiment of an outer frame sub-assembly formed for a prosthetic valve.
Figure 51:
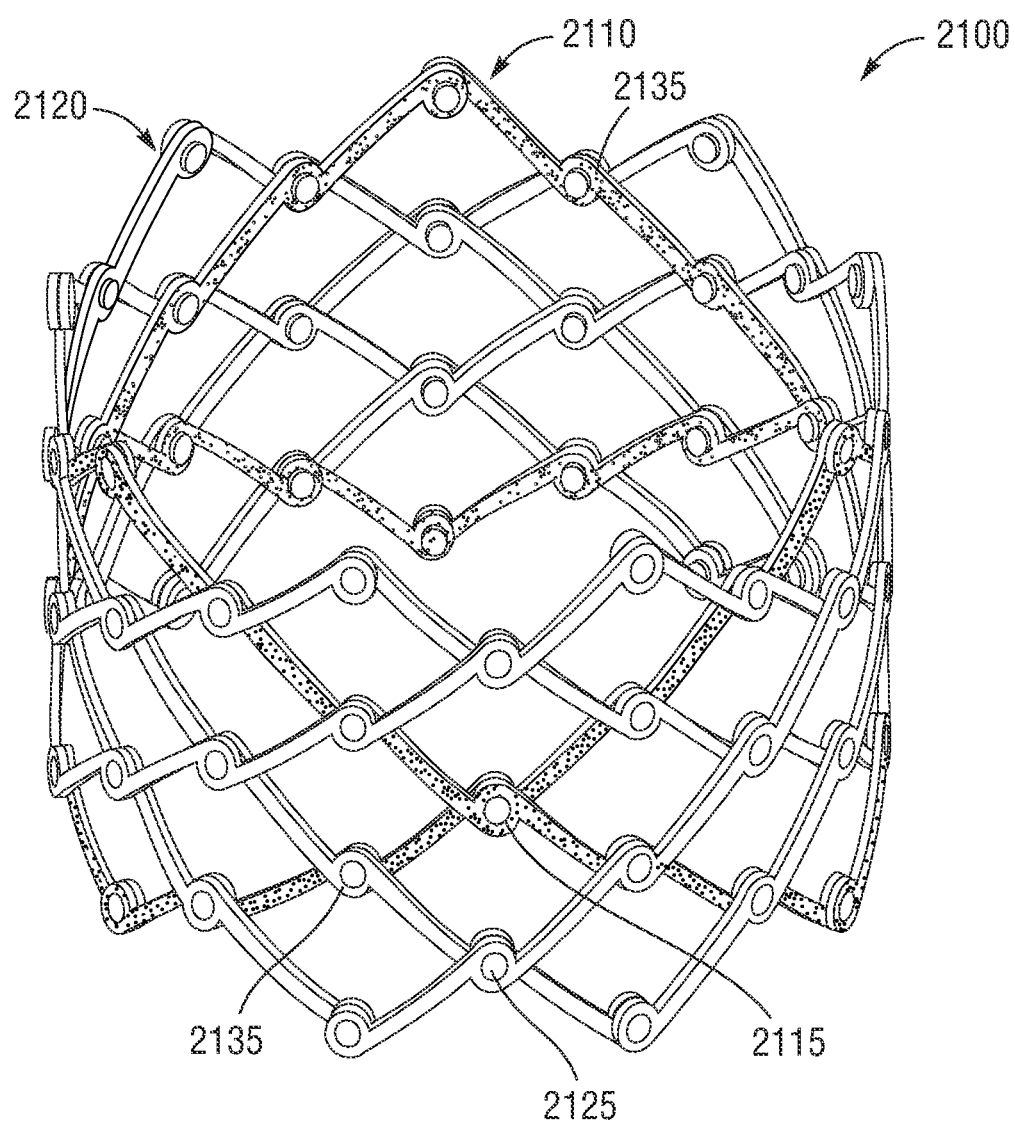
FIG. 51 is a perspective view of another frame formed by combining the inner frame sub-assembly of FIG. 49 and the outer frame sub-assembly of FIG. 50.

FIGS. 49-52 illustrate another embodiment of a frame assembly 2100 for a prosthetic valve. The frame assembly 2100 may be used when a relatively larger frame is desired. The frame assembly 2100 can be formed from an inner frame sub-assembly 2110 (FIG. 49) and an outer frame sub-assembly 2120 (FIG. 50). As illustrated in FIG. 51, the frame assembly 2100 is a "9×3" configuration, formed from nine struts positioned in a first direction and nine crossing struts positioned in a second direction, with each strut connected to another strut to form an apex at each of its ends, and to one or more additional struts in between its ends to form junctions, similar to those described above.

FIG. 49 shows the inner frame sub-assembly 2110 apart from the outer frame sub-assembly 2120. As best shown in FIG. 49, the inner frame sub-assembly 2110 may be similar to inner frame sub-assembly 1710, with three inner struts 2112 oriented in a first direction, and three crossing outer struts 2114 outer struts oriented in a second direction. The inner struts 2112 and the outer struts 2114 can be joined to each other at their ends to form apices 2111 and at junctions 2115 positioned between the ends of the struts. These junctions may be formed using projections, hinges, rivets, and/or any of the methods and/or mechanisms described herein and in the incorporated patents and applications.

FIG. 50 shows the outer frame sub-assembly 2120 apart from the inner frame sub-assembly 2110. As best shown in FIG. 50, the outer frame sub-assembly 2120 is similar to outer frame sub-assembly 1720, except that instead of three inner struts and three crossing outer struts, the outer frame sub-assembly 2120 comprises six inner struts 2212 oriented in a first direction, and six crossing outer struts 2214 outer struts oriented in a second direction. The inner struts 2212 and the outer struts 2214 can be joined to each other at their ends to form apices 2121 and at junctions 2125 positioned between the ends of the struts. These junctions may be formed using projections hinges, rivets, and/or any of the methods and/or mechanisms described herein and in the incorporated patents and applications.

FIG. 51 shows the inner frame sub-assembly 2110 assembled with the outer frame sub-assembly 2120. As illustrated in FIG. 51, once separately assembled, the inner frame sub-assembly 2110 can be inserted into outer frame sub-assembly 2120, and joined at junctions 2135 using hinges, rivets, and/or any of the methods and/or mechanisms described herein and in the incorporated patents and applications. Stippling has been added to the struts of the inner frame sub-assembly 2110 for purposes of illustration only. The stippling is added to distinguish the inner frame sub-assembly 2110 from the outer frame sub-assembly 2120 and does not represent actual surface ornamentation.

Figure 52:
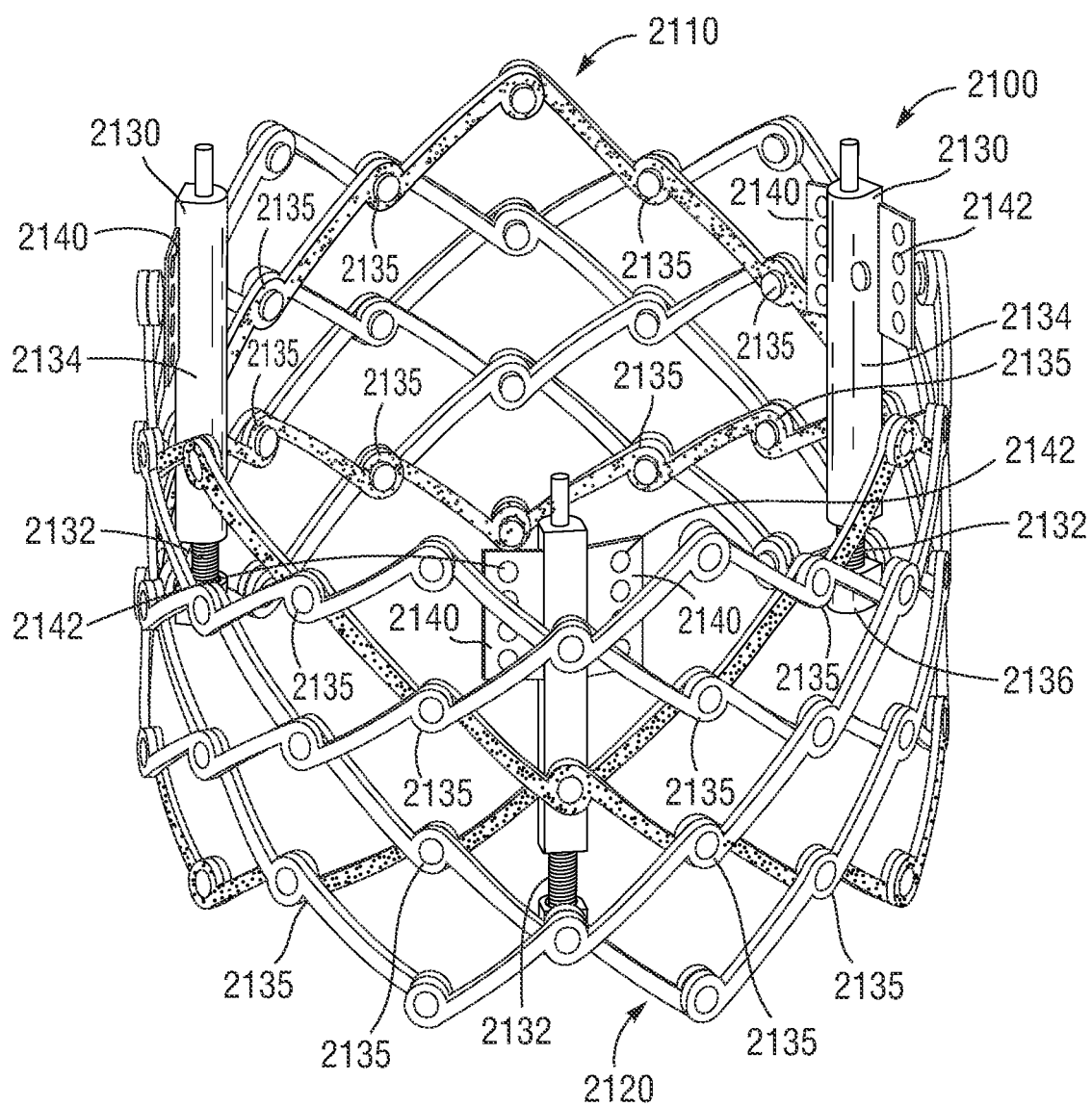
FIG. 52 is a perspective view of the frame of FIG. 51, further including threaded actuators for frame expansion and commissure attachment members for a valve leaflet assembly.

Additionally, as illustrated in FIG. 52, the two sub-assemblies may be further connected to each other via a plurality of actuators 2130. The actuators 2130 in the illustrated embodiment are screw actuators that are similar in construction and function to the screw actuators 1730. Similar to actuators 1730, each actuator 2130 in the illustrated embodiment comprises a screw 2132 that extends through an upper outer member or sleeve 2134 and a lower outer member or sleeve 2136. Rotation of the screw 2132 is effective to radially expand or compress the frame assembly 2100 as previously described. In other embodiments, the actuators can be push-pull type actuators as previously described in connection with the embodiments of FIGS. 1, 8, 12 and 21 and/or any of various actuators described in the incorporated patents and/or applications.

Additionally, a pair of commissure attachment members 2140 can be mounted to the upper end portion of each actuator 2130. The commissure attachment members 2140 of each pair can extend from diametrically opposing sides of an upper sleeve 2134 of an actuator 2130. Each pair of commissure attachment members 2140 can be used to secure a pair of commissure tabs 1914 (FIG. 46) of a leaflet assembly. Each commissure tab 1914 of a leaflet 1912 can be secured to a respective commissure attachment member 2140 by placing the commissure tab 1914 against the commissure attachment member 2140 and suturing the commissure tab 1914 in place against the commissure attachment member 2140. The sutures can extend through the commissure tab 1914 and openings 2142 in the commissure attachment member 2140. The inflow edges of the leaflets can be secured to the struts 2112, 2114 of the inner frame sub-assembly, as described above in connection with FIG. 45. A skirt (e.g., a skirt 940) can be secured to the frame assembly 2100, as previously described in connection with the embodiments of FIGS. 46-48.

Although FIG. 52 shows that the commissure attachment members 2140 are attached to respective actuators 2130, it should be understood that the commissure attachment members 2140 can also be attached to respective posts (not shown) that are separate from the actuators 2130. Generally, the posts with the commissure attachment members can be distributed equidistantly on the interior surface of the frame and each post can be spaced between adjacent actuators, wherein the frame can take any form described above, such as the frame 22 in FIG. 2, the frame 200 in FIG. 4, the frame 300 in FIG. 13, the frame 400 in FIG. 14A, the frame 1000 in FIG. 20, the frame 1100 in FIG. 21, the frame 1400 in FIG. 35A, the frame 1700 in FIG. 43, the frame 2100 in FIG. 52, etc.

In an alternative embodiment, the commissure attachment members 2140 can be attached to posts that are components of respective actuators and attached to posts that are separate from the actuators. For example, a prosthetic valve can have commissure attachment members 2140 (or commissure attachment members 2204, described below) attached to posts of actuators 2130 and posts that are separate from the actuators 2130.

FIG. 53 shows one exemplary post 2202 and a pair of commissure attachment members 2204 extending outwardly from the post 2202 and away from each other. In some embodiments, the commissure attachment members 2204 can be integrally formed on the post 2202. In some embodiments, the commissure attachment members 2204 can be separately formed and subsequently attached to the post 2202 using an adhesive, thermal bonding, welding, fasteners, and/or another suitable technique or mechanism.

In some embodiments, each post 2202 can comprise a component of an actuator configured to radially expand and compress the annular frame as described above. For example, each post 2202 can be an outer member similar to the outer member 2139 (FIG. 52) that receives an inner member 2132. Axial movement of the inner member relative to the outer member can cause radial expansion or compression the annular frame. As noted above, in other embodiments, the posts can be separate from the actuators. For example, each post 2202 can be a dedicated commissure post mounted to the frame apart from the actuators.

As shown in FIG. 53, each commissure attachment member can have a plurality of apertures 2206, which can receive sutures for securing the commissures of leaflets to the attachment members as described below. The pair of commissure attachment members 2204 can form an angle θ extending therebetween, which can be greater than 0 degree and less than 180 degrees. In some embodiments, the angle θ can be between about 90 degrees and about 150 degrees. In some embodiments, the angle θ can be about 120 degrees.

As described below, each commissure attachment member 2204 can be sized to accommodate a corresponding commissure tab of a leaflet. The commissure attachment member 2204 can have a generally rectangular shape defined by a length (L) along the axial axis of the post and a width (W) extending perpendicular to the post. In the depicted embodiment, the pair of commissure attachment members 2204 have about the same shape and size and are arranged generally symmetrically about the post 2202. In other embodiments, the pair of commissure attachment members can have different shapes or sizes, and/or can be arranged asymmetrically about the post (not shown).

FIG. 54 shows a pair of commissure reinforcement members or bars 2208, each of which can be configured to overlay a corresponding commissure attachment member 2204. The size of the reinforcement member 2208 can be the same or slightly smaller than the size of the corresponding commissure attachment member 2204. As shown, each reinforcement member 2208 can have a plurality of apertures 2210. The apertures 2210 on the reinforcement member 2208 are arranged such that the apertures 2210 are aligned with corresponding apertures 2206 on a corresponding commissure attachment member 2204 when the reinforcement member 2208 is placed over the corresponding commissure attachment member 2204.

Figure 55:
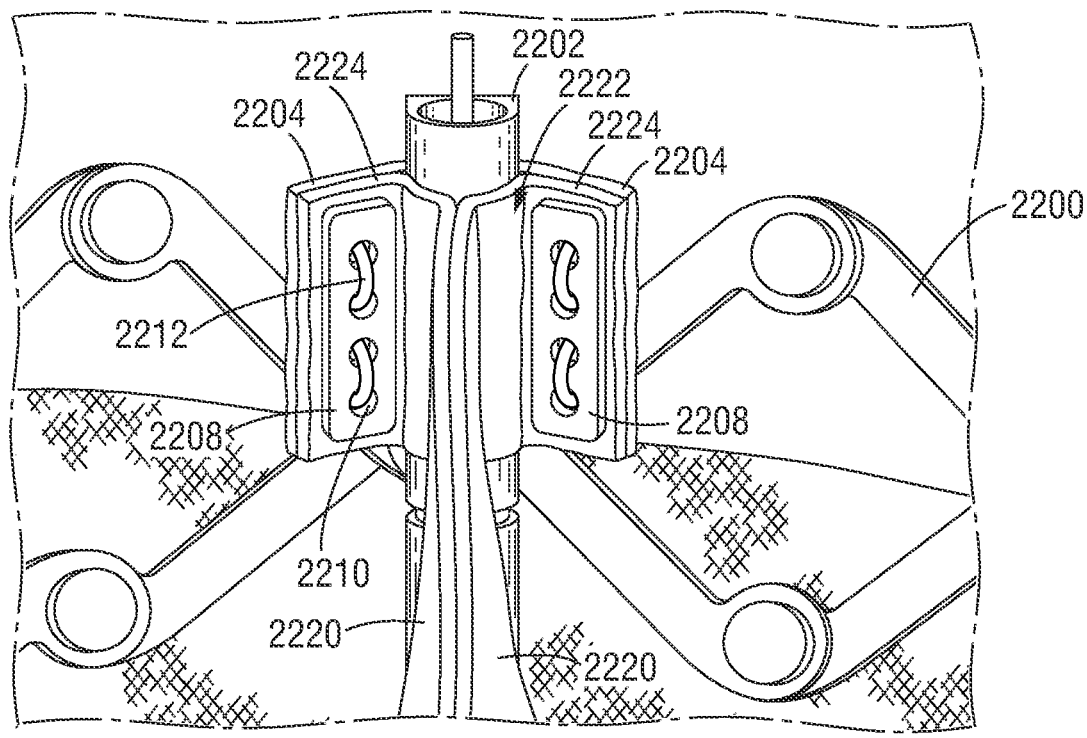
FIG. 55 shows two adjacent leaflets secured to the pair commissure attachment members and corresponding reinforcement members depicted in FIG. 54, viewed from inside a frame.
Figure 56:
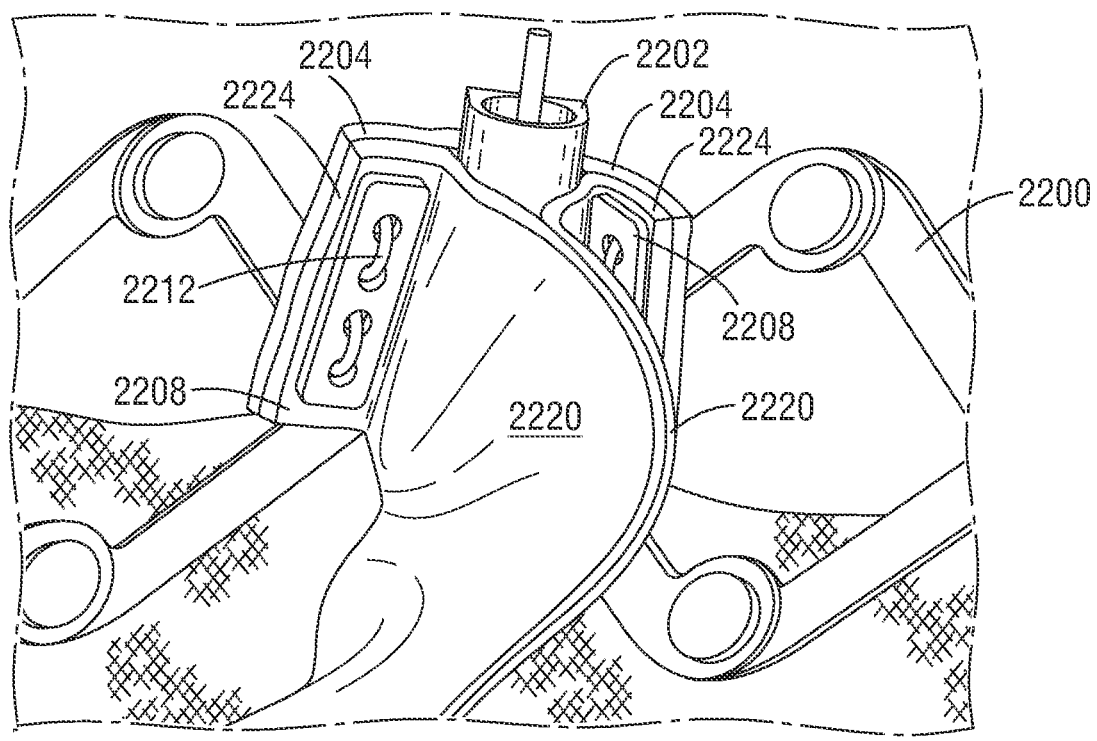
FIG. 56 shows another view of the assembly depicted in FIG. 55.
Figure 57:
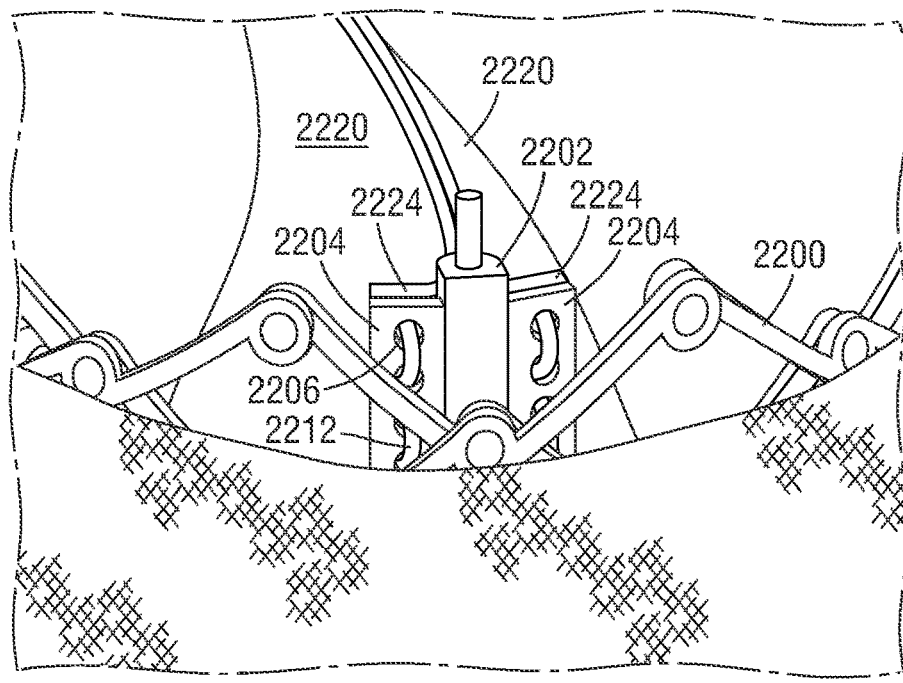
FIG. 57 shows the assembly depicted in FIG. 55, viewed from outside the frame.

FIGS. 55-57 show different views of two adjacent leaflets 2220 of a prosthetic valve that are secured to a frame 2200 by a pair of commissure attachment members 2204 and corresponding reinforcement members 2208. As shown, two adjacent leaflets can form a commissure 2222, which comprises a pair of commissure tabs 2224 (one tab 2224 from each leaflet) configured to cover the corresponding pair of the commissure attachment members 2204. The size and shape of the commissure tabs 2224 can generally match the size and shape of the corresponding commissure attachment members 2204.

Each commissure tab 2224 can be sutured to a corresponding commissure attachment member 2204 by sutures 2212 extending through the apertures 2206 and the commissure tab 2224. In addition, the pair of reinforcement members 2208 can be placed over the corresponding commissure tabs 2224 such that each commissure tab 2224 is "sandwiched" or secured between a corresponding pair of a reinforcement member 2208 and a commissure attachment member 2204. Each commissure tab 2224 can be further sutured to the corresponding reinforcement member 2208 by sutures 2212 extending through the apertures 2210. The sutures 2212 that secure a tab 2224 to a corresponding attachment member 2204 can be the same sutures that also extend through the apertures 2210 of the corresponding reinforcement member. Alternatively, different sutures can be used to stitch a tab 2224 to a corresponding attachment member 2204 and to a corresponding reinforcement member.

The reinforcement members 2208 can be made from any of various suitable materials, including metals or metal alloys (including any of the materials described herein for forming a frame), polymers (textiles or non-textiles) or natural tissue. For example, the reinforcement members 2208 can comprise a fabric member (e.g., a PET fabric).

The assembly shown in FIGS. 53-54 creates a butterfly-shaped commissure assembly (i.e., the commissure attachment members 2204 form wing-like structures on the post 2202), which offers a more secure mechanism for leaflet attachment than directly wrapping the commissure tabs 2224 around the posts 2202. The robustness of the latter approach can depend on the assembler's tightening of the commissure tabs 2224 around the respective posts 2202. Insufficient tightening can cause the commissure tabs 2224 to rotate around or axially slide out of position along the post 2202 as the prosthetic valve is crimped and/or expanded. In contrast, because the commissure tabs 2224 are sutured between the corresponding commissure attachment members 2204 and the reinforcement members 2208 (and desirably compressed therebetween), the butterfly-shaped commissure assembly described above reduces the commissures' degrees of freedom relative to the corresponding post and provides a more secure and robust attachment of the leaflet commissure to the corresponding posts.

In some embodiments, the reinforcement members 2208 can be optional. For example, a commissure tab 2224 can be directly sutured to a corresponding commissure attachment members 2204 without being covered by a reinforcement member 2208.

In some embodiments, instead of suturing through apertures 2206 and apertures 2210, the commissure tabs 2224 can be sutured to the commissure attachment members and reinforcement members with sutures positioned in recesses located along the edges of the commissure attachment members and the reinforcement members (not shown). In some embodiments, instead of using sutures, the commissure tabs 2224 can be secured to the commissure attachment members and the reinforcement members via other techniques, mechanisms or means, such as clipping mechanisms, buckles, magnets, etc.

Figure 58:
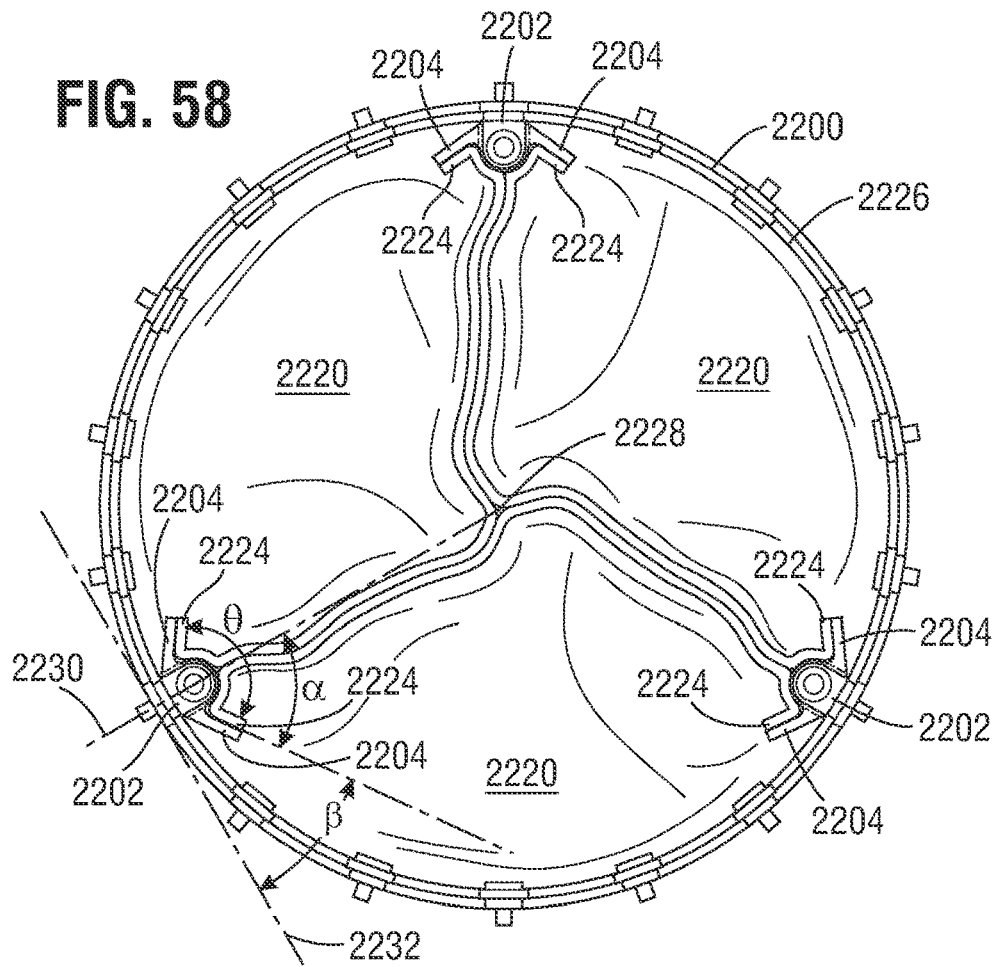
FIG. 58 is a top plan view of a prosthetic valve with three leaflets secured to three pairs of commissure attachment members attached to corresponding posts.

FIG. 58 shows a plan view of the frame 2200 with three leaflets 2220 mounted inside the frame 2200. Three posts 2202 are distributed equidistantly from each other on the interior surface 2226 of the frame 2200. A pair of commissure attachment members 2204 are attached to each post 2202. As shown, the three leaflets 2220 can form three pairs of commissure tabs 2224, which can be respectively secured to corresponding pairs of commissure attachment members 2204. Although reinforcement members are not shown in FIG. 58, it should be understood that reinforcement members can be applied to further secure the commissure tabs 2224 as described above.

Although three posts 2202 are shown in the illustrated embodiment, the number of posts 2202 in the present embodiment and other embodiments disclosed herein can be greater or fewer than three depending on the number of leaflets and therefore the number of commissures. For example, the prosthetic valve can have four posts 2202 if the prosthetic valve has four leaflets and four commissures. In another example, the prosthetic valve can have two posts 2202 if the prosthetic valve has two leaflets and two commissures. If the posts are components of actuators, then the number of actuators can be equal to the number of leaflets and commissures.

As shown in FIG. 58, a commissure attachment member 2204 can be angled inwardly relative to the interior surface 2226 of the frame 2200 at the post 2202 and points away from a central longitudinal axis 2228 of the frame 2200.

In some embodiments, the angle $\theta$ between each pair of commissure attachment members 2204 is the same or substantially the same.

In some embodiments, a commissure attachment member 2204 can form an acute angle $\alpha$ (i.e., $\alpha$ is greater than 0 degree and less than 90 degrees) with respect to a radial axis 2230 extending radially from the central axis 2228 to the post 2202 from which the commissure attachment member 2204 extends.

A commissure attachment member 2204 can also form an acute angle $\beta$ (i.e., $\beta$ is greater than 0 degree and less than 90 degrees) relative to a tangent line 2232 that is tangent to a circumference of the frame 2200 at the corresponding post 2202. Because the tangent line 2232 is perpendicular to the radial axis 2230 at the post 2202, the sum of $\alpha$ and $\beta$ is about 90 degrees.

In some embodiments, the pair of commissure attachment members 2204 can extend from the corresponding post 2202 in such directions that they are symmetric about the radial axis 2230. In other words, the angle α between each commissure attachment member 2204 and the corresponding radial axis 2230 is half of the angle θ between the pair of commissure attachment members 2204.

Figure 60:
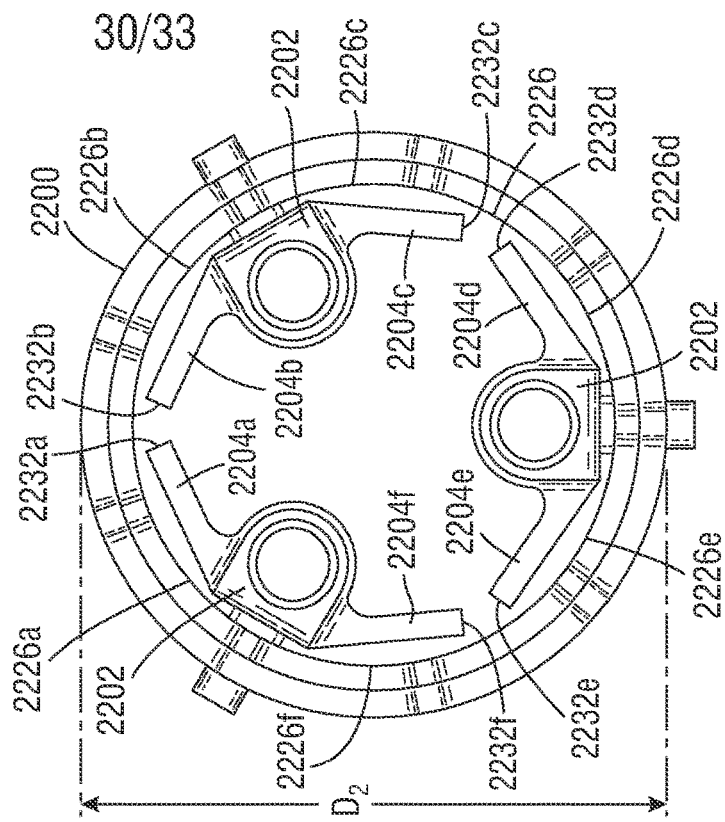
FIG. 60 is a top plan view of the frame depicted in FIG. 59 in a radially compressed configuration.
Figure 59:
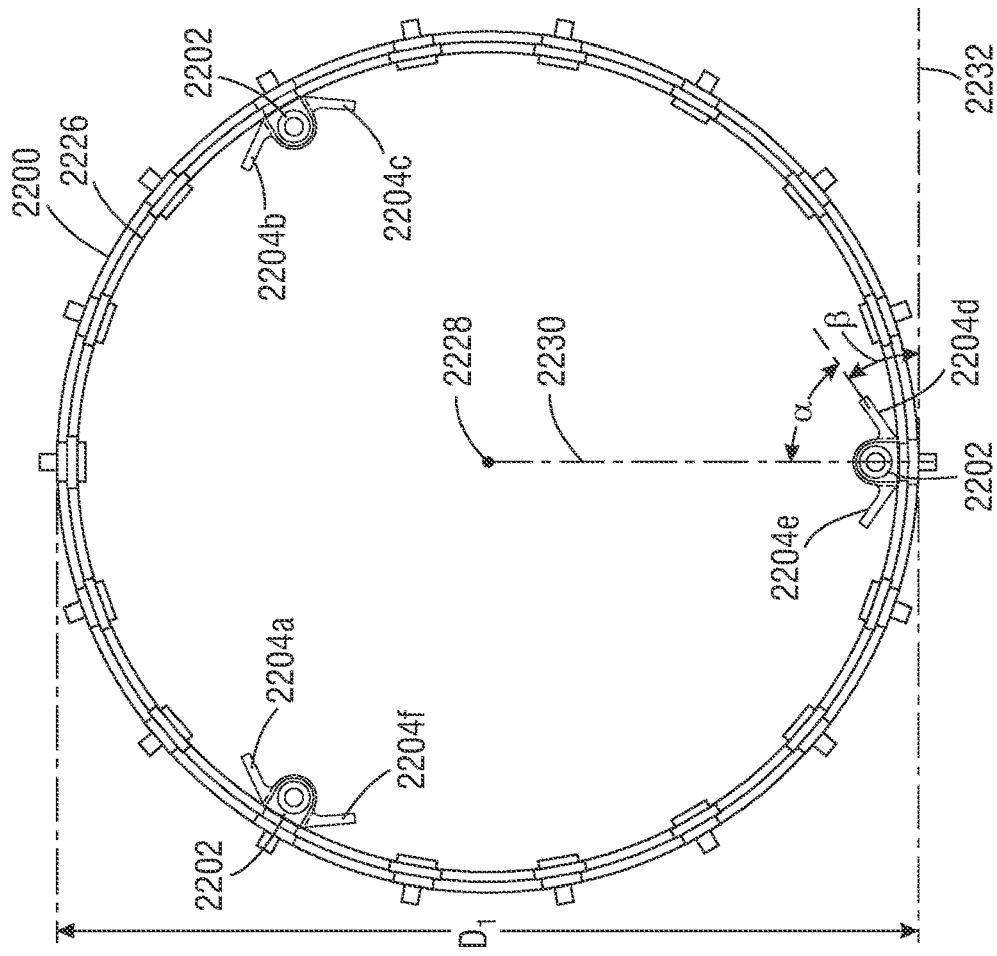
FIG. 59 is a top plan view of a frame in a radially expanded configuration, the frame having three posts, each of which has a pair of commissure attachment members.

FIGS. 59-60 show a plan view of the frame 2200 in a radially expanded configuration (having a diameter D1) and a radially compressed configuration (having a diameter D2 that is less than D1), respectively. Three pairs of commissure attachment members 2204 (individually labelled as 2204a-2204f) are respectively attached to three posts 2202. The leaflets are omitted from the figures for purpose of illustrative clarity.

When the frame 2200 is radially crimped from the radially expanded configuration (FIG. 59) to the radially compressed configuration (FIG. 60), the curvature of the interior surface 2226 of the frame 2200 increases. As described below, the commissure attachment members 2204 can be so sized and oriented that they do not hinder the mechanical compression the frame 2200.

For example, as shown in FIG. 60, the commissure attachment members 2204a-2204f can be sized and oriented such that when the frame 2200 is compressed to the diameter D2 corresponding to a fully compressed configuration (i.e., the interior surface 2206 of the frame reaches its maximum curvature), the distal ends 2232a-2232f of corresponding commissure attachment members 2204a-2204f do not touch the interior surface 2226 of the frame 2200.

In alternative embodiments, the distal ends 2232a-2232f of the commissure attachment member 2204a-2204f can barely contact the interior surface 2226 of the frame 2200 when the frame 2200 is radially compressed to diameter D2. Nonetheless, because a larger frame diameter corresponds to a smaller curvature of the interior surface 2226, the distal ends 2232a-2232f of corresponding commissure attachment members 2204a-2204f do not contact the interior surface 2226 of the frame 2200 before the frame 2200 is radially crimped to diameter D2. Thus, crimping of the frame 2200 is not hindered by contact between the distal end 2232a-2232f of the commissure attachment member 2204a-2204f as the frame is compressed.

In some embodiments, when the frame 2200 is in the radially compressed configuration, each commissure attachment member 2204a-2204f can be generally parallel to a corresponding portion 2226a-2226f of the interior surface of the frame 2200 that is adjacent to the commissure attachment member, such that the opposing ends of the attachment members are spaced evenly from the inner surface 2226 of the frame 2200.

In some embodiments, each commissure attachment member can be spaced apart from an adjacent commissure attachment member of an adjacent post when the frame is in the radially compressed configuration. For example, FIG. 60 shows that the outer end 2232a of commissure attachment member 2204a does not touch the outer end 2232b of its adjacent commissure attachment member 2204b of the adjacent post when the frame 2200 is fully compressed.

In alternative embodiments, the outer end of one commissure attachment member can barely contact the outer end of its adjacent commissure attachment member of an adjacent post when the frame 2200 is compressed to its smallest radial diameter D2. However, no such contact exists when the frame diameter is greater than D2. Thus, radially compression of the frame 2200 is not hindered by the impingement between adjacent commissure attachment members.

In some embodiments, the acute angle R between a commissure attachment member 2204 and the tangent line 2232 at the corresponding post 2202 can range from about 5 degrees to about 85 degrees, from about 15 degrees to about 75 degrees in some embodiments, from about 25 degrees to about 65 degrees in some embodiments, from about 35 degrees to about 65 degrees in some embodiments, and from about 45 degrees to about 55 degrees in some embodiments. Similarly, the acute angle α between the commissure attachment member 2204 and the radial axis 2230 passing through the post 2202 can range from about 5 degrees to about 85 degrees in some embodiments, from about 15 degrees to about 75 degrees in some embodiments, from about 25 degrees to about 65 degrees in some embodiments, from about 35 degrees to about 65 degrees in some embodiments, and from about 45 degrees to about 55 degrees in some embodiments. In a specific example, the acute angle R can be about 30 degrees (correspondingly, the acute angle α can be about 60 degrees).

In some embodiments, the width W of each commissure attachment member 2204 extending from corresponding post 2202 can be equal to or less than the smallest radius (i.e., D2/2) of the frame 2200 in its fully compressed configuration.

Figure 61:
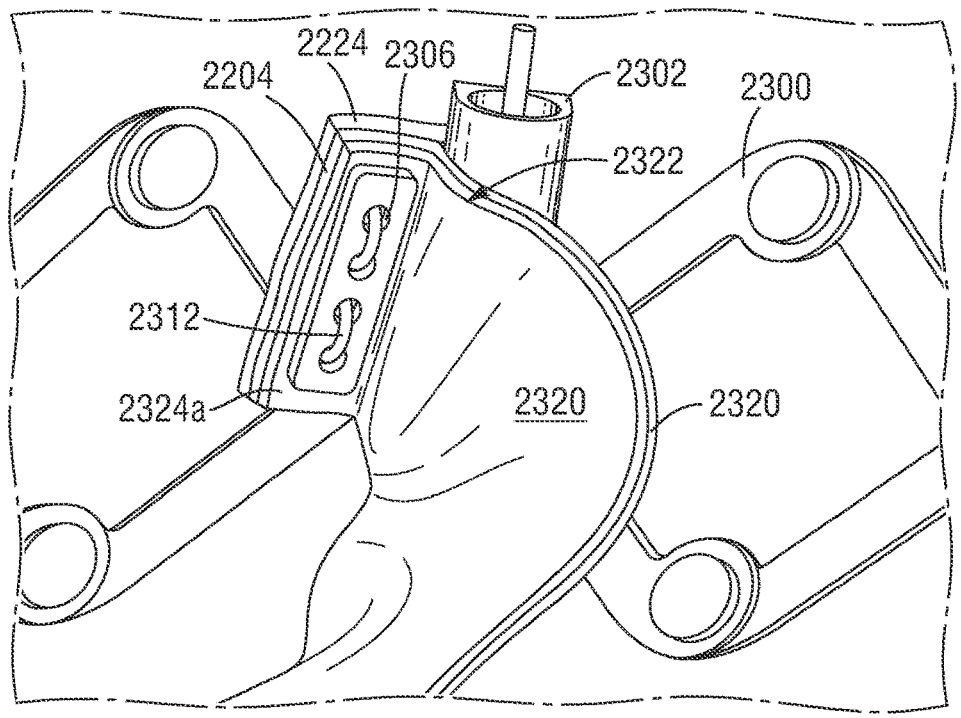
FIG. 61 is a perspective view of a post having one commissure attachment member, according to another embodiment.

FIG. 61 shows another embodiment, where a post 2302 mounted on a frame 2300 has only one (instead of a pair of) commissure attachment member 2304 that can have a plurality of apertures 2306. As shown, two adjacent leaflets 2320 can form a commissure 2322, which comprises a pair of commissure tabs 2324a, 2324b. Both commissure tabs 2324a, 2324b can be secured to the same commissure attachment member 2304. For example, one commissure tab 23224a can be placed against another commissure tab 2324b to form a double layer, which can be sutured together to the commissure attachment member 2304 by sutures 2312 (e.g., which can extend through the apertures 2306) and/or other attachment means or mechanisms. Optionally, a reinforcement member can be placed against the double layer so that the double layer is sandwiched or secured between the commissure attachment member and the reinforcement member. The reinforcement member can be sutured together with the double layer by sutures through a plurality of apertures in the reinforcement member.

In an alternative embodiment, the pair of commissure tabs 2324a, 2324b can be secured to opposite sides of the commissure attachment member 2304 (not shown). For example, one commissure tab 2324a can be placed on the interior side (facing inwardly of the frame) of the commissure attachment member 2304 and the other commissure tab 2324b can be folded around the post 2302 and placed on the exterior side (facing outwardly of the frame) of the commissure attachment member 2304. Then, both commissure tabs 2324a, 2324b can be sutured together to the commissure attachment member 2304 through the apertures 2306. Optionally, the commissure tabs on either side of the commissure attachment member 2304 can be covered by and sutured to a reinforcement member.

Figure 62:
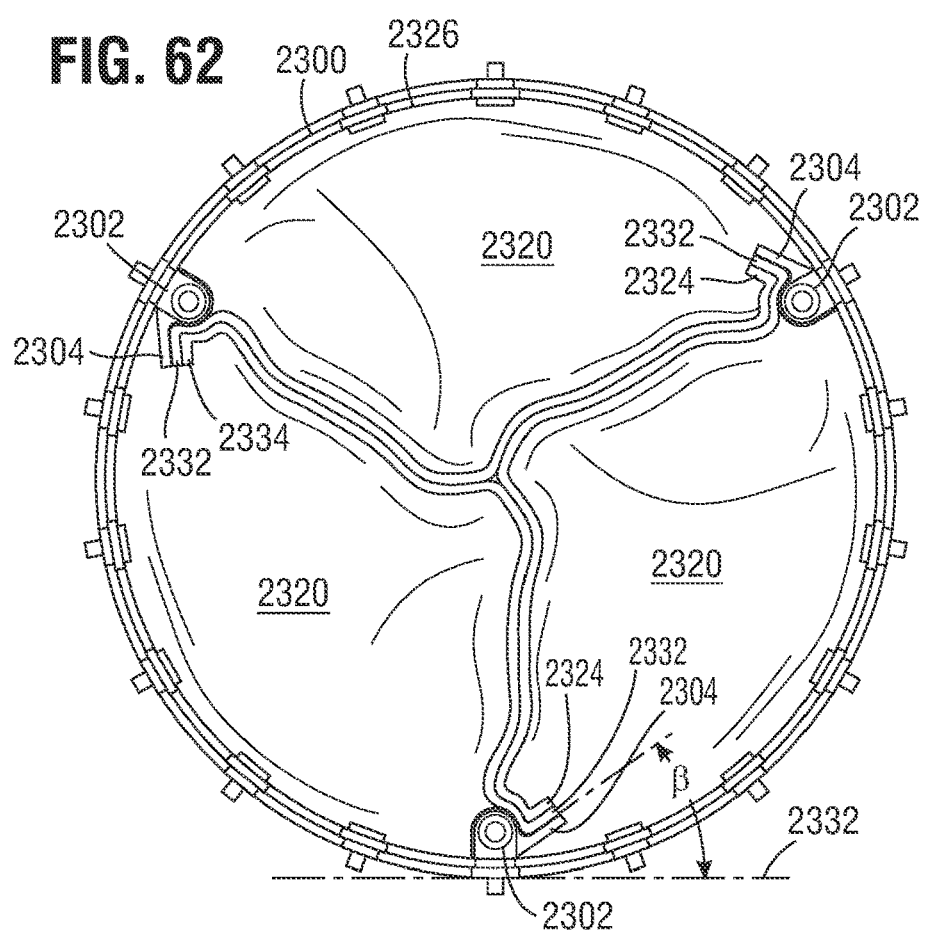
FIG. 62 is a top plan view of a prosthetic valve with three leaflets being secured by three commissure attachment members attached to corresponding posts.

FIG. 62 shows the plan view of the frame 2300 having three mounted leaflets 2320. Three posts 2302 are distributed equidistantly on the interior surface 2326 of the frame 2300. Each post 2302 has one commissure attachment member 2304 extending outwardly from the post 2302. The three commissure attachment members 2304 can be positioned clockwise or counterclockwise relative to the respective posts 2302 such that one commissure attachment member 2304 is located between any two adjacent posts 2302.

Each commissure attachment member 2304 can form an acute angle R relative to a tangent line 2332 that is tangent to a circumference of the frame 2300 at the corresponding post 2302. As shown, the three leaflets 2320 can form three pairs of commissure tabs 2324. Each pair of commissure tabs 2324 can be secured to a corresponding commissure attachment member 2304 as described above.

The commissure attachment members 2304 can be so sized and oriented that when the frame 2300 is compressed to its radially compressed configuration, an outer end 2332 of the commissure attachment member 2304 does not touch the interior surface 2326 of the frame 2300. In addition, each commissure attachment member 2304 can be spaced apart from an adjacent post 2302 when the frame 2300 is in the radially compressed configuration. As such, the commissure attachment members 2304 do not inhibit the mechanical compression the frame 2300.

In some embodiments, the acute angle R between a commissure attachment member 2304 and the tangent line 2332 at the corresponding post 2302 can range from about 15 degrees to about 45 degrees, from about 5 degrees to about 85 degrees in some embodiments, from about 15 degrees to about 75 degrees in some embodiments, from about 25 degrees to about 65 degrees in some embodiments, from about 35 degrees to about 65 degrees in some embodiments, and from about 45 degrees to about 55 degrees in some embodiments. In a specific embodiment, the acute angle β can be about 30 degrees.

Because there is only one commissure attachment member 2304 between two adjacent posts 2302, the commissure attachment member 2304 can have a larger width W than the one shown in FIG. 60 without causing the impingement between a commissure attachment member and its adjacent post when crimping the frame. For example, the width W of each commissure attachment member 2304 extending from the post 2302 can be equal to or less than about 1.73 times the smallest radius of the frame 2300 in its fully compressed configuration.

FIGS. 63-64 shows another embodiment, where commissure attachment members 2404 can have a curved shape instead of being straight and angled inwardly relative to the frame 2400 (the leaflets are omitted for purposes of illustration). For example, each commissure attachment member 2404 can extend from a respective post 2402 in a generally circumferential direction when the frame 2400 is in the radially expanded configuration (FIG. 63), and the commissure attachment member 2404 can be configured to resiliently fold inwardly and deform under the force of the frame 2400 as the frame 2400 is compressed to the radially compressed configuration (FIG. 64).

Although FIGS. 63-64 show that each post 2402 has a pair of commissure attachment members 2404, it should be understood that each post can also have only one commissure attachment member to which the pair of commissure tabs are secured.

In one embodiment, the commissure attachment members 2404 can be manufactured from an elastic material (e.g., Nitinol). As such, when the frame 2400 is in the fully expanded configuration, each commissure attachment member 2404 can extend along and conform to the interior surface 2426 of the frame 2400 near the post 2402. As the frame 24 is compressed during crimping, the elastic commissure attachment members 2404 can be folded inwardly and deformed by the frame 2400 so as to conform to the inner surface of the frame in the radially compressed state. When the frame 2400 is radially expanded upon deployment of the prosthetic valve inside a patient's body, the commissure attachment members 2404 can revert back to their original shape (FIG. 63) under their own resiliency.

In alternative embodiments, a commissure attachment member can be pivotably connected to a post, such as with a hinge joint connecting the commissure attachment member to the post. The hinge allows the commissure attachment member to pivot inwardly relative to the frame with respect to a longitudinal pivot axis during radial compression of the frame. For example, referring to FIG. 53, each commissure attachment member 2204 can coupled to the post 2202 by a hinge joint (e.g., a hinge pin extending through knuckle portions formed on the attachment member 2204 and the post similar to a door hinge), allowing each commissure attachment member 2204 to pivot relative to the post with respect to a longitudinal axis that is parallel to the longitudinal axis of the post and the central longitudinal axis of the frame. In this manner, the commissure attachment members can pivot inwardly as the frame is radially compressed so as not to inhibit compression of the frame.

When the frame is radially expanded in a patient's body, the commissure attachment members can be free to pivot back outwardly closer to the frame under the pressure gradient of blood flowing through the prosthetic valve. Each hinge joint can be configured to limit the extent that the commissure attachment member can pivot radially toward the frame such that no portions of the leaflets can contact the inner surface of the frame when the leaflets move to their open position under the flow of blood through the prosthetic valve.

In another example, each commissure attachment member 2204 can be coupled to the post 2202 by a living hinge that allows the commissure attachment member to fold inwardly relative to the frame during radially compression of the frame (which is similar to that described above for the embodiment of FIGS. 63-64 but does not necessarily require the commissure attachment member to conform to the curvature of the frame). The living hinge can be, for example, a portion of the commissure attachment member having a reduced thickness where it is connected to the post. It should be noted that the embodiment of FIGS. 61-62 can also have commissure attachment members pivotably connected to respective posts by hinge joints as described above for the embodiment of FIG. 53.

When a commissure attachment member is coupled to a post by a hinge joint, a biasing member (for example, a torsion spring or another type of spring) can be provided to resiliently bias the commissure attachment member to pivot radially outward to a position closer to the frame when the frame is radially expanded.

General Considerations

It should be understood that the disclosed embodiments can be adapted for use with prosthetic devices that are implantable in any of the native annuluses of the heart (e.g., the pulmonary, mitral, and tricuspid annuluses), and can be used with any of various delivery approaches (e.g., retrograde, antegrade, transseptal, transventricular, transatrial, etc.). The disclosed embodiments can also be used with prostheses implanted in other lumens of the body.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

As used herein, the term "approximately" and "about" means the listed value and any value that is within 10% of the listed value. For example, "about 30 degrees" means any value between 27-33 degrees, inclusive.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A prosthetic valve assembly comprising:
   an annular frame being radially expandable and compressible between a radially compressed configuration and a radially expanded configuration;
   a valvular structure comprising a plurality of leaflets mounted inside the annular frame, wherein each two adjacent leaflets form a pair of commissure tabs;
   a plurality of posts mounted on an interior surface of the annular frame; and
   a pair of commissure attachment members extending outwardly from each post and away from each other, wherein each pair of commissure tabs is attached to a corresponding pair of the commissure attachment members.

2. The assembly of claim 1, wherein an angle is formed between each pair of commissure attachment members, wherein the angle is greater than 90 degrees.

3. The assembly of claim 1, wherein the pair of commissure attachment members extending outwardly from each post are symmetric about the post.

4. The assembly of claim 1, wherein each commissure attachment member comprises a plurality of apertures and a corresponding commissure tab is coupled to the commissure attachment member via sutures extending through the plurality of apertures.

5. The assembly of claim 1, further comprising a plurality of reinforcement members, each of which is configured to be positioned radially inwardly of a corresponding commissure attachment member, wherein each commissure tab is secured between a corresponding pair of a reinforcement member and a commissure attachment member.

6. The assembly of claim 5, wherein each reinforcement member comprises a plurality of apertures and a corresponding commissure tab is coupled to the reinforcement member via sutures extending through the plurality of apertures.

7. The assembly of claim 5, wherein the reinforcement members comprise a fabric member.

8. The assembly of claim 1, wherein each commissure tab is sized and shaped to match a corresponding commissure attachment member.

9. The assembly of claim 1, wherein each commissure attachment member is spaced apart from an adjacent commissure attachment member of an adjacent post when the frame is in the radially compressed configuration.

10. The assembly of claim 1, wherein an outer end of each commissure attachment member is spaced apart from an interior surface of the frame when the frame is in the radially compressed configuration.

11. The assembly of claim 1, wherein each commissure attachment member extends from a respective post in a generally circumferential direction when the frame is in the radially expanded configuration, and the commissure attachment member is configured to resiliently fold inwardly as the frame is compressed to the radially compressed configuration.

12. The assembly of claim 1, wherein each post comprises a component of an actuator configured to radially expand and compress the annular frame.

13. The assembly of claim 1, wherein the annular frame comprises a plurality of first struts and a plurality of second struts, wherein the first struts overlap adjacent second struts at junctions and radial expansion or compression of the annular frame causes the first struts to pivot relative to the second struts at the junctions, wherein the first struts have a larger plastic deformation range than the second struts.

14. A prosthetic valve assembly comprising:
   an annular frame being radially expandable and compressible between a radially compressed configuration and a radially expanded configuration;

a valvular structure comprising a plurality of leaflets mounted inside the annular frame, wherein each two adjacent leaflets form a commissure;

a plurality of posts mounted on the annular frame; and at least one commissure attachment member extending outwardly from each post, wherein each commissure attachment member comprises a plurality of apertures, wherein each commissure comprises a pair of commissure tabs that are attached to a respective commissure attachment member via sutures extending through the plurality of apertures, wherein each commissure attachment member comprises a planar plate on which the pair of commissure tabs are placed, wherein the planar plate and the pair of commissure tabs form an acute angle relative to a tangent line that is tangent to a circumference of the frame at the corresponding post.

15. The assembly of claim 14, wherein each commissure attachment member extends from a respective post in a generally circumferential direction when the frame is in the radially expanded configuration, and the commissure attachment member is configured to resiliently fold inwardly as the frame is compressed to the radially compressed configuration.

16. The assembly of claim 14, further comprising a plurality of reinforcement members, each of which is configured to be positioned radially inwardly from a corresponding commissure attachment member, wherein each commissure is secured between a corresponding pair of a reinforcement member and a commissure attachment member.

17. The assembly of claim 14, wherein each commissure attachment member comprises an elastic material.

18. The assembly of claim 14, wherein each commissure attachment member has a rectangular shape defined by a length along an axial axis of the corresponding post and a width extending perpendicular to the post.

19. The assembly of claim 14, wherein the pair of commissure tabs form a double layer which is sutured together to the corresponding commissure attachment member.

20. The assembly of claim 14, wherein each commissure comprises a pair of commissure tabs, wherein the pair of commissure tabs are secured to opposite sides of the corresponding commissure attachment member.

21. The assembly of claim 14, wherein each commissure attachment member is hingedly connected to a respective post such that the commissure attachment member can pivot relative to the post when the frame moves between the radially compressed configuration and the radially expanded configuration.

22. A prosthetic valve assembly comprising:

an annular frame being radially expandable and compressible between a radially compressed configuration and a radially expanded configuration;

a valvular structure comprising a plurality of leaflets mounted inside the annular frame, wherein each two adjacent leaflets form a pair of commissure tabs;

a plurality of posts mounted on the annular frame; and a pair of commissure attachment members extending outwardly from each post and away from each other, wherein each pair of commissure tabs is attached to a corresponding pair of the commissure attachment members, wherein the pair of commissure attachment members are deformed by the annular frame as the annular frame moves from the radially expanded configuration to the radially compressed configuration.

* * * * *